(12) United States Patent
Chen et al.

(10) Patent No.: US 10,189,795 B2
(45) Date of Patent: Jan. 29, 2019

(54) ARYL AMINE SUBSTITUTED QUINOXALINE USED AS ANTICANCER DRUGS

(71) Applicants: Kuen-Feng Chen, Taipei (TW); Chung-Wai Shiau, Taipei (TW)

(72) Inventors: Kuen-Feng Chen, Taipei (TW); Chung-Wai Shiau, Taipei (TW); Chih-Hung Chen, Hsinchu County (TW)

(73) Assignees: Kuen-Feng Chen, Taipei (TW); Chung-Wai Shiau, Taipei (TW)

( * ) Notice: Subject to any disclaimer, the term of this patent is extended or adjusted under 35 U.S.C. 154(b) by 0 days.

(21) Appl. No.: 15/324,243

(22) PCT Filed: Jul. 7, 2015

(86) PCT No.: PCT/CN2015/083466
§ 371 (c)(1),
(2) Date: Jan. 5, 2017

(87) PCT Pub. No.: WO2016/004856
PCT Pub. Date: Jan. 14, 2016

(65) Prior Publication Data
US 2017/0204071 A1    Jul. 20, 2017

Related U.S. Application Data

(60) Provisional application No. 62/021,214, filed on Jul. 7, 2014.

(51) Int. Cl.
| | | |
|---|---|---|
| A61K 31/498 | (2006.01) | |
| C07D 241/44 | (2006.01) | |
| A61K 45/06 | (2006.01) | |

(52) U.S. Cl.
CPC .......... *C07D 241/44* (2013.01); *A61K 31/498* (2013.01); *A61K 45/06* (2013.01)

(58) Field of Classification Search
CPC .................................................. A61K 31/498
USPC ....................................................... 514/249
See application file for complete search history.

(56) References Cited

FOREIGN PATENT DOCUMENTS

| WO | WO0220463 A2 | 3/2002 | | |
|---|---|---|---|---|
| WO | WO 2002020463 | * 3/2002 | .......... | C07C 233/75 |
| WO | WO 2006044402 | * 4/2006 | .......... | C07D 498/04 |

OTHER PUBLICATIONS

Waisser, et. al., Scientia Pharmaceutica (1997), 65(3), 109-112.*
Lockhart, et. al., Journal of the Chemical Society (1937) 424-7.*
Haworth, et. al., Journal of the Chemical Society (1948) 777-82.*
Beckert, et. al., Pharmazie (1997), 52(8), 638-639.*
Khan, et. al., Indian Journal of Heterocyclic Chemistry (2008), 18(2), 197-198.*
Yu, H. C. et al., "Erlotinib derivative inhibits hepatocellular carcinoma by targeting CIP2A to reactivate protein phosphatase 2A", Cell Death & Disease, vol. 5, No. 7, Jul. 31, 2014.
Babu, P. V. et al., "Ligand/PTC-free Intramolecular Heck Reaction: Synthesis of Pyrroloquinoxalines and Their Evaluation Against PDE4/Luciferase/Oral Cancer Cell Growth in Vitro and Zebratish in Vivo", Organic & Biomolecular Chemistry, vol. 11, No. 39, Aug. 5, 2013.
Waisser, K. et al., "Antimycobacterial Activity of Some 2, 3-Dianilinoquinoxaline Derivatives", Pharmazie, vol. 52, No. 10, Dec. 31, 1997.
Khan, S. A et al, "Synthesis and Antimicrobial Activity of 2, 3-Di-Subdtituted Quinoxalines", Indian Journal of Heterocyclic Chemistry, vol. 18, No. 2, Dec. 31, 2008.
Waisser, K. et al., "Antimycobacterial Activity of Some 2, 3-Dianilinoquinoxaline Derivatives with Substituents in Position 6", Scientia Pharmaceutica, vol. 65, No. 3, Dec. 31, 1997.

* cited by examiner

*Primary Examiner* — Jeffrey H Murray
(74) *Attorney, Agent, or Firm* — WPAT, PC

(57) ABSTRACT

The present invention provides new compounds of formula I(a)-I(d) and II, The compounds can inhibit cancerous inhibitor of protein phosphate 2A (CIP2A), can be used as protein phosphate 2A (PP2A) accelerator and oncoprotein SET antagonist, and can treat cancers effectively.

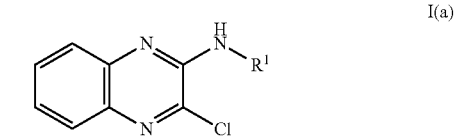

I(a)

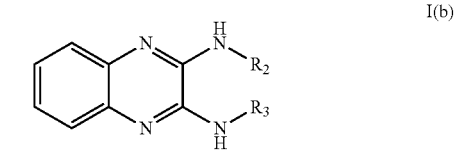

I(b)

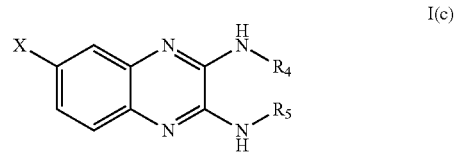

I(c)

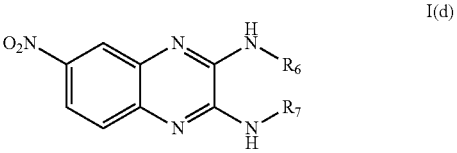

I(d)

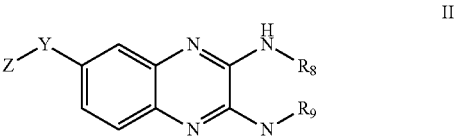

II

7 Claims, 38 Drawing Sheets

ARYL AMINE SUBSTITUTED QUINOXALINE USED AS ANTICANCER DRUGS

BACKGROUND OF THE INVENTION

1. Field of the Invention

The present invention relates to new compounds having an aryl amine substituted quinoxaline and their use.

2. The Prior Arts

Overexpression of cancerous inhibitor of protein phosphatase 2A (abbreviated as CIP2A) has been found in several common human cancers including acute leukemia, prostate cancer, non-small cell lung cancer, gastric cancer, head or neck cancer, colon cancer and breast cancer and has been linked to clinical aggressiveness in tumors and promotion of the malignant growth of cancer cells. CIP2A interacts directly with the transcription factor c-Myc and inhibits the PP2A dephosphorylation of c-Myc, thereby stabilizing the oncogenic c-Myc from degradation.

Protein phosphatase 2A (abbreviated as PP2A) is a crucial regulator of cell proliferation by dephosphorylation of protein kinases on serine or threonine residues. PP2A is composed of three subunits which regulate substrate specificity, cellular localization and enzymatic activity. For example, PP2A dephosphorylates p-Akt at serine 473 and reduces the cell growth. Hence, the CIP2A-PP2A-Akt signaling cascade is thought to be an important survival regulator in cancers. In addition, SET has been found as another potent inhibitor of PP2A, and the expression of SET has been found in tumor tissues of different human malignant disease, the expression level of SET is closely correlated with cell growth rate.

Accordingly, it needs to develop a compound which is capable of antagonize SET or CIP2A repressing PP2A to reactive PP2A in cancer cells and subsequently reducing p-Akt cancer signal cascade to induce tumor cell apoptosis, the compound can be a new anticancer strategy.

SUMMARY OF THE INVENTION

The present invention provides new compounds, which can inhibit the binding ability of PP2A and SET, and also effectively inhibit cancerous inhibitor of protein phosphatase 2A (CIP2A) and p-Akt expression. It can be used as protein phosphate 2A (PP2A) accelerator and oncoprotein SET antagonist, and can treat cancers effectively.

One objective of the present invention is to provide an aryl amine substituted quinoxaline which is represented by Formula I(a) or Formula I(b)

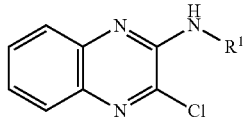
I(a)

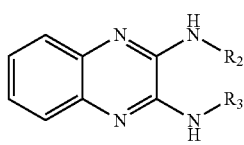
I(b)

wherein $R^1$, $R^2$ and $R^3$ are same or different substituted phenyl groups and are independently phenyl substituted with an atom or group, aromatic heterocyclic group, and the substituted phenyl group each is

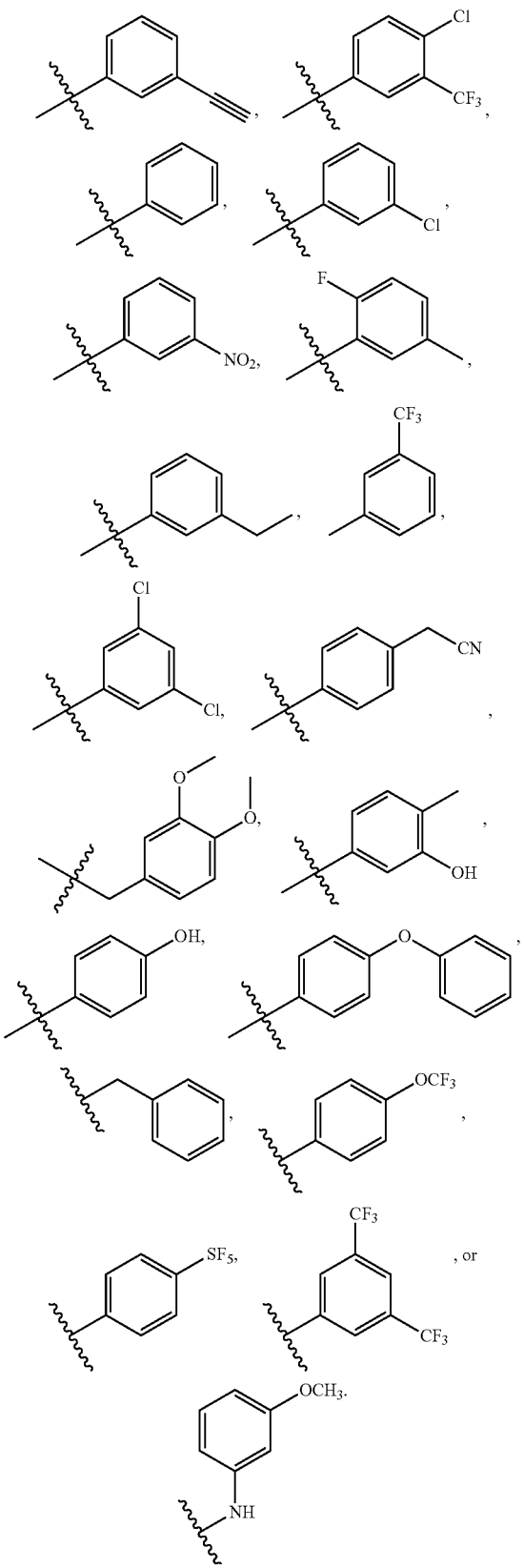

Another objective of the present invention is to provide an aryl amine substituted quinoxaline which is represented by Formula I(c)

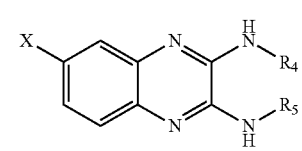

wherein $R^4$ and $R^5$ are same or different substituted phenyl groups and are independently phenyl substituted with an atom or group, aromatic heterocyclic group, and the substituted phenyl group each

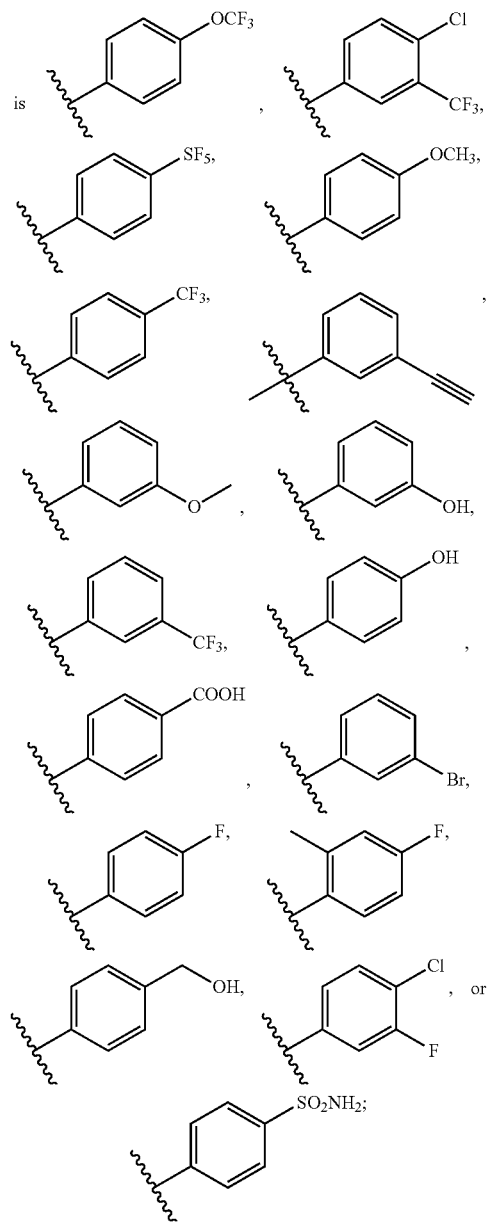

and
wherein X is halogen, haloalkyl, methoxy, nitro, amino, amido, carboxyl, acid, benzophenone or methoxycarbonyl.

Another objective of the present invention is to provide an aryl amine substituted quinoxaline which is represented by Formula I(d)

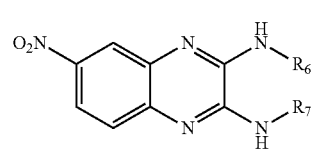

wherein $R^6$ and $R^7$ are same or different substituted phenyl groups and are independently phenyl substituted with an atom or group, aromatic heterocyclic group, and the substituted phenyl group each is

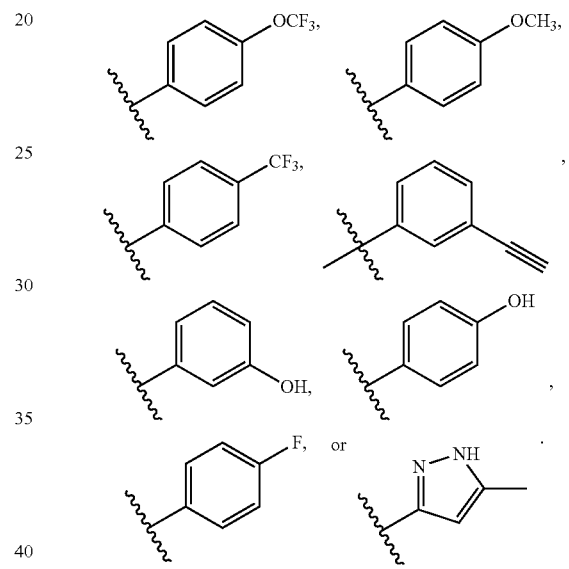

A further objective of the present invention is to provide an aryl amine substituted quinoxaline which is represented by Formula II

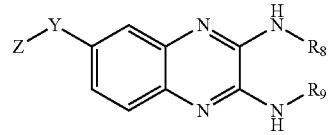

wherein $R^8$ and $R^9$ are same or different substituted phenyl groups and are independently phenyl substituted with an atom or group, and the substituted phenyl group each is

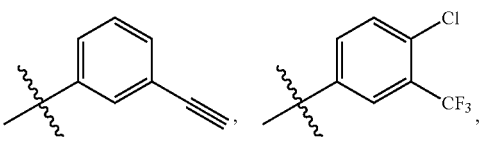

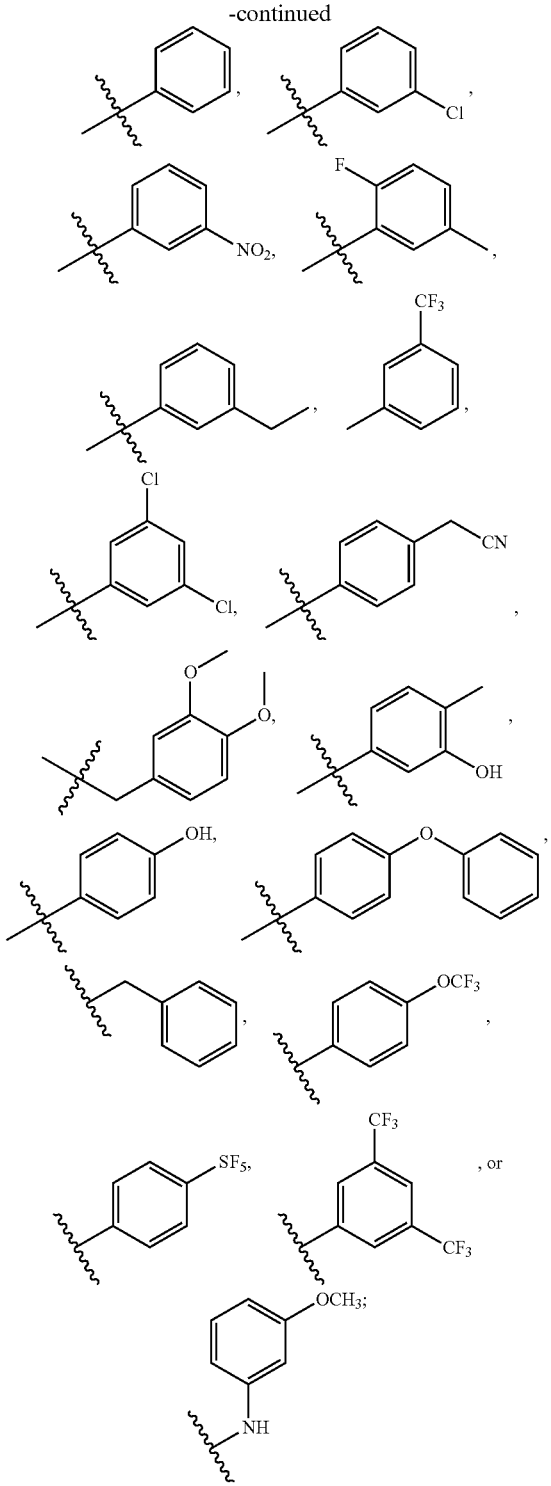

and wherein Y is CO or $(CH_2)_n$, n=1-3; Z=$COOR^{10}$, or a phenyl substituted with a funtional group, $R^{10}$ is aryl or alkyl.

Another objective of the present invention is to provide a pharmaceutical composition comprising an above-described compound and a pharmacological acceptable carrier.

Another objective of the present invention is to provide a pharmaceutical composition for enhancing protein phosphatase 2A (PP2A) activity in a cell, used as oncoprotein SET antagonist or cancerous inhibitor of protein phosphatase 2A (CIP2A) inhibitor, and disrupting the binding between oncoprotein SET and protein phosphatase 2A (PP2A), comprising an above-described compound and a pharmacological acceptable carrier.

Another objective of the present invention is to provide a pharmaceutical composition for treating a disease or condition characterized by inactive protein phosphatase 2A (PP2A), increased oncoprotein SET expression or increased cancerous inhibitor of protein phosphatase 2A (CIP2A) expression, comprising an above-described compound and a pharmacological acceptable carrier.

One embodiment of the present invention, the pharmaceutical composition further comprises an anti-cancer drug, and the anti-cancer drug is sorafenib or paclitaxel.

Another objective of the present invention is to provide a method of manufacturing a medicament including an above-described compound for treating a disease or condition characterized by inactive protein phosphatase 2A (PP2A), increased oncoprotein SET expression, increased cancerous inhibitor of protein phosphatase 2A (CIP2A) expression.

Another embodiment of the present invention, the disease or condition characterized by inactive protein phosphatase 2A (PP2A), increased oncoprotein SET expression, increased cancerous inhibitor of protein phosphatase 2A (CIP2A) expression is hepatocellular carcinoma, lung cancer, leukemia, breast cancer, renal cancer, thyroid cancer, colon cancer, head and neck cancer.

The detailed technology and above preferred embodiments implemented for the present invention are described in the following paragraphs accompanying the appended drawings for people skilled in this field to well appreciate the features of the claimed invention.

BRIEF DESCRIPTION OF THE DRAWINGS

FIG. 1A shows pro-apoptotic effects of TD-52 and erlotinib in HCC cells by MTT assay. $IC_{50}$ of TD-52 in different cells is illustrated. Points, mean; bars, S.D. (n=3). FIG. 1B shows dose-dependent effect of TD-52 and erlotinib on cell apoptosis in HCC cells by flowcytometry. Bar, mean; error bars, S.D. (n=3). FIG. 1C shows the proportion of apoptosis and necrosis of cancer cell by annexin-V/PI double-staining assay. FIG. 1D shows western blot for the expressions of caspases-3, caspases-9 and subsequent cleavage of poly (ADP-ribose) polymerase (PARP). FIG. 1E is DNA fragmentation test (n=6) after TD-52 treatment. FIG. 1F shows the pro-apoptotic effects induced by TD-52 is diminished by co-treatment with z-VAD-fmk, cells are analyzed by western blot (upper panel) and flow cytometry (lower panel). FIG. 1G shows that TD-52 exhibits little EGFR phosphorylation activity than erlotinib by western blotting.

FIG. 2A shows TD-52 downregulated CIP2A protein expression in HCC cells in a dose-dependent manner, HCC cells are treated with TD-52 at indicated concentration for 24 hr; cell lysates are subsequently collected for analysis of CIP2A, P-Akt, Akt protein expression by western blot. FIG. 2B shows TD-52 downregulated CIP2A protein expression in HCC cells in time-dependent manner, HCC cells are treated with 1 μM TD-52 at indicated duration; cell lysates are subsequently collected for analysis of CIP2A, P-Akt, Akt protein expression by western blot. FIG. 2C shows PP2A activities in HCC cells are enhanced after treating with TD-52, cell lysates are prepared for measuring PP2A phosphatase activity. Bar, mean; error bars, S.D. (n=3). FIG. 2D shows the effects of TD-52 on protein expression of PP2A, the expression of the subunits of PP2A are determined by western blot. FIG. 2E shows ectopic expression of CIP2A-myc abolishes effects of TD-52 on apoptosis in PLC5 cells, which is respectively analyzed by flow cytometry (right panel) and western blot (left panel). Bar, mean; error bars, S.D. (n=3). FIG. 2F shows that co-treatment with OA, a PP2A inhibitor, reduces the effect of TD-52 on apoptosis, which is respectively analyzed by flow cytometry (right panel) and western blot (left panel). Bar, mean; error bars, S.D. (n=3). FIG. 2G shows that downregulating PP2A-C by siRNA diminishes the pro-apoptotic effects of TD-52 in PLC5 cells, cell apoptosis is analyzed by flow cytometry (right panel) and expression of P-Akt, PP2A and PARP are analyzed by western blot (left panel). Bar, mean; error bars, S.D. (n=3). FIG. 2H shows ectopic expression of myc-tagged Akt1 abolishes the effects of TD-52 on apoptosis in PLC5 cells, which is respectively analyzed by flow cytometry (right panel) and western blot (left panel). Bar, mean; error bars, S.D. (n=3)

FIG. 3A show that TD-52 affects transcription of CIP2A in a dose- and time-dependent manner. PLC5 cells are treated with TD-52 at indicated doses (Left upper panel) and time (Left lower panel); CIP2A mRNA is quantified by reverse transcription-PCR. Bar, mean; error bars, S.D. (n=3), after treating cells with cycloheximide in the presence (Right lower panel) or absence (Right upper panel) of TD-52 for the indicated length of time, the expression of CIP2A protein in whole-cell lysates is assessed by western blot. FIG. 3B shows that identification of the CIP2A proximal promoter region that is affected by TD-52 (n=3, *P<0.05, Bar, mean; error bars, S.D. NS, nonsignificant). FIG. 3C shows that TD-52 inhibits the protein expression of transcriptional factor Elk-1 in nuclear and inhibits the protein expression of CIP2A in cytoplasm of PLC5 cells. PLC5 cells are lysed and whole-cell extract, the expression of CIP2A and Elk-1 are analyzed by western blot. Tubulin and lamin B were used as loading control. FIG. 3D shows that inhibition of the binding of Elk-1 to the CIP2A promoter determines the effect of TD-52 in PLC5 cells. ChIP assay is conducted to evaluate the binding ability of Elk-1 on the putative binding sites of CIP2A promoter region, PCR products are analyzed by gel-electrophoresis (Left panel). Right panel, Ectopic expression of Elk-1 reduced the pro-apoptotic effects of TD-52 in PLC5 cells (Right upper and Right lower panel). Bar, mean; error bars, S.D. (n=3)

FIG. 4A shows the growth curves of PLC5 xenograft tumor in TD-52-, sorafenib- and DMSO (vehicle)-treated nude mice. *P<0.05; Points, mean; bars, S.D. (n=6). FIG. 4B shows that the expression levels of CIP2A, p-Akt and Akt1 in PLC5 xenograft tumors are analyzed by western blot. FIG. 4C shows that analysis of PP2A activity of PLC5 xenograft tumor in TD-52- or DMSO (vehicle)-treated nude mice. *P<0.05; Bar, mean; error bars, S.D. (n=3). FIG. 4D shows that dose-dependent effects of sorafenib and TD-52 on cell viability in PLC5 cells. Bar, mean; error bars, S.D. (n=3).

FIG. 5A is representative image of immunohistochemical staining of SET in the HCC tumor tissue and paired adjacent normal tissue. FIG. 5B shows levels of SET expression in the tumor and non-tumor tissue of the clinical HCC samples. Bar: mean; error bar, S.D. (n=294). FIG. 5C shows expression ratio of tumor tissue to paired non-tumor tissue. Point: mean expression ratio of an individual patient (n=147); short bar, the average ratio of this cohort. FIG. 5D, Left panel is Representative image of immunohistochemical staining of SET and p-Akt in different patients. Right panel shows Recurrence-free survival from the time of HCC resection by co-expression of SET and p-Akt. FIG. 5E is representative image and quantitative analysis of the colony formation of PLC5 cells with and without knockdown of SET (n=6). FIG. 5F is representative image and quantitative analysis of the hepatosphere formation of Hep3B cells with and without knockdown of SET (n=6).

FIG. 6A shows that EMQA inhibits the viabilities of HCC cells by MTT assay. Points, mean; bars, S.D. (n=3). FIG. 6B shows that dose-dependent promotion of apoptosis of HCC treated with EMQA is analyzed by flowcytometry. Bar, mean; error bar, S.D. (n=3). FIG. 6C shows that dose-dependent promotion of apoptosis of HCC treated with EMQA is analyzed by DNA fragmentation test. Bar, mean; error bar, S.D. (n=3). FIG. 6D shows that EMQA induced downregulation of p-Akt and apoptosis of HCC cells in a time-dependent manner are analyzed by flowcytometry (upper panel) and western blot (lower panel). Bar, mean; error bar, S.D. (n=3) CF: cleaved form. FIG. 6E shows that growth curves of PLC5 xenograft tumors in EMQA- and vehicle-treated nude mice. Points, mean; bar, S.D. (n=10). FIG. 6F shows expression of p-Akt and Akt1 (left panel) and PP2A activity (right panel) in the PLC5 xenograft tumor lysate analyzed by western blot. Bar, mean; error bar, S.D. (n=10).

FIG. 7A shows that ectopic expression of Akt-myc abolishes the effects of EMQA on apoptosis in PLC5 cells, which is analyzed by flow cytoemetry and western blot. Bar, mean; error bars, S.D. (n=3). FIG. 7B shows that co-treatment with PP2A inhibitor, okadaic acid (OA), reduces the effects of EMQA on p-Akt and apoptosis, which is analyzed by flow cytometry and western blot. Bar, mean; error bars, S.D. (n=3). FIG. 7C shows that downregulating PP2Ac by siRNA diminishes the pro-apoptotic effects of EMQA in PLC5 cells, which is analyzed by flow cytometry and western blot. Bar, mean; error bars, S.D. (n=3). FIG. 7D shows that EMAQ downregulates p-Akt expression without affecting the expressions of PI3K, PTEN and PDK1, which is analyzed by western blot. FIG. 7E shows that ectopic expression of SET-myc abolishes the effects of EMQA on apoptosis in Hep3B cells, which is analyzed by flowcytometry and western blot. Bar, mean; error bars, S.D. (n=3). FIG. 7F shows that Sk-Hep1 cells are transfected with vectors coding full-length SET, the N-terminal fragment ($SET_{NTF}$, 1-227 a.a.) and the C-terminal ($SET_{CTF}$, 76-277 a.a) of SET protein to determine the SET antagonist effects of EMQA (left panel), which is analyzed by surface plasmon resonance (SPR, left panel) and co-immunoprecipitation (co-IP, right panel). Bar, mean; error bars, S.D. (n=3). Western blot analysis showed that EMQA significantly decreased the full-length SET-PP2Ac and SET-$_{CTF}$ binding, while the SET$_{NTF}$-PP2Ac association was not affected (right panel).

FIG. 8A shows that combination index of sorafenib and EMQA suggested synergy. Different HCC cell lines are exposed to a combination of sorafenib and EMQA and analyzed by MTT, the results are calculated by CalcuSyn software (Biosoft, Cambridge, U.K.). FIG. 8B shows that EMQA significantly improves the pro-apoptotic effects of sorafenib in HCC, which are analyzed by flow cytometry and western blot. FIG. 8C is the growth curve of tumors, which indicates that the combination treatment with EMQA and sorafenib significantly inhibit HCC tumor growth (n=10), Point, mean, *P<0.05. FIG. 8D is bar chart of tumor size, which indicates that the combination treatment with EMQA and sorafenib significantly inhibit HCC tumor growth. Bar, mean; error bar, S.D., *P<0.05). FIG. 8E shows PP2A activity of PLC5 xenograft tumor in vehicle and combination of EMQA and sorafenib therapy-treated nude mice Bar, mean; error bar, S.D. (n=10) (upper panel). The expression of p-Akt, Akt1 and SET in the PLC5 xenograft tumor lysate were analyzed by western blot (lower panel).

FIG. 9A shows EMQA and paclitaxel combination treatment induced downregulation of p-Akt, which is three different non-small-cell lung cancer (NSCLC) cell lines exposed to EMQA and/or paclitaxel are analyzed by western blot. FIG. 9B shows the time-dependent effects of EMQA and paclitaxel combination treatment on p-Akt and poly (ADP-ribose) polymerase (PARP) in A549 cells. FIG. 9C shows the dose-dependent effects of EMQA and paclitaxel combination treatment on p-Akt and PARP in A549 cells. FIG. 9D shows that ectopic expression of Akt-myc diminishes the effects of EMQA and paclitaxel combination treatment on apoptosis in A549 cells, which are analyzed by flow cyoemetry and western blot. Bar, mean; error bars, S.D. (n=3).

FIG. 10A shows the growth curves of A549 xenografted tumor in nude mice treated with vehicle, paclitaxel and/or EMQA. Points, mean, *P<0.05 (n=10 in each treatment arm). FIG. 10B shows the average tumor weight of resected A549 xenografted tumor after exposing to vehicle, paclitaxel and/or EMQA treatments. Bar, mean; error bar, S.D. FIG. 10C shows PP2A activity. Bar, mean; error bar, S.D. (n=3). FIG. 10D shows western blot image of the expression of p-Akt and Akt in A549 xenografted tumor lysate. FIG. 10E shows the changes of body weights of nude mice exposed to the indicated treatments. Points, mean.

DETAILED DESCRIPTION OF THE PREFERRED EMBODIMENT

Figure 1A:
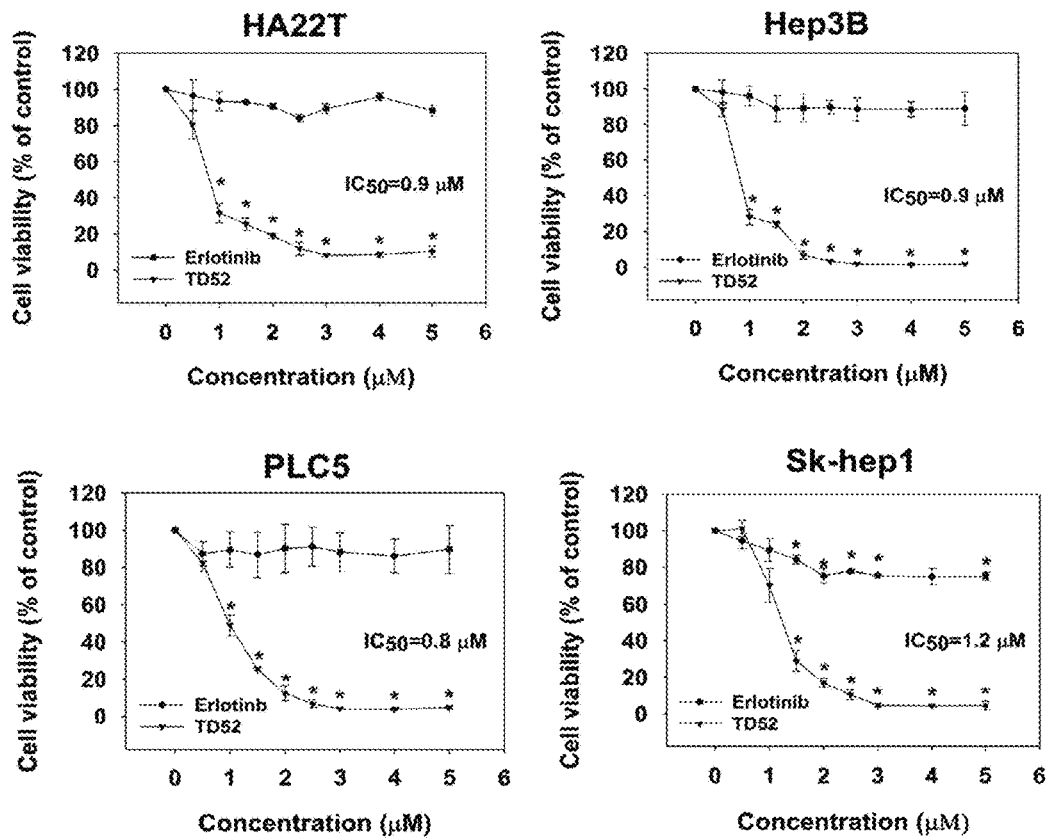
FIGS. 1A to 1G show that an erlotinib derivative of the present invention, TD-52, has a better pro-apoptotic effect of HCC cells than erlotinib.

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "EMQA" refers to the erlotinib derivatives, which comprise TD-52 to TD-95, ITRI TD-627, ITRI TD-602 to ITRI TD-605, ITRI TD-607, ITRI TD-608, ITRI TD-612 to ITRI TD-626, ITRI TD-628 to ITRI TD-631 and TD-632 compounds.

The term "carboxyl" denotes the group-C(O)OR, where R is hydrogen, lower alkyl, substituted lower alkyl, aryl, substituted aryl, and the like as defined herein.

The term "haloalkyl" denotes alkyl radical having one or more hydrogen atoms replaced by a halogen atom, which includes, but are not limited to trifluoromethyl.

The term "halogen" denotes fluorine, chlorine, bromine, iodine, and astatine.

The present invention is to explore erlotinib structure relationship with its bioactivity. The present invention is to develop erlotinib derivatives capable of SET antagonist, and which have a more potent therapeutic effect than traditional anti-cancer drugs, such as erlotinib, sorafenib and paclitaxel, the compounds of the present invention has a potent therapeutic effect on some disease, e.g. cancer. In the present invention, the novel compounds can be used as SET antagonist, and used for treating a disease or condition characterized by increased SET expression, such as hepatocellular carcinoma, lung cancer, leukemia, breast cancer, renal cancer, thyroid cancer, colon cancer, head or neck cancer. The compounds of the present invention can disrupt SET-PP2A binding to active PP2A, which leads to cancer cell apoptotic effect. Therefore, the compounds of the present invention provides an alternative cancer therapy by the new target mechanism, which is very helpful to the patients resistant to traditional medicine In one aspect, the present invention provides an aryl amine substituted quinoxaline which is represented by Formula I(a) or Formula I(b)

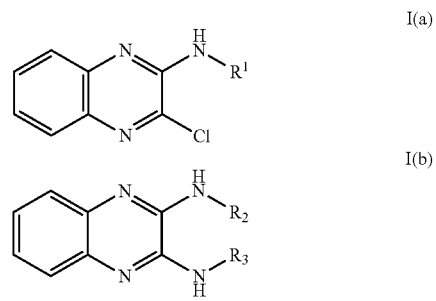

wherein $R^1$, $R^2$ and $R^3$ are same or different substituted phenyl groups and are independently phenyl substituted with an atom or group, aromatic heterocyclic group, and the substituted phenyl group each is

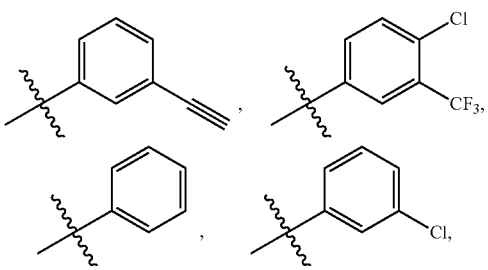

-continued
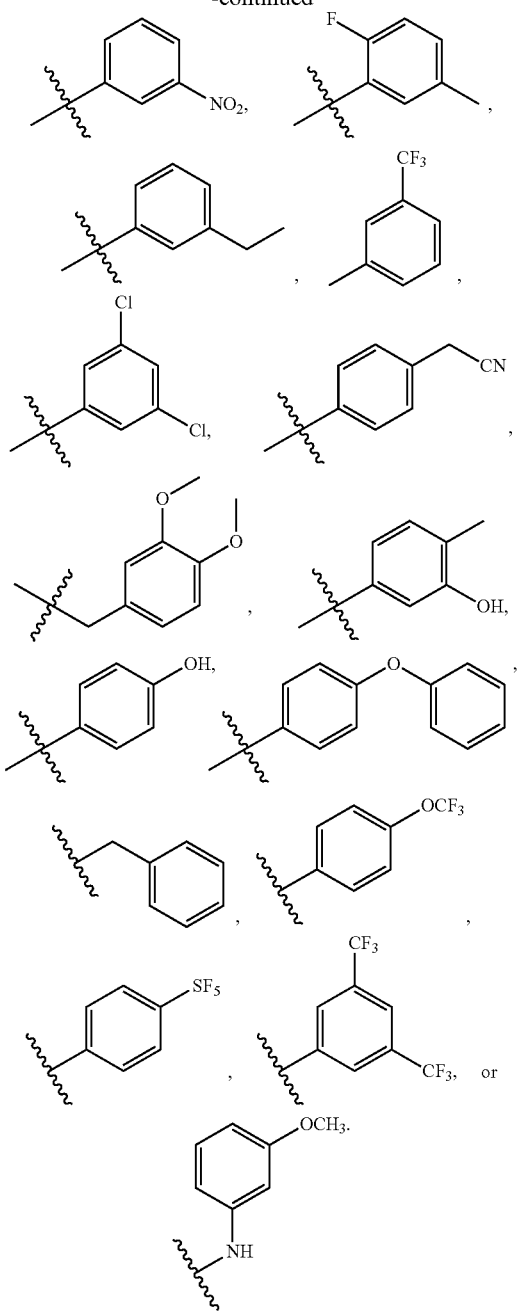
In one embodiment, the compound of Formula I(a) is included one of the compounds as listed in Table 1, but not limited to, TD-70 to TD-82.
TABLE 1
| No. | R¹ |
|---|---|
| TD-52 | 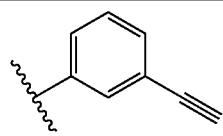 |
| TD-53 | 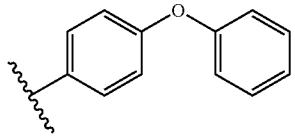 [SMILES: *c1ccc(Oc2ccccc2)cc1] |
| TD-54 | 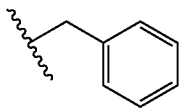 [SMILES: *Cc1ccccc1] |
| TD-55 | 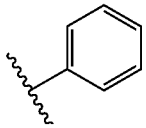 |
| TD-56 | 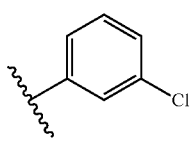 [SMILES: *c1cccc(Cl)c1] |
| TD-57 | 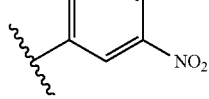 |
| TD-58 | 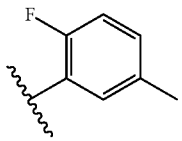 [SMILES: *c1cc(C)ccc1F] |
| TD-59 | 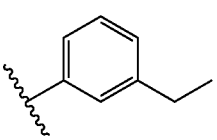 [SMILES: *c1cccc(CC)c1] |
| TD-60 | 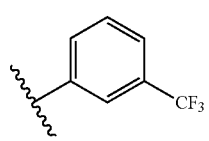 [SMILES: *c1cccc(C(F)(F)F)c1] |
| TD-61 | 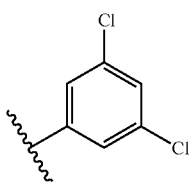 [SMILES: *c1cc(Cl)cc(Cl)c1] |
| TD-62 | 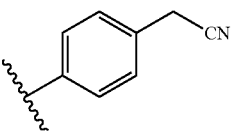 [SMILES: *c1ccc(CC#N)cc1] |

TABLE 1-continued

The compound of Formula I(a)

| No. | R¹ |
|---|---|
| TD-63 | 4-Cl, 3-CF₃-phenyl |
| TD-64 | 3,4-dimethoxybenzyl |
| TD-65 | 4-OCF₃-phenyl |
| TD-66 | 4-methyl-3-hydroxyphenyl |
| TD-67 | 4-hydroxyphenyl |
| TD-68 | 4-SF₅-phenyl |
| TD-69 | 3,5-bis(CF₃)phenyl |
| ITRI TD-627 | 3-OCH₃-phenyl-NH- |

In one embodiment, the compound of Formula I(b) is include one of the compounds as listed in Table 2, but not limited to, TD-52 to TD-69 and ITRI TD-627.

TABLE 2

The compound of Formula I(b)

| No. | R²/R³ |
|---|---|
| TD-70 | 3-ethynylphenyl |
| TD-71 | 4-phenoxyphenyl |
| TD-72 | benzyl |
| TD-73 | phenyl |
| TD-74 | 3-Cl-phenyl |
| TD-75 | 3-NO₂-phenyl |
| TD-76 | 3-ethylphenyl |
| TD-77 | 3-CF₃-phenyl |
| TD-78 | 3,5-dichlorophenyl |
| TD-79 | 4-Cl, 3-CF₃-phenyl |

TABLE 2-continued

The compound of Formula I(b)

| No. | R²/R³ |
|---|---|
| TD-80 | 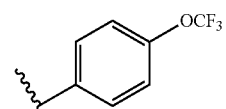 |
| TD-81 | 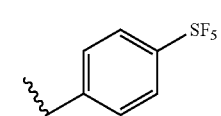 |
| TD-82 | 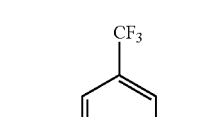 |

In another aspect, the present invention provides an aryl amine substituted quinoxaline which is represented by Formula I(c)

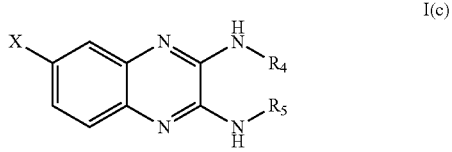

wherein R⁴ and R⁵ are same or different substituted phenyl groups and are independently phenyl substituted with an atom or group, aromatic heterocyclic group, and the substituted phenyl group each is

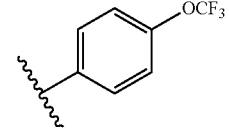

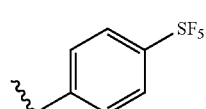

wherein X is halogen, haloalkyl, methoxy, nitro, amino, amido, carboxyl, acid, benzophenone or methoxycarbonyl.

In one embodiment, the compound of Formula I(c) is included one of the compounds as listed in Table 3, but not limited to, TD-83 to TD-95, ITRI TD-602 to ITRI TD-604, ITRI TD-607 to ITRI TD-608, ITRI TD-613 to ITRI TD-618, ITRI TD-620 to ITRI TD-624 and ITRI TD-629.

TABLE 3

The compound of Formula I(c)

| No. | X | R⁴/R⁵ |
|---|---|---|
| TD-83 | F | 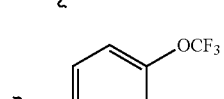 |
| TD-84 | F | |
| TD-85 | Cl | |
| TD-86 | Cl | 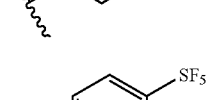 |

TABLE 3-continued

The compound of Formula I(c)

| No. | X | R⁴/R⁵ |
|---|---|---|
| TD-87 | CF₃ | 4-OCF₃-phenyl |
| TD-88 | CF₃ | 4-SF₅-phenyl |
| TD-89 | OCH₃ | 4-OCF₃-phenyl |
| TD-90 | OCH₃ | 4-SF₅-phenyl |
| TD-91 | NO₂ | 4-Cl-3-CF₃-phenyl |
| TD-92 | NO₂ | 4-OCF₃-phenyl |
| TD-93 | NO₂ | 4-SF₅-phenyl |
| ITRI TD-602 | NO₂ | 4-OCH₃-phenyl |
| ITRI TD-603 | NO₂ | 4-CF₃-phenyl |
| ITRI TD-604 | NO₂ | 3-ethynyl-phenyl |
| ITRI TD-608 | NO₂ | 3-OCH₃-phenyl |
| ITRI TD-613 | NO₂ | 3-OH-phenyl |
| ITRI TD-615 | NO₂ | 3-CF₃-phenyl |
| ITRI TD-616 | NO₂ | 4-OH-phenyl |
| ITRI TD-617 | NO₂ | 4-COOH-phenyl |
| ITRI TD-618 | NO₂ | 3-Br-phenyl |
| ITRI TD-620 | NO₂ | 4-F-phenyl |
| ITRI TD-621 | NO₂ | 4-F-2-methyl-phenyl |
| ITRI TD-623 | NO₂ | 4-CH₂OH-phenyl |
| ITRI TD-624 | NO₂ | 4-Cl-3-F-phenyl |

TABLE 3-continued

The compound of Formula I(c)

| No. | X | R⁴/R⁵ |
|---|---|---|
| ITRI TD-629 | NO₂ | (4-sulfamoylphenyl) |
| ITRI TD-607 | NH₂ | (4-trifluoromethylphenyl) |
| ITRI TD-614 | NH₂ | (3-ethynylphenyl) |
| ITRI TD-622 | NH₂ | (2-methyl-4-fluorophenyl) |
| TD-94 | COOCH₃ | (4-trifluoromethoxyphenyl) |
| TD-95 | COOCH₃ | (4-pentafluorosulfanylphenyl) |

In another aspect, the present invention provides an aryl amine substituted quinoxaline which is represented by Formula I(d)

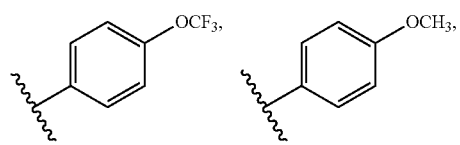

wherein R⁶ and R⁷ are same or different substituted phenyl groups and are independently phenyl substituted with an atom or group, aromatic heterocyclic group, and the substituted phenyl group each is

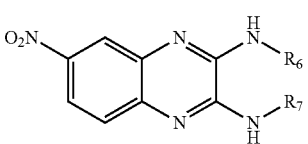

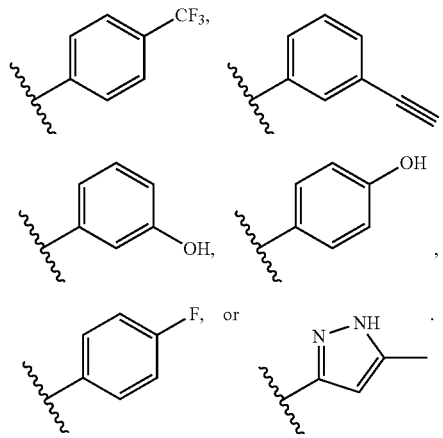

In one embodiment, the compound of Formula I(d) is included one of the compounds as listed in Table 4, but not limited to, ITRI TD-605, ITRI TD-612, ITRI TD-619, ITRI TD-625, ITRI TD-626, ITRI TD-628, ITRI TD-630, ITRI TD-631.

TABLE 4

The compound of Formula I(d)

| No. | R⁶ | R⁷ |
|---|---|---|
| ITRI TD-605 | (3-ethynylphenyl) | (4-methoxyphenyl) |
| ITRI TD-612 | (3-hydroxyphenyl) | (4-methoxyphenyl) |
| ITRI TD-619 | (3-ethynylphenyl) | (4-hydroxyphenyl) |
| ITRI TD-625 | (3-ethynylphenyl) | (3-methyl-4-hydroxyphenyl) |
| ITRI TD-626 | (4-trifluoromethylphenyl) | (4-methoxyphenyl) |
| ITRI TD-628 | (4-hydroxyphenyl) | (5-methyl-4,5-dihydro-1H-pyrazol-3-yl) |

TABLE 4-continued

The compound of Formula I(d)

| No. | $R^6$ | $R^7$ |
|---|---|---|
| ITRI TD-630 | 4-OCF3-phenyl | 4-OCH3-phenyl |
| ITRI TD-631 | 4-F-phenyl | 4-OCH3-phenyl |

In another aspect, the present invention provides an aryl amine substituted quinoxaline which is represented by Formula II

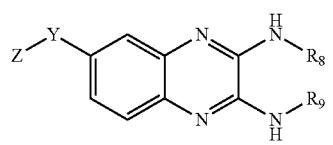

II wherein $R^8$ and $R^9$ are same or different substituted phenyl groups and are independently phenyl substituted with an atom or group, and the substituted phenyl group each is

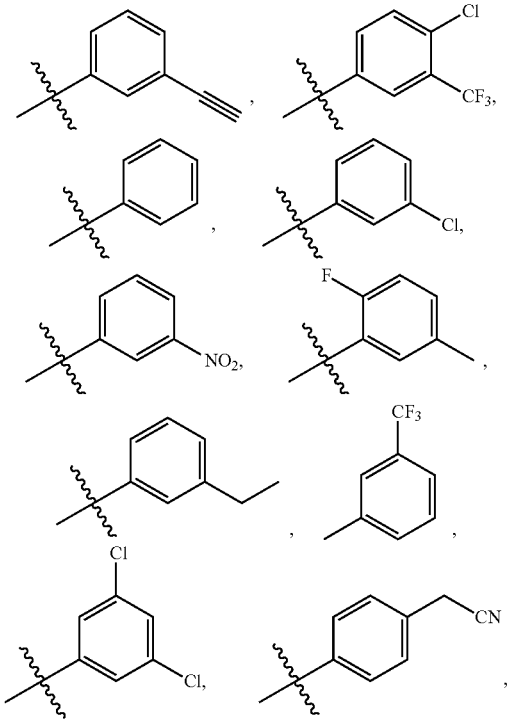

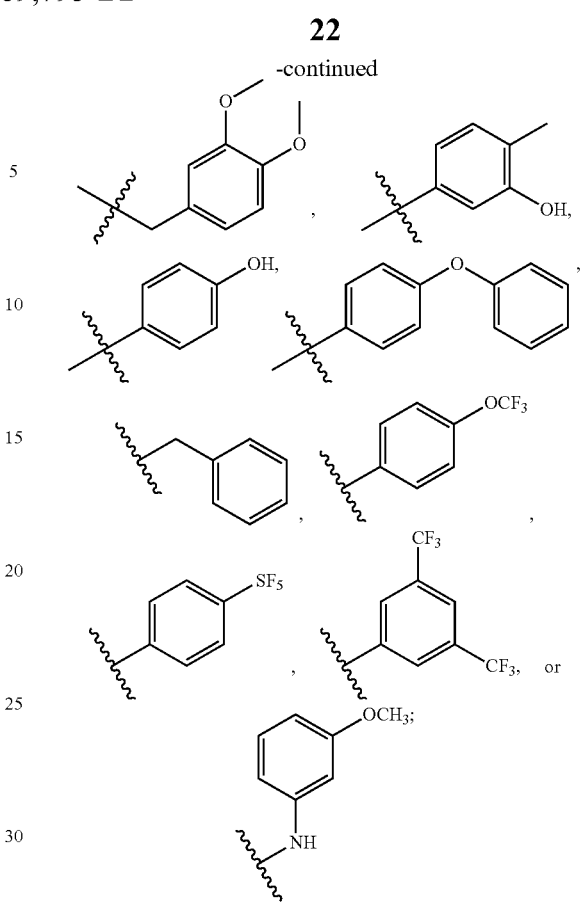

and wherein Y is CO or $(CH_2)_n$, n=1-3; Z=COOR$^{10}$, or a phenyl substituted with a functional group, $R^{10}$ is aryl or alkyl.

In one embodiment, the compound of Formula II is as shown in the following:

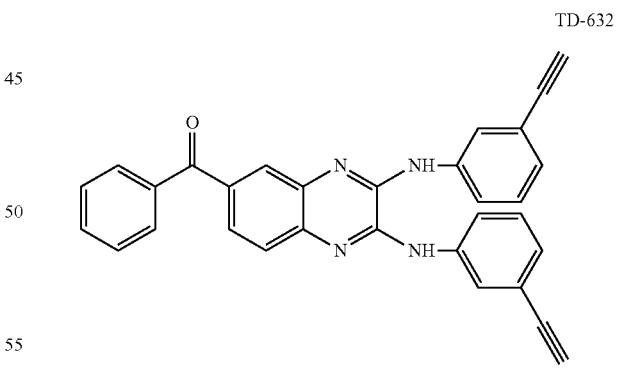

TD-632

The compounds of the present invention thus synthesized can be further purified by chromatography or crystallization or any other prior method known in the art.

The present invention provides a pharmaceutical composition comprising one or more of the above-described compounds and a pharmacological acceptable carrier. The pharmaceutical composition of the present invention may be used for disrupting the binding between protein phosphatase 2A (PP2A) and oncoprotein SET to increase biological activity of PP2A in a cell, or for treating a disease or condition characterized by inactive PP2A or CIP2A and SEP overexpression. In addition, also within the scope of this invention is the use of any of the above-described compounds for activating PP2A in a cell or oncoprotein SET antagonist, or treating a disease or condition characterized by inactive PP2A or SET overexpression as described herein and for manufacture of a medicament for treating the same.

The present invention also provides a method for increasing PP2A or decreasing oncoprotein SET expression level or biological activity in a cell, comprising contacting the cell with an effective amount of a compound or a pharmaceutical composition as described herein. The present invention further provides a method for treating a disease or condition characterized by inactive PP2A or SET overexpression in a subject in need thereof, comprising administrating to the subject an effective amount of a compound or a pharmaceutical composition as described herein.

The compounds of the present invention can be used for the treatment of diseases or conditions characterized by inactive PP2A or oncoprotein SET overexpression. A compound of the present invention can be administrated to a human patient by itself or in pharmaceutical compositions where it is mixed with suitable carriers or excipients at doses to treat or ameliorate various conditions characterized by decreasing PP2A expression or oncoprotein SET overexpression. Increased or decreased expression levels or biological activity of a factor (e.g. PP2A) can be readily detected by the gene product of the factor such as a protein or RNA, in a sample from a subject (e.g. from blood or biopsy tissue) and assaying it in vitro for RNA levels, structure and/or activity of the expressed proteins and the like, using detection methods known in art such as enzyme-linked immunosorbent assay (ELISA), western blotting and northern blotting. Particular examples of the disease or conditions characterized by inactive PP2A, or oncoprotein SET and CIP2A overexpression according to the invention includes, but not limited to, cancer (e.g. hepatocellular carcinoma, leukemia, lung cancer, breast cancer, renal cancer) and osteoporosis.

The term "treatment" includes prophylaxis of the specific disorder or condition, or alleviation of the symptoms associated with a specific disorder or condition and/or preventing or eliminating said symptoms.

A "subject" is particularly a mammal, such as a human, but can also be a companion animal (e.g., dogs, cats, and the like), farm animals (e.g., cows, sheep, pigs, horses, and the like) or laboratory animals (e.g., rats, mice, guinea pigs, and the like) in need of the treatment as described herein.

"An effective amount" as used herein refers to the amount of an active agent required to confer therapeutic effects on a subject, either alone or in combination with one or more other active agents. Effective amounts vary, as recognized by those skilled in the art, depending on route of administration, excipient usage, and co-usage with other active agents.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

The pharmaceutical compositions of the present invention may be manufactured in a manner known in the art, e.g., by means of conventional mixing, dissolving, emulsifying, encapsulating, entrapping, or lyophilizing processes. Pharmaceutical compositions for use in accordance with the present invention thus may be formulated in conventional manner using one or more physiologically acceptable carriers comprising excipients and/or auxiliaries that facilitate processing of the active compounds into preparations, which can be used pharmaceutically. As used herein, "acceptable" means that the carrier must be compatible with the active ingredient of the composition (and preferably, capable of stabilizing the active ingredient) and not deleterious to the subject to be treated. Proper formulation is dependent upon the route of administration chosen.

In particular, for injection, the compounds of the invention may be formulated in, for example, physiologically compatible buffers, such as Hank's solution, Ringer's solution, or physiological saline buffer. For oral administration, the compounds of the invention may be formulated by combining the active compounds with pharmaceutically acceptable carriers known in this art, such as lactose, sucrose, mannitol, sorbitol, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), to enable the compounds of the invention to be formulated as tablets, pills, dragees, capsules, liquids, gels, syrups, slurries, suspensions and the like. For administration by inhalation, the compounds of the invention can be formulated in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas.

EXAMPLE 1

Chemical Synthesis

Particularly, the procedure shown in the scheme I to V as below exemplifies synthesis of certain compounds of invention.

1.1 Synthetic Scheme I

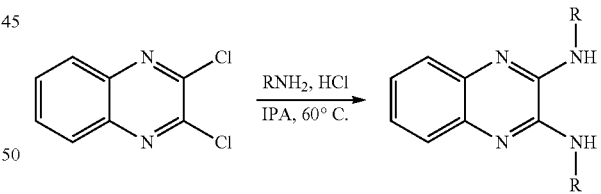

The compounds of the present invention can be obtained from above Synthetic Scheme I, the detailed synthetic scheme is described below. In Synthetic Scheme I, 2,3-dicholoroquinoxaline (1 equiv) and phenylamine analogues (2.3 equiv) were added in isopropyl alcohol (3 to 5 ml), followed by 2 drops of concentrated HCl. The mixture was then heated to 60° C. overnight and was expected to yield white or yellow solid. After the reaction was completed, the reaction mixture was filtered, and the solid was washed by isopropyl alcohol to give di-substituted quinoxaline derivatives, which would be further purified by normal phase chromatography using ethyl acetate/hexane as eluent to give TD-52 to TD69 and ITRI TD-627 compounds.

1.1.1 N²,N³-bis(3-ethynylphenyl)quinoxaline-2,3-diamine (TD-52)

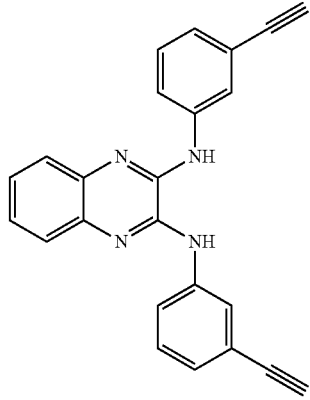

TD-52

¹H NMR (400 MHz, MeOH-d₄) δ 3.47 (s, 1H) 7.16 (d, J=7.6 Hz, 1H), 7.29-7.33 (m, 2H), 7.56 (dd, J=3.4, 6.4 Hz, 1H), 7.84 (dd, J=8.0, 1.2 Hz, 1H), 7.96 (s, 1H).

1.1.2 N²,N³-bis(4-phenoxyphenyl)quinoxaline-2,3-diamine (TD-53)

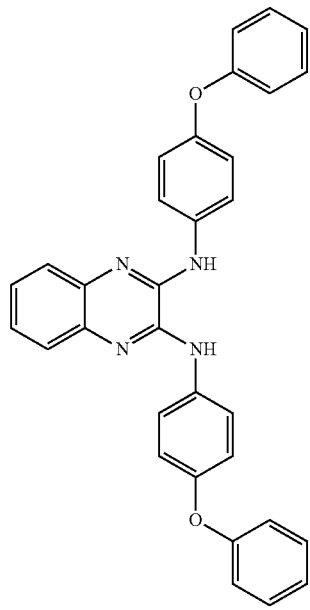

TD-53

¹H NMR (400 MHz, DMSO-d₆) δ 7.02 (d, J=7.6 Hz, 2H), 7.08-7.13 (m, 3H), 7.32 (s, 1H), 7.38 (t, J=7.2 Hz, 2H), 7.53 (s, 1H), 7.92 (d, J=8.4 Hz, 2H).

1.1.3 N²,N³-dibenzylquinoxaline-2,3-diamine (TD-54)

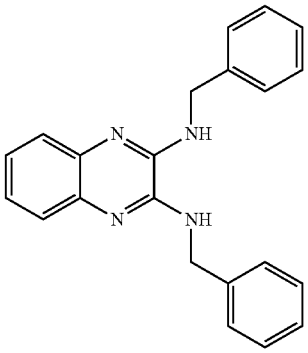

TD-54

¹H NMR (400 MHz, MeOH-d₄) δ 4.72 (s, 2H), 7.18-7.24 (m, 2H), 7.29 (t, J=7.2 Hz, 2H), 7.38 (d, J=7.2 Hz, 2H), 7.52 (dd, J=3.4, 6.4 Hz, 1H).

1.1.4 N²,N³-diphenylquinoxaline-2,3-diamine (TD-55)

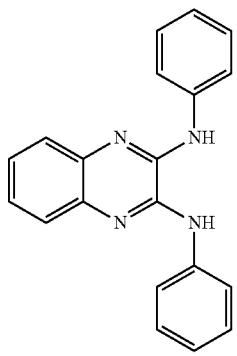

TD-55

¹H NMR (400 MHz, MeOH-d₄) δ 7.10 (t, J=7.6 Hz, 1H), 7.34 (dd, J=3.4, 6.4 Hz, 1H), 7.39 (t, J=7.6 Hz, 2H), 7.58 (dd, J=3.4, 6.4 Hz, 1H), 7.83 (d, J=8.0 Hz, 2H).

1.1.5 N²,N³-bis(3-chlorophenyl)quinoxaline-2,3-diamine (TD-56)

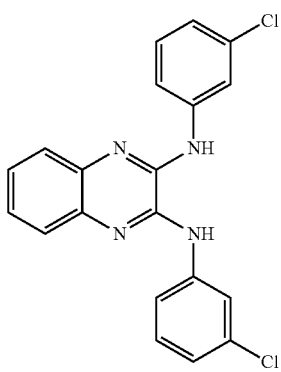

TD-56

¹H NMR (400 MHz, DMSO-d₆) δ 7.14 (d, J=8.0 Hz, 1H), 7.38-7.43 (m, 2H), 7.60 (dd, J=3.2, 6.0 Hz, 1H), 8.02 (d, J=8.4 Hz, 1H), 8.24 (s, 1H).

1.1.6 N²,N³-bis(2-fluoro-5-methylphenyl)quinoxaline-2,3-diamine (TD-58)

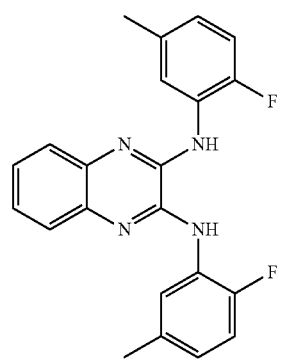
TD-58

¹H NMR (400 MHz, MeOH-d₄) δ 2.42 (s, 3H), 7.23 (s, 1H), 7.25 (d, J=1.2 Hz, 1H), 7.43 (dd, J=3.4, 6.4 Hz, 1H), 7.51 (d, J=7.2 Hz, 1H), 7.61 (dd, J=3.4, 6.4 Hz, 1H).

1.1.7 N²,N³-bis(3-ethylphenyl)quinoxaline-2,3-diamine (TD-59)

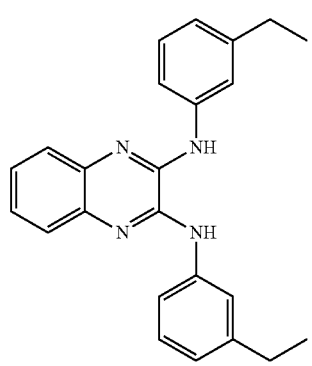
TD-59

¹H NMR (400 MHz, MeOH-d₄) δ 1.23 (t, J=7.6 Hz, 3H), 2.61 (q, J=7.6 Hz, 2H), 6.86 (d, J=7.6 Hz, 1H), 7.21 (t, J=7.6 Hz, 1H), 7.26 (s, 1H), 7.54-7.56 (m, 2H), 7.62 (d, J=7.6 Hz, 1H).

1.1.8 N²,N³-bis(3-(trifluoromethyl)phenyl)quinoxaline-2,3-diamine (TD-60)

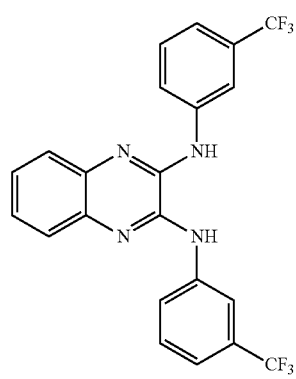
TD-60

¹H NMR (400 MHz, DMSO-d₆) δ 7.40 (t, J=8.0 Hz, 2H), 7.58 (dd, J=3.6, 5.6 Hz, 1H), 7.62 (t, J=8.0 Hz, 1H), 8.19 (d, J=8.0 Hz, 1H), 8.34 (s, 1H), 9.33 (s, 1H).

1.1.9 2,2'-((quinoxaline-2,3-diylbis(azanediyl))bis(4,1-phenylene))diacetonitrile (TD-62)

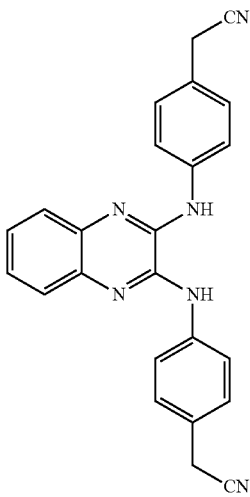
TD-62

¹H NMR (400 MHz, DMSO-d₆) δ 4.03 (s, 2H), 7.35-7.39 (m, 3H), 7.58 (dd, J=3.4, 6.4 Hz, 1H), 7.99 (d, J=8.8 Hz, 2H).

1.1.10 N²,N³-bis(4-chloro-3-(trifluoromethyl)phenyl)quinoxaline-2,3-diamine (TD-63)

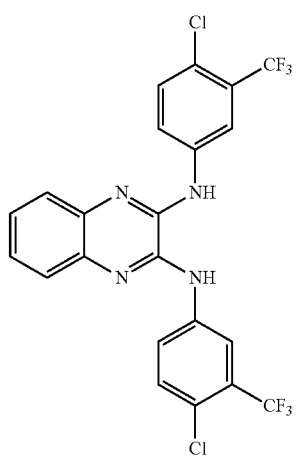
TD-63

¹H NMR (400 MHz, MeOH-d₄) δ 7.28 (dd, J=3.6, 6.0 Hz, 1H), 7.45 (d, J=8.8 Hz, 1H), 7.48 (dd, J=3.4, 6.4 Hz, 1H), 8.03 (dd, J=8.8, 2.4 Hz, 1H), 8.34 (d, J=2.4 Hz, 1H).

1.1.11 N²,N³-bis(4-(trifluoromethoxy)phenyl)quinoxaline-2,3-diamine (TD-65)

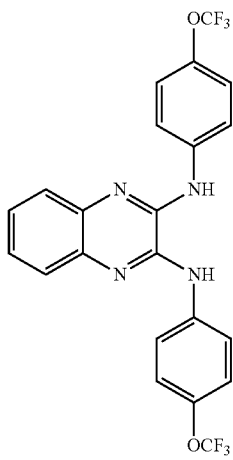
TD-65

¹H NMR (400 MHz, MeOH-d₄) □ 7.26 (d, J=8.4 Hz, 2H), 7.32 (dd, J=3.2, 6.0 Hz, 1H), 7.57 (dd, J=3.2, 6.0 Hz, 1H), 7.90 (d, J=9.2 Hz, 2H).

1.1.12 5,5'-(quinoxaline-2,3-diylbis(azanediyl))bis(2-methylphenol)(TD-66)

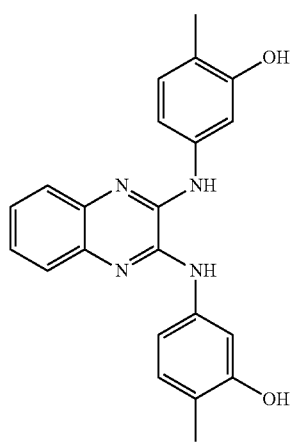
TD-66

¹H NMR (400 MHz, MeOH-d₄) □ 2.24 (s, 3H), 7.03 (dd, J=8.0, 2.0 Hz, 1H), 7.21 (d, J=8.0 Hz, 1H), 7.26 (s, 1H), 7.44 (dd, J=3.4, 6.0 Hz, 1H), 7.67 (dd, J=3.4, 6.0 Hz, 1H).

1.1.13 N²,N³-bis(4-(Pentafluorothio)phenyl)quinoxaline-2,3-diamine (TD-68)

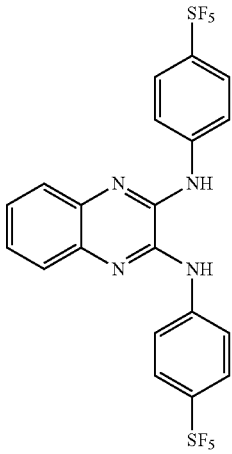
TD-68

¹H NMR (400 MHz, MeOH-d₄) □ 7.41 (dd, J=3.6, 6.0 Hz, 1H), 7.67 (dd, J=3.4, 6.4 Hz, 1H), 7.79 (d, J=9.2 Hz, 2H), 8.03 (d, J=8.8 Hz, 2H).

1.2 Synthetic Scheme II

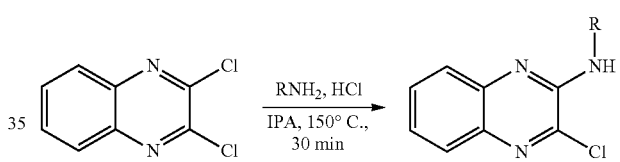

The compounds of the present invention can be obtained from above Synthetic Scheme II, the detailed synthetic scheme is described below. In Synthetic Scheme II, 2,3-dicholoroquinoxaline (1 equiv) and phenylamine analogues (1 equiv) were added in isopropyl alcohol (3 to 5 ml), followed by a drop of concentrated HCl. The mixture was then heated to 150° C. for 30 minutes by microwave machine. After the reaction was completed, the reaction mixture was filtered by IPA to yield white solid, which was washed by ether or ethyl acetate to give mono-substituted quinoxaline derivatives TD-70 to TD-82 compounds.

1.2.1 3-chloro-N-(3,5-dichlorophenyl)quinoxalin-2-amine (TD-78)

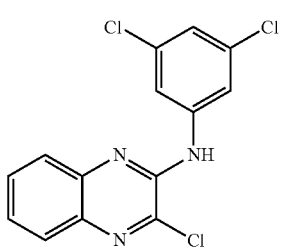
TD-78

¹H NMR (400 MHz, DMSO-d₆) □□7.20-7.28 (m, 4H), 7.52 (d, J=8.0 Hz, 1H), 8.35 (s, 2H), 9.82 (s, 1H).

1.2.2 3-chloro-N-(4-chloro-3-(trifluoromethyl)phenyl)quinoxalin-2-amine (TD-79)

TD-79

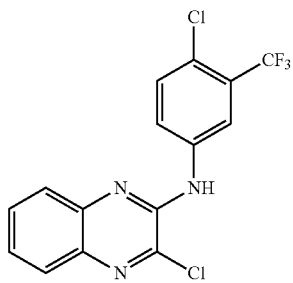

$^1$H NMR (400 MHz, DMSO-d$_6$) □□7.21-7.26 (m, 3H), 7.47 (d, J=8.0 Hz, 1H), 7.64 (d, J=8.8 Hz, 1H), 8.47 (d, J=8.8 Hz, 1H), 8.89 (s, 1H), 9.97 (s, 1H).

1.2.3 3-chloro-N-(4-(trifluoromethoxy)phenyl)quinoxalin-2-amine (TD-80)

TD-80

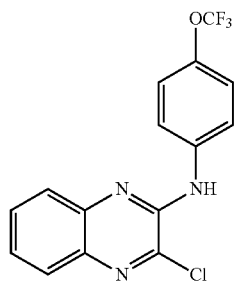

$^1$H NMR (400 MHz, DMSO-d$_6$) □□7.19-7.20 (m, 3H), 7.34 (d, J=8.4 Hz, 2H), 7.50 (d, J=7.6 Hz, 1H), 8.28 (d, J=8.4 Hz, 2H), 9.65 (s, 1H).

1.2.4 3-chloro-N-(4-(Pentafluorothio)phenyl)quinoxalin-2-amine (TD-81)

TD-81

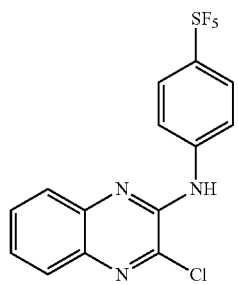

$^1$H NMR (400 MHz, DMSO-d$_6$) □□7.22-7.27 (m, 3H), 7.54 (d, J=7.6 Hz, 1H), 7.84 (d, J=8.4 Hz, 2H), 8.38 (d, J=8.8 Hz, 2H), 9.90 (s, 1H).

1.3 Synthetic Scheme III

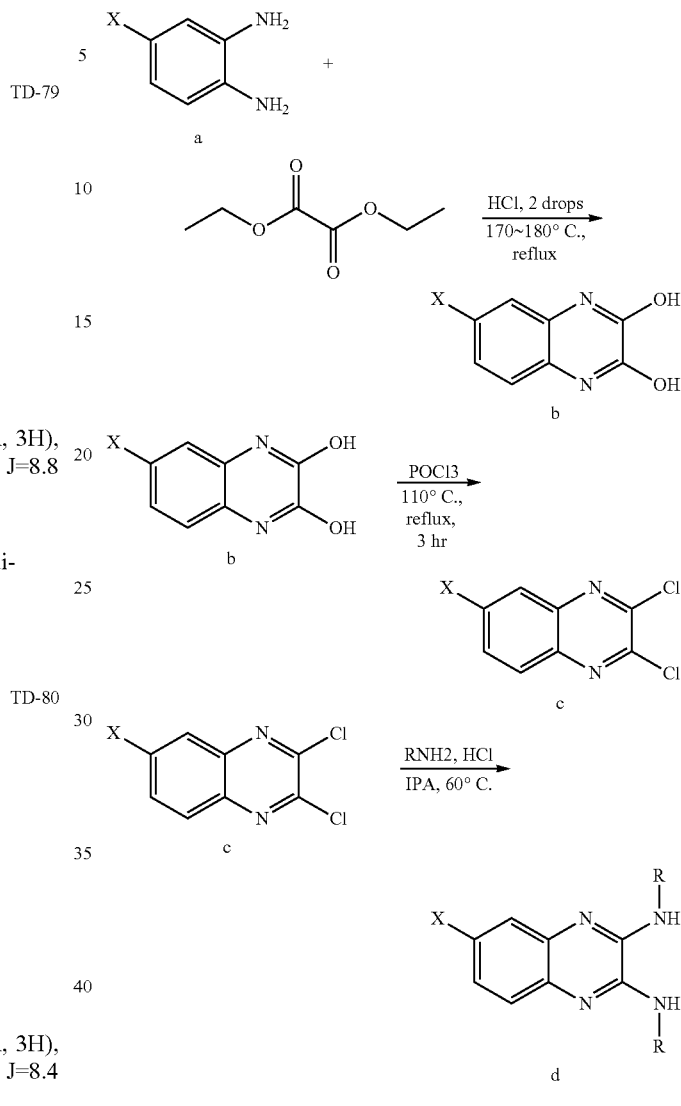

The compounds of the present invention can be obtained from above Synthetic Scheme III, the detailed synthetic scheme is described below. In Synthetic Scheme III, Phenylenediamine with modification at 4 positions (a) was dissolved in diethyloxalate with 2 ml of concentrated HCl and heated to 180° C. overnight. The mixture was filtered by water and dried to obtain the precipitate intermediate b. Intermediate b was then dissolved in POCl$_3$ and heated to 110° C. for 3 hr. After the reactant mixture was cooled down to room temperature, the mixture was poured into ice-water, resulting in the precipitation of the product, which was dried in oven to obtain intermediate c. Phenylamines and intermediate c were dissolved in IPA, followed by 2 drops of concentrated HCl and then heated to 60° C. overnight. The mixture was filtered by IPA and the precipitates was further purified by chromatography to give TD-83 to TD-95, ITRI TD-602 to ITRI TD-604, ITRI TD-607, ITRI TD-608. ITRI TD-613 to ITRI TD-618, ITRI TD-620 to ITRI TD-624, ITRI TD-629.

1.3.1 methyl 2,3-bis((4-(trifluoromethoxy)phenyl)amino)quinoxaline-6-carboxylate (TD-94)

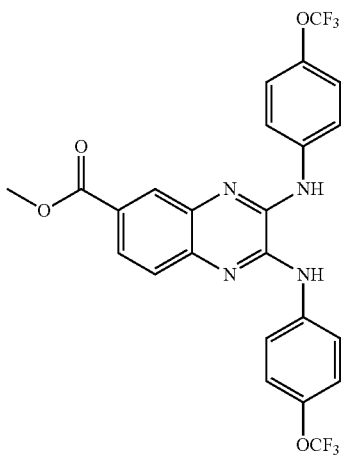
TD-94

¹H NMR (400 MHz, DMSO-d₆) ☐☐3.84 (s, 3H), 7.38 (dd, J=4.4, 8.0 Hz, 4H), 7.56 (d, J=8.4 Hz, 1H), 7.83 (dd, J=8.6, 1.6 Hz, 1H), 8.10 (d, J=1.2 Hz, 1H), 8.18 (t, J=8.8 Hz, 4H).

1.3.2 N²,N³-bis(4-methoxyphenyl)-6-nitroquinoxaline-2,3-diamine (ITRI TD-602)

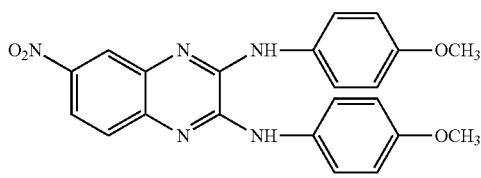

¹H NMR (500 MHz, DMSO-d6) ☐☐☐3.79 (s, 6H), 7.00 (dd, 4H), 7.56 (d, 1H), 7.89 (dd, 4H), 8.03 (d, 1H), 8.23 (s, 1H), 10.0 (b, 2H).

1.3.3 N²,N³-bis(3-ethynylphenyl)-6-nitroquinoxaline-2,3-diamine (ITRI TD-604)

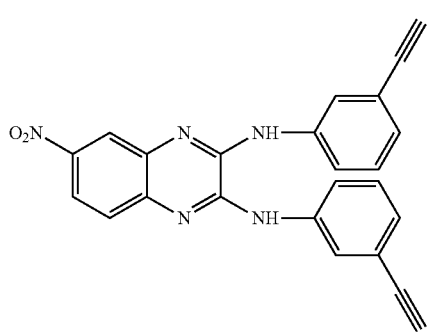

¹H NMR (500 MHz, DMSO-d6) ☐☐☐4.19 (s, 1H), 4.20 (s, 1H) 7.23 (dd, 2H), 7.42 (m, 3H), 7.64 (d, 1H), 8.11 (b, 4H), 8.23 (s, 1H), 10.1 (b, 2H).

1.3.4 N²,N³-bis(4-(trifluoromethyl)phenyl)quinoxaline-2,3,6-triamine (ITRI TD-607)

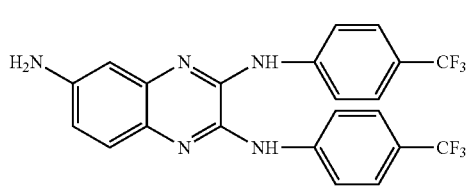

¹H NMR (500 MHz, DMSO-d6) ☐☐☐ 7.71 (d, 1H), 7.77 (m, H), 8.1 (m, 5H), 9.66 (s, 1H), 9.80 (s, 1H).

1.3.5 N²,N³-bis(3-methoxyphenyl)-6-nitroquinoxaline-2,3-diamine (ITRI TD-608)

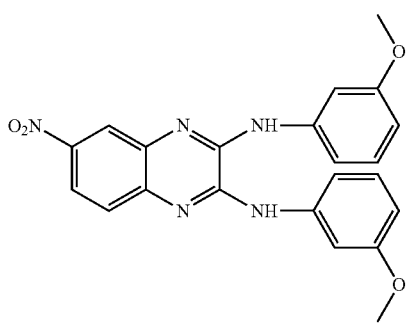

¹H NMR (500 MHz, DMSO-d6) ☐☐☐☐3.98 (s, 3H), 3.97 (s, 3H), 6.68 (dd, 2H), 7.27 (t, 2H), 7.43 (d, 1H), 7.44 (d, 1H), 7.61 (s, 1H), 7.62 (m, 2H), 8.05 (d, 1H), 8.25 (s, 1H), 9.28 (s, 1H), 9.35 (s, 1H).

1.3.6 3-(2-(3-hydroxyphenylamino)-6-nitroquinoxalin-3-ylamino)phenol (ITRI TD-613)

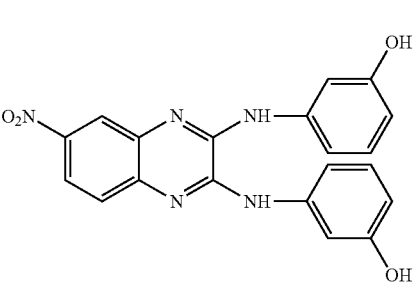

¹H NMR (500 MHz, DMSO-d6) ☐☐☐☐6.68 (dd, 2H), 7.09 (m, 2H), 7.18 (m, 2H), 7.58 (d, 1H), 7.61 (d, 1H), 7.70 (d, 1H), 8.10 (d, 1H), 8.31 (s, 1H), 9.60-10.1 (b, 4H).

1.3.7 $N^2,N^3$-bis(3-bromophenyl)-6-nitroquinoxaline-2,3-diamine (ITRI TD-618)

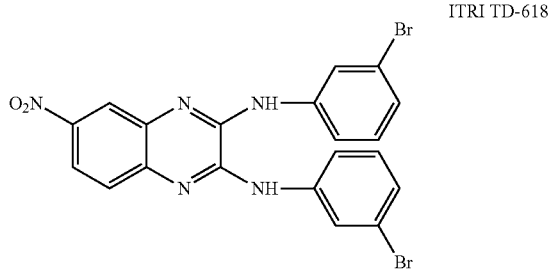 [SMILES: O=[N+]([O-])c1ccc2nc(Nc3cccc(Br)c3)c(Nc3cccc(Br)c3)nc2c1]

ITRI TD-618

$^1$H NMR (500 MHz, DMSO-d6) ▢▢▢▢7.00 (dd, 1H), 7.19 (m, 2H), 7.30 (m, 1H), 7.58 (d, 1H), 7.39 (dd, 2H), 7.62 (d, 1H), 8.05 (m, 3H), 8.38 (s, 1H), 10.2-10.6 (b, 2H).

1.3.8 $N^2,N^3$-bis(4-fluorophenyl)-6-nitroquinoxaline-2,3-diamine (ITRI TD-620)

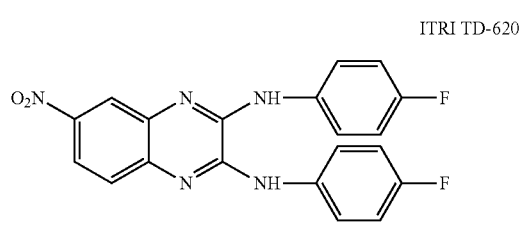 [SMILES: O=[N+]([O-])c1ccc2nc(Nc3ccc(F)cc3)c(Nc3ccc(F)cc3)nc2c1]

ITRI TD-620

$^1$H NMR (500 MHz, DMSO-d6) δ 7.25 (m, 4H), 7.59 (d, 1H), 7.88 (m, 4H), 8.06 (d, 1H), 8.26 (s, 1H), 9.34 (s, 1H), 9.51 (s, 1H).

1.3.9 $N^2,N^3$-bis(4-chloro-3-fluorophenyl)-6-nitroquinoxaline-2,3-diamine (ITRI TD-624)

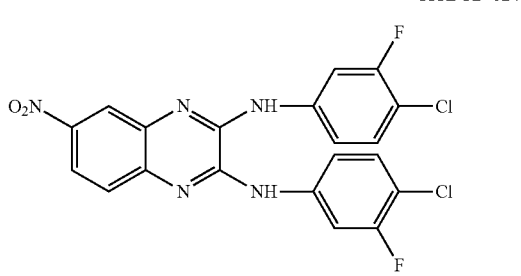

ITRI TD-624

$^1$H NMR (500 MHz, DMSO-d6) δ 7.41 (dd, 2H), 7.68 (m, 3H), 7.95 (s, 1H), 8.08 (d, 1H), 8.10 (d, 1H), 8.30 (s, 1H), 10.0 (b, 2H).

1.3.10 $N^2,N^3$-bis(4-phenylsulfonamide)-6-nitroquinoxaline-2,3-diamine (ITRI TD-629)

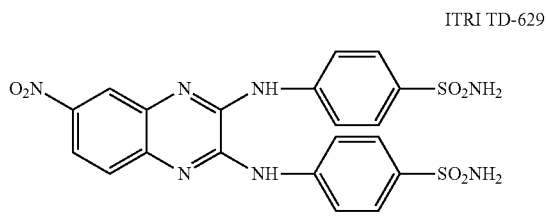 [SMILES: NS(=O)(=O)c1ccc(Nc2nc3ccc([N+](=O)[O-])cc3nc2Nc2ccc(S(N)(=O)=O)cc2)cc1]

ITRI TD-629

$^1$H NMR (500 MHz, DMSO-d6) δ 7.29 (b, 4H), 7.74 (d, 1H), 7.88 (d, 4H), 8.20 (m, 5H), 8.42 (s, 1H), 10.14 (s, 1H), 10.30 (b, 1H).

1.4 Synthetic Scheme IV

The compounds of the present invention can be obtained from above Synthetic Scheme IV, the detailed synthetic scheme is described below. In Synthetic Scheme IV, 4-(2-chloro-7-nitroquinoxalin-3-ylamino)phenol), 3-chloro-N-(4-methoxyphenyl)-6-nitroquinoxalin-2-amine), 4-(2-chloro-7-nitroquinoxalin-3-ylamino)-3-methylphenol) or 3-chloro-N-(5-methyl-1H-pyrazol-3-yl)-6-nitroquinoxalin-2-amine) (1 equiv) and phenylamine analogues (1.2 equiv) were added in DMF (3 to 5 ml). The mixture was then heated to 110° C. for 3 hr. After the reaction was completed, adding water into the reaction mixture, extracting the reaction mixture with ethyl acetate, then washing by ethyl acetate. After drying, concentrating and drying under reduced pressure to obtain the crude product. The crude product was further filtered with ethyl acetate/hexane by normal chromatograph to obtain ITRI TD-605, ITRI TD-612, ITRI TD-619, ITRI TD-625, ITRI TD-626, ITRI TD-628, ITRI TD-630, ITRI TD-631 compounds.

1.4.1 $N^3$-(3-ethynylphenyl)-$N^2$-(4-methoxyphenyl)-6-nitroquinoxaline-2,3-diamine (ITRI TR-605)

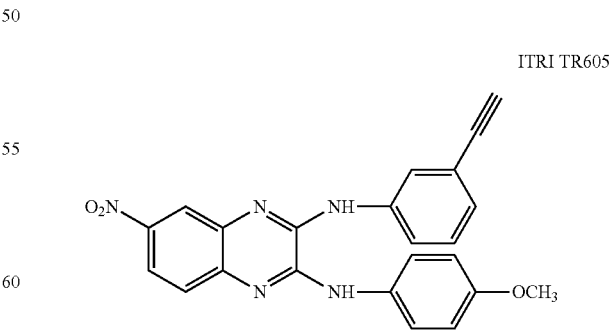

ITRI TR605

$^1$H NMR (500 MHz, DMSO-d6) ▢▢▢▢▢▢▢▢s, ▢▢▢▢4.21 (s, 1H), 7.00 (d, 2H), 7.21 (d, 1H), 7.42 (t, 1H), 7.59 (d, 1H), 8.01 (dd, 2H), 8.02 (d, 2H), 8.07 (d, 1H), 8.26 (s, 1H), 9.34 (s, 1H), 9.41 (s, 1H).

1.4.2 3-(2-(4-methoxyphenylamino)-6-nitroquinoxalin-3-ylamino)phenol (ITRI TD-612)

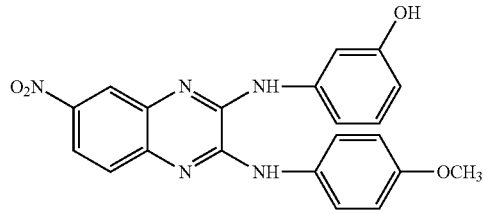

ITRI TD-612

¹H NMR (500 MHz, DMSO-d6) ☐☐☐☐☐☐☐☐☐s, ☐☐☐☐☐6.51 (d, 1H), 7.02 (dd, 2H), 7.17 (t, 1H), 7.24 (d, 1H), 7.56 (d, 1H), 7.68 (s, 1H), 7.77 (dd, 2H), 8.06 (d, 1H), 8.30 (s, 1H), 9.16 (s, 1H), 9.45 (s, 1H), 9.47 (s, 1H).

1.4.3 4-(2-(3-ethynylphenylamino)-7-nitroquinoxalin-3-ylamino)phenol (ITRI TD-619)

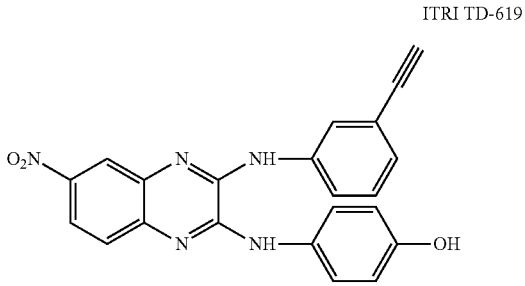 [SMILES: C#Cc1cccc(Nc2nc3cc([N+](=O)[O-])ccc3nc2Nc2ccc(O)cc2)c1]

ITRI TD-619

¹H NMR (500 MHz, DMSO-d6) ☐☐☐☐☐☐☐☐☐s, ☐☐☐☐☐6.81 (dd, 2H), 7.20 (d, 1H), 7.22 (t, 1H), 7.54 (d, 1H), 7.60 (dd, 2H), 8.00 (d, 2H), 8.05 (d, 1H), 8.23 (s, 1H), 9.31 (b, 2H), 9.39 (b, 1H).

14.4 4-(2-(3-ethynylphenylamino)-7-nitroquinoxalin-3-ylamino)-3-methylphenol (ITRI TD-625)

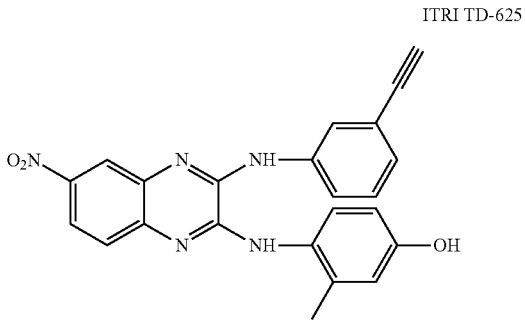 [SMILES: C#Cc1cccc(Nc2nc3cc([N+](=O)[O-])ccc3nc2Nc2ccc(O)cc2C)c1]

ITRI TD-625

¹H NMR (500 MHz, DMSO-d6) ☐☐☐☐☐☐☐☐☐s, ☐☐☐☐☐4.21 (s, 1H), 6.65 (d, 1H), 6.67 (s, 1H), 7.13 (d, 1H), 7.21 (d, 1H), 7.42 (m, 2H), 8.05 (d, 1H), 8.05 (m, 2H), 8.26 (s, 1H), 9.10 (s, 1H), 9.25 (s, 1H), 9.39 (s, 1H).

1.4.5 N³-(4-(trifluoromethyl)phenyl)-N²-(4-methoxyphenyl)-6-nitroquinoxaline-2,3-diamine (ITRI TD-626)

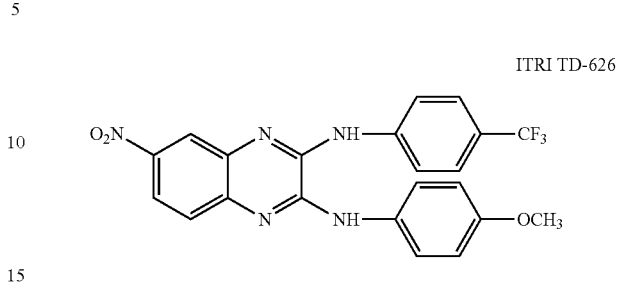

ITRI TD-626

¹H NMR (500 MHz, DMSO-d6) ☐☐☐☐☐☐☐☐☐s, ☐☐☐☐☐7.00 (d, 2H), 7.59 (d, 1H), 7.77 (m, 4H), 8.11 (d, 1H), 8.17 (d, 2H), 8.36 (s, 1H), 9.47 (s, 1H), 9.56 (s, 1H).

1.4.6 4-(2-(5-methyl-1H-pyrazol-3-ylamino)-6-nitroquinoxalin-3-ylamino)phenol (ITRI TD-628)

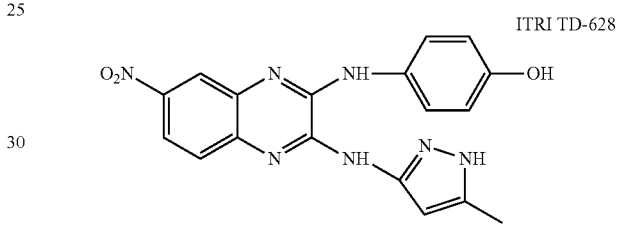

ITRI TD-628

¹H NMR (500 MHz, DMSO-d6) ☐☐☐☐☐☐☐☐☐s, ☐☐☐☐6.80 (d, 2H), 6.88 (s, 1H), 7.64 (d, 1H), 7.65 (d, 2H), 8.03 (d, 1H), 8.21 (s, 1H), 9.28 (s, 1H), 9.30 (s, 1H), 10.2 (s, 1H).

1.4.7 N³-(4-fluorophenyl)-N²-(4-methoxyphenyl)-6-nitroquinoxaline-2,3-diamine (ITRI TD-631)

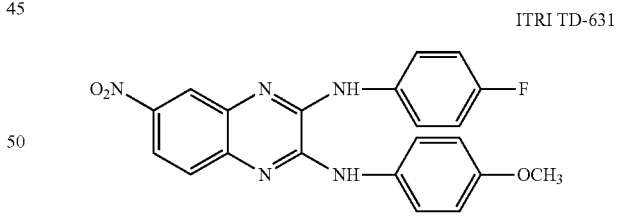

ITRI TD-631

¹H NMR (500 MHz, DMSO-d6) ☐☐☐☐☐☐☐☐☐s, ☐☐☐☐☐7.00 (d, 2H), 7.26 (t, 2H), 7.57 (d, 1H), 7.93 (d, 2H), 7.92 (dd, 2H), 8.07 (d, 1H), 8.25 (s, 1H), 9.31 (s, 1H), 9.40 (s, 1H).

1.5 Synthetic Scheme V

The compounds of the present invention can be obtained from above Synthetic Scheme V, the detailed synthetic scheme is described below. In Synthetic Scheme V, 2,3-dichloroquinoxalin-6-yl)(phenyl)methanone (1 equiv) and 3-ethynylbenzenamine (1.2 equiv) in IPA was heated to reflux for 5 hr, then is cooled to extract solid, and the solid was washing with IPA and dried to obtain the TD-632 (formula II).

1.5.1 2,3-bis(3-ethynylphenylamino)quinoxalin-6-yl)(phenyl)methanone (TD-632)

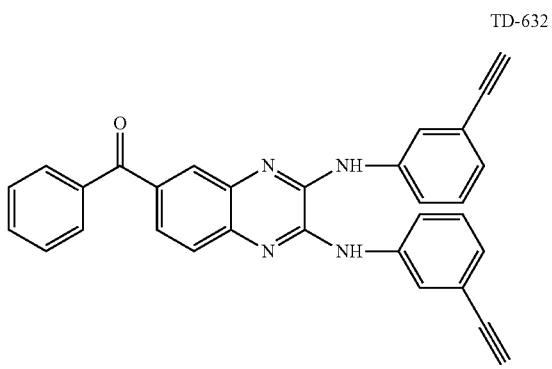 [SMILES: C#Cc1cccc(Nc2nc3ccc(C(=O)c4ccccc4)cc3nc2Nc2cccc(C#C)c2)c1]

TD-632

$^1$H NMR (400 MHz, DMSO-$d_6$) □4.2 (s, 1H), 4.1 (s, 1H), 7.24 (d, 1H), 7.25 (d, 1H), 7.56 (d, 2H), 7.40 (m, 2H), 7.6 (m, 3H), 7.64 (m 3H), 7.79 (m 2H) 7.82 (s 1H), 8.15 (b, 2H), 9.25 (b, 2H).

EXAMPLE 2

Bioassay 2.1 Materials and Methods
2.1.1 Reagents and Antibodies

Sorafenib (Nexavar), erlotinib (Tarceva) and Paclitaxel were kindly provided by Bayer Pharmaceuticals (Pittsburgh, Pa., USA) and Roche Pharmaceuticals (Basel, Switzerland) respectively. Okadaic acid (OA) was purchased from Cayman Chemical (Ann Arbor, Mich., USA) and z-VAD-fmk was obtained from Sigma (St. Louis, Mo., USA). For in vitro studies, drugs at various concentrations were dissolved in dimethyl sulfoxide (DMSO), and added to cells in Dulbecco's modified Eagle's medium (DMEM) or Roswell Park Memorial Institute (RPMI) containing 5% fetal bovine serum (FBS).

For in vitro studies, the final DMSO concentration was 0.1% after addition to the medium. Antibodies for immunoblotting including anti-CIP2A, anti-Akt1, anti-PARP, anti-PP2A-C, anti-PP2A-A, anti-PP2A-B55 and anti-Elk-1 were purchased from Santa Cruz Biotechnology (San Diego, Calif., USA). Other antibodies such, as anti-caspase-3 and anti-P-Akt (Ser473) were obtained from Cell Signaling (Danvers, Mass., USA).

2.1.2 Cell Culture

The Sk-Hep1, PLC/PRF/5 (PLC) and Hep3B cell lines were obtained from American Type Culture Collection (ATCC; Manassas, Va., USA). The Huh-7 HCC cell line was obtained from the Health Science Research Resources Bank (HSRRB; Osaka, Japan; JCRB0403). Cells were maintained in DMEM supplemented with 10% FBS in a 37° C. humidified incubator in an atmosphere of 5% $CO^2$ in air. Other cell lines, including non-small cell lung cancer cells e.g. H358, H460 and A549 and human squamous cell carcinoma cells e.g. NCI-1703, H2170, H520, SW900 and NCI—H226 all obtained from American Type Culture Collection (Manassas, Va.) were also provided for the assays describes below.

2.1.3 Apoptosis Analysis

The numbers of apoptotic cells after treatment with DMSO, sorafenib or the erlotinib derivatives of the present invention were assessed by flow cytometry (sub-G1). Annexin-V/propidium iodidie (PI) double-staining assay was used to determine numbers of both apoptotic and necrotic cells. For above tow assays, HCC cells were harvested after the erlotinib derivatives of the present invention treatment and incubated with PI alone for sub-G1 assay and in combination with annexin-V—FITC. Analysis of cell composition was performed by flow cytometry. The erlotinib derivatives of the present invention-induced apoptotic cell death was assessed by western blot analysis of activated caspases and cleaved PARP, and cell death enzyme-linked immunosorbent assay (ELISA) for cytoplasmic histone-associated DNA fragments (Roche, Indianapolis, Ind., USA). The effect of co-treatment with the erlotinib derivatives of the present invention and z-VAD-fmk, the caspase inhibitor, were assessed by western blot analysis and flow cytometry.

2.1.4 Western Blot Analysis

Cells were treated with caspase-3, PARP, P-Akt, Akt, CIP2A and so on for a time period. Cell lysates were analyzed by western blot analysis.

2.1.5 Gene Knockdown Using siRNA

Smart-pool small interfering RNA (siRNA) reagents, including control (D-001810-10) and PP2A-C (L-001810-01) were purchased from Dharmacon (Chicago, Ill., USA) 11121-11133). according to the manufacturer's instructions, cells were first transfected with siRNA (final concentration, 100 nM) in six-well plates using the Dharma-FECT4 transfection reagent (Dharmacon) for 48 h. Afterward, the medium was replaced and the cells were treated with the erlotinib derivatives of the present invention (2 μM for 48 h) and then harvested for western blot analysis and apoptosis analysis by flow cytometry.

2.1.6 Transient Transfection

CIP2A cDNA (KIAA1524) and Elk-1 cDNA was purchased from Origene (RC219918 and RG208921; Rockville, Md., USA). Following transfection for 48 h, cells were treated with the erlotinib derivatives of the present invention for the indicated times and subsequently harvested for further analysis.

2.1.7 PP2A Phosphatase Activity

The protein phosphatase activity in each cell lysate was determined by measuring the generation of free phosphate from threonine phosphopeptide using the malachite green-phosphate complex assay as described by the manufacturer (Upstate Biotechnology, Lake Placid, N.Y., USA). In brief, HCC cell lysates were first prepared in a low-detergent lysis buffer. The phosphatase assay was carried out in a PP2A-specific reaction butter (Milipore, Billerica, Mass., USA) containing 750 μM phosphopeptide substrate. After incubation for 10 min at 30° C., the malachite dye was added and free phosphate was measured by optical density at 650 nm. In order to avoid variation resulting from differences in the amount of immunoprecipitation protein between samples, the phosphatase activities were normalized to the amounts of PP2A immunoprecipitated, which were detected and quantified by immunoblot analysis for each treatment group.

2.1.8 Luciferase Reporter Constructs for the CIP2A Promoter and 5' Detection Analysis The upstream region of the CIP2A promoter containing exon 1 (−2000 bp to −1 bp) was amplified by PCR from the genomic DNA of PLC5 cells according to a previous study and cloned into the reporter vector, Firefly vector (pGL4.17, Promega, Madison, Wis., USA) by KpnI and Bg/II restriction sites. PCR amplified promoter regions −1000/−1, −400/−1, −300/−1, −150/−1, −110/−1, were cloned into the KpnI and Bg/II restriction sites of the pGL4-basic vector. The nucleotide sequence of the clones was verified by sequencing.

2.1.9 Chromatin Immunoprecipitation (ChIP) Assay

ChIP kit was purchased from Novus Biologicals (NBP1-71709; Littleton, Colo., USA). ChIP was performed using $1 \times 10^7$ PLC5 cells, which were treated with the erlotinib derivatives of the present invention for 16 h, followed by 37% formaldehyde (Sigma, F1635) at 1% final concentration and v/v for 10 min at room temperature to cross-link proteins to DNA. After cross-linking, the cells were washed twice with 1× ice-cold PBS containing protease inhibitor cocktail. The cells were collected and centrifuged at 800×g for 5 min, resuspended in 400 µl of lysis buffer with protease inhibitor cocktail. The cells were then sonicated for six pulses, 50% output for 15 s at each pulse, with a 60-s ice rest in between pulses. The cell lysate was centrifuged at 12500×g for 5 min at 4° C. Immunoprecipitation was performed by adding Elk1 or rabbit IgG antibodies as the negative control. The immunocomplex was precipitated by incubation with 25 µl of protein A/G magnetic beads for 1 h at 4° C. The protein-DNA complex was eluted using 200 µl of elution buffer from the beads. Cross-linking of protein-DNA was reversed by adding 8 µl of 5 M NaCl at 95° C. for 15 min. The DNA was purified using spin columns and 2 µl of the DNA was used in the semi-PCR reaction for amplification of the CIP2A promoter region (−139/−16 bp).

2.1.10 Xenograft Tumor Growth

Male NCr athymic nude mice (5-7 weeks of age) were obtained from the National Laboratory Animal Center (Taipei, Taiwan). All experimental procedures using these mice were performed in accordance with protocols approved by the Institutional Laboratory Animal Care and Use Committee of National Taiwan University. Each mouse was inoculated subcutaneously in the dorsal flank with $1 \times 10^6$ PLC5 or A549 cells suspended in serum-free medium containing 50% Matrigel (BD Biosciences, Bedford, Mass., USA). When tumors reached 100-150 mm³, mice were treated with sorafenib, the erlotinib derivatives of the present invention, or vehicle (control) at 10 mg/kg/day daily by oral gavage for 4 weeks.

2.1.11 Immunohistochemical Staining

Paraffin-embedded HCC tissue sections (4-mm) on poly-1-lysine-coated slides were deparaffinized and rinsed with 10 mM Tris-HCl (pH 7.4) and 150 mM sodium chloride. Peroxidase was quenched with methanol and 3% hydrogen peroxide. Slides were then placed in 10 mM citrate buffer (pH 6.0) at 100° C. for 20 mM in a pressurized heating chamber. After incubation with 1:200 dilution of p-Akt1/2/3 (Thr 308)-R antibody (ab8805, Abcam, Cambridge, UK) and with 1:100 dilution of CIP2A antibody (ab84547, Abcam) for 1 h at room temperature, slides were thoroughly washed three times with PBS. Bound antibodies were detected using the EnVision Detection Systems Peroxidase/DAB, Rabbit/Mouse kit (Dako, Glostrup, Denmark). The slides were then counterstained with hematoxylin. Paraffin-embedded sections of mouse kidney tissue and human colon carcinoma were used as positive controls for p-Akt1/2/3 and CIP-2A, respectively, as described in the datasheet from the manufacturer. Negative controls had the primary antibody replaced by PBS. The expression of p-Akt1/2/3 and CIP-2A was assessed semiquantitatively based on the intensity of staining by a board certified pathologist. The intensity of staining was scored as negative, weak, moderate and strong.

2.2.12 Surface Plasmon Resonance (SPR)

Binding affinities of full-length SET and truncated SET to PP2Ac and the effect of the erlotinib derivatives of the present invention on disrupting SET and PP2Ac were analyzed. PP2Ac-GST recombinant protein was bound in the CMS chip pre-coated with GST-capture antibodies. Sensorgrams were generated by injecting several concentrations of the erlotinib derivatives of the present invention mixed with fixed-concentration of SET recombinant protein, or the mixture of different concentration of truncated SET proteins in a fixed-dose EMQA. PP2Ac-GST recombinant protein used for this experiment was purchased from Abnova (H00005515) and SET-His recombinant protein was obtained from Genway (GWB-ATG319).

2.2.13 Statistical Analysis

Tumor growth data points are reported as mean tumor volume±S.E. and compared by independent samples t-test. Characteristics of clinical samples were compared by $\chi^2$-test. A P-value<0.05 was regarded as statistically significant on the two-tailed tests. All statistical analysis was computed using SPSS for Windows software (version 17.0; SPSS, Inc., Chicago, Ill., USA).

Result

Figure 1B:
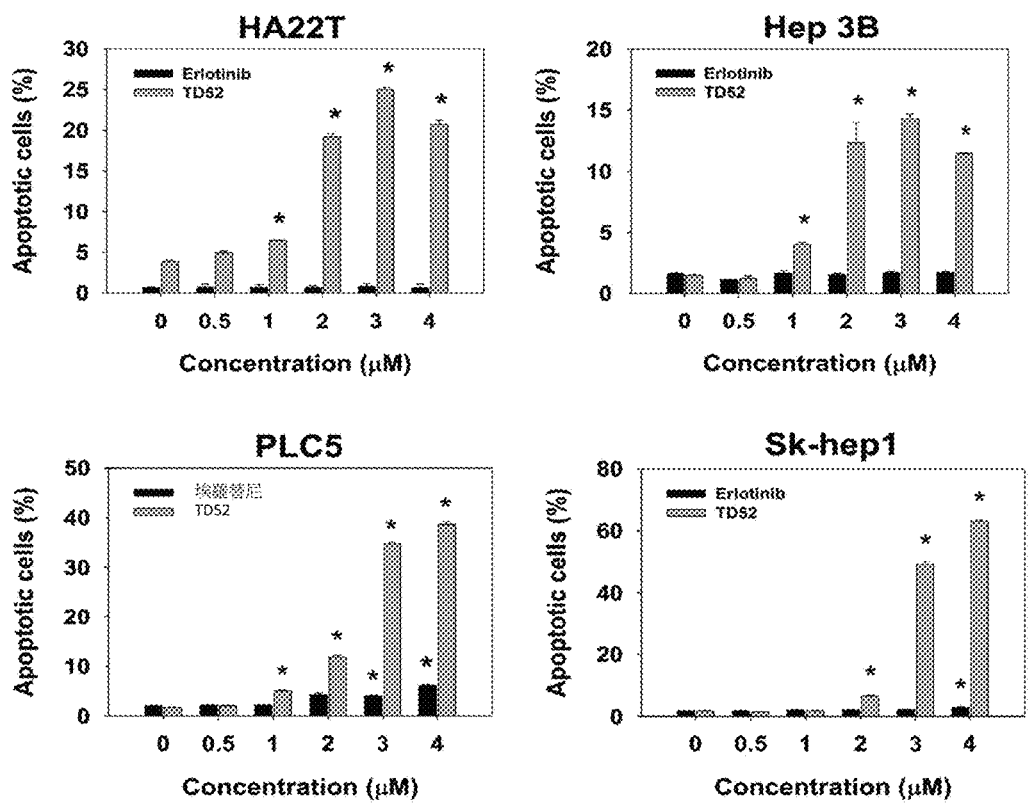

2.2.1 Erlotinib Derivatives of the Present Invention Increases HCC Cell Apoptosis The present invention compared the antitumor activities of an erlotinib derivative of the present invention, TD-52, and erlotinib on HCC cells. The present invention used MTT assay to evaluate cell viability after exposure to TD-52 or erlotinib for 48 h. As shown in FIG. 1A, TD-52 caused greater reduction in cell viability than erlotinib in all the HCC cell lines (including HA22T, Hep3Bm PLC5 and Hep3B), which showed HA22T ($IC_{50}$=0.9 µmol/l), Hep3B ($IC_{50}$=0.9 µmol/l), PLC5 ($IC_{50}$=0.8 µmol/l) and Sk-Hep1 ($IC_{50}$=1.2 µmol/l). To further evaluate the cell apoptosis induced by the treatments, all four cell lines were treated with TD-52 and erlotinib at the indicated concentration for 24 h and the percentages of sub-G1 cells were determined by flow cytometry (FIG. 1B). Results of sub-G1 analysis echoed the findings observed in the MTT assay, that is, they showed that TD-52 had more potent antitumor effects on HCC cells than erlotinib.

Figure 1C:
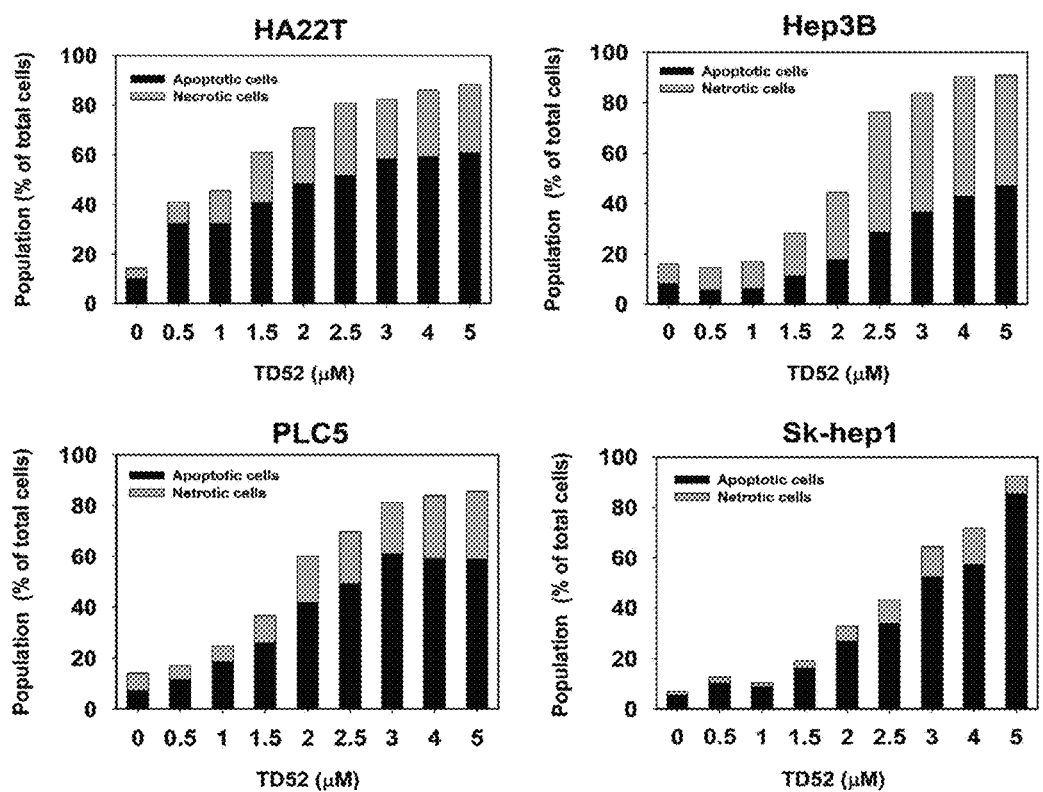
Figure 1D:
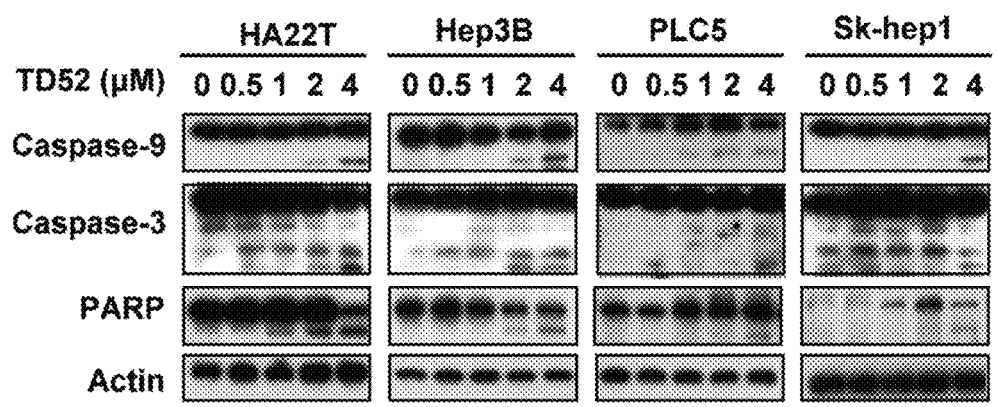
Figure 1E:
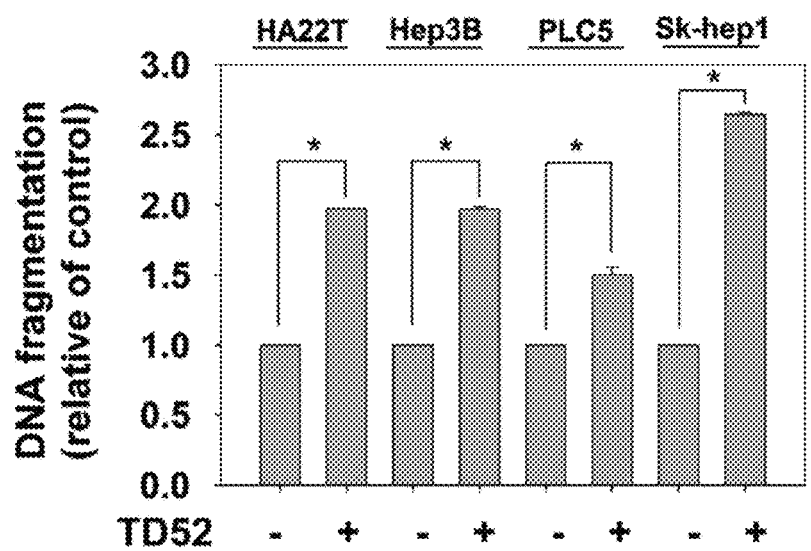
Figure 1F:
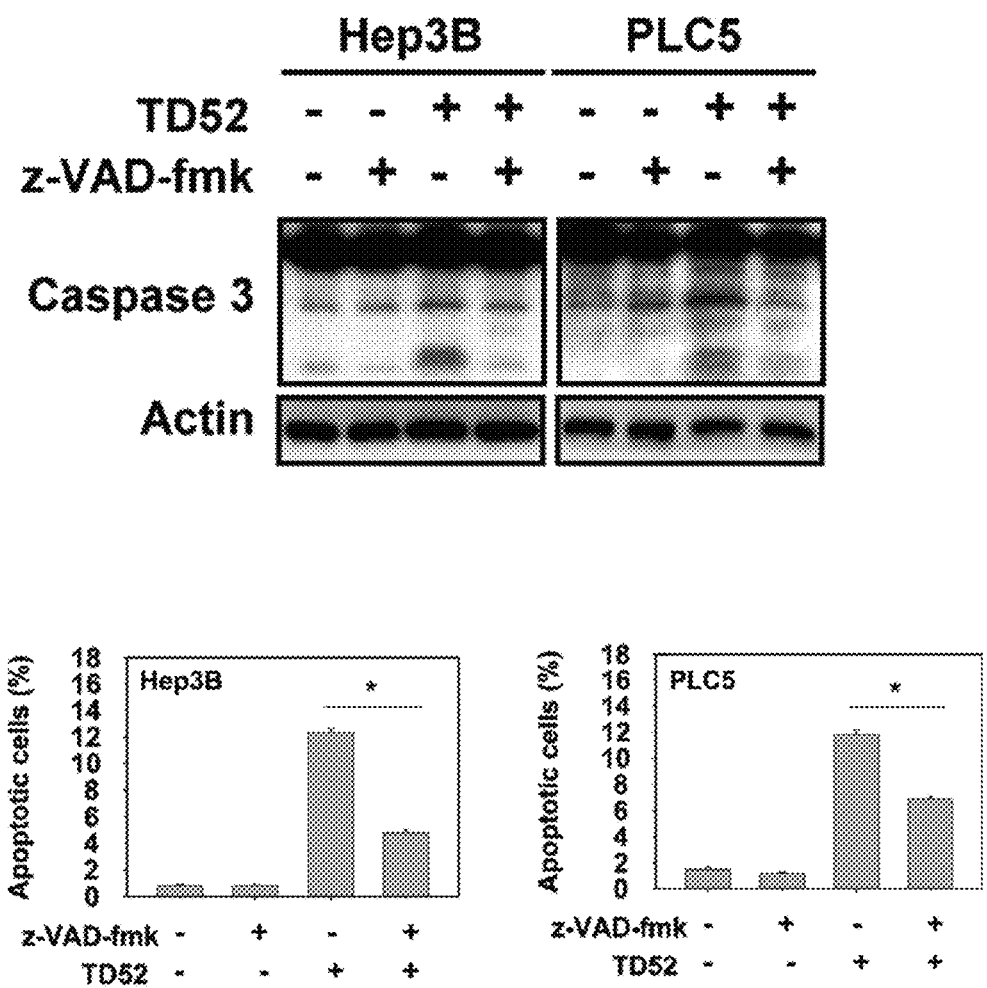
Figure 1G:
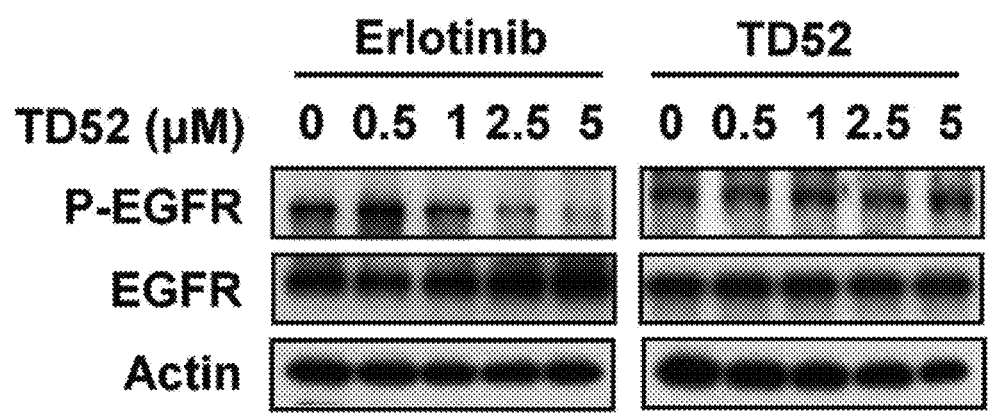

To better characterize the antitumor properties of TD-52, annexin-V/propidium iodide (PI) double-staining assay, western blot analysis, cell cycle analysis and DNA fragmentation assay were performed (FIGS. 1C-1E). At dose increase, the proportion of apoptosis and necrosis of cancer cell ware analyzed by annexin-V—FITC/PI double-staining assay. After 48 h incubation with TD-52 at 2 µM or higher doses, the extents of cancer cell death, included apoptotic and necrotic death, were 50% or more in the four different HCC cells (FIG. 1C). Hep3B cell was more sensitive to TD-52-induced necrotic cell death, while apoptotic cell death was responsible for larger proportion of cell death in HA22T, PLC5 and Sk-Hep1 cells at the same dose range. As indicated by the results of western blotting, TD-52 treatment caused the activation of caspase-9, caspase-3 and subsequent cleavage of poly (ADP-ribose) polymerase (PARP) in a dose-dependent manner (FIG. 1D). Furthermore, after co-treatment of TD-52 (2 µM) and z-VAD-fmk, the pan-caspase inhibitor for 48 hr, reduced the pro-apoptotic effects of TD-52 (FIG. 1F). Also, DNA fragmentation of cancer cells was induced by TD-52 at relatively low concentration (1 µmol/l, 24 h; FIG. 1E). However, TD-52 were not have the ability of epidermal growth factor receptor (EGFR) kinase inhibitor as erlotinib shown (FIG. 1G). Therefore, these results suggest that the erlotinib derivatives of the present invention exhibits more potent antitumor activity than erlotinib, and that this activity is independent of EGFR kinase inhibition.

In addition, the present invention respectively used 1 µM and 10 µM of each erlotinib derivative to detect cell viability and $IC_{50}$ of human squamous cell carcinoma cells e.g. NCI-1703, H2170, H520, SW900 and NCI—H226, non-small cell lung cancer cells e.g. A549, H358. The results are shown in Table 5, which validates that the erlotinib derivatives of the present invention effectively induce cancer cells death.

Figure 2A:
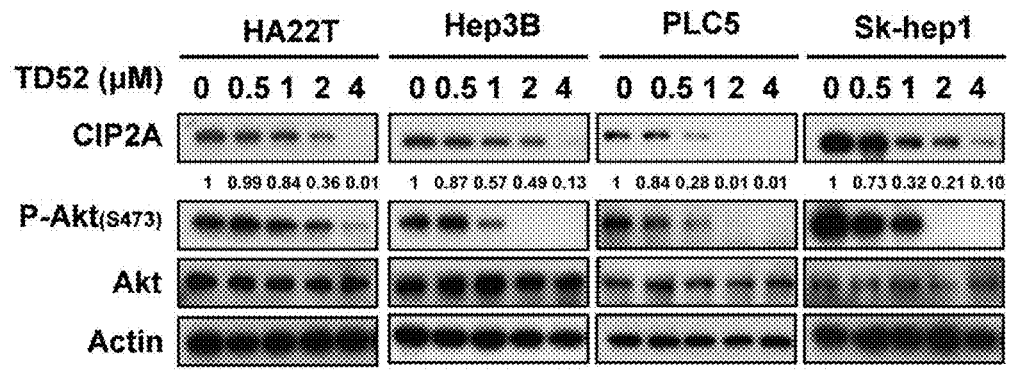
FIGS. 2A to 2H show that p-Akt downregulation by inhibition of CIP2A determines effects of TD-52 on apoptosis in HCC cells.
Figure 2B:
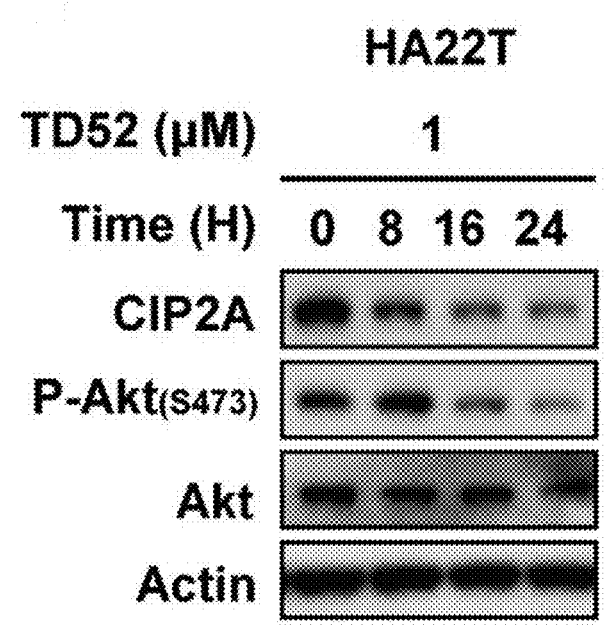
Figure 2C:
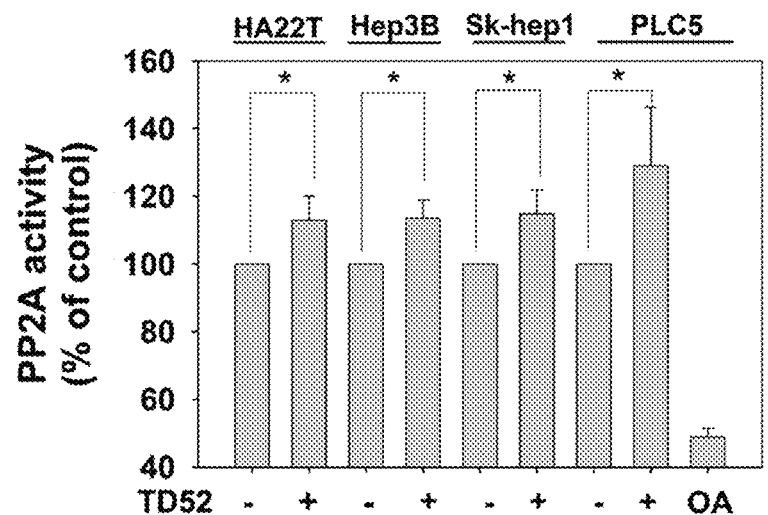
Figure 2D:
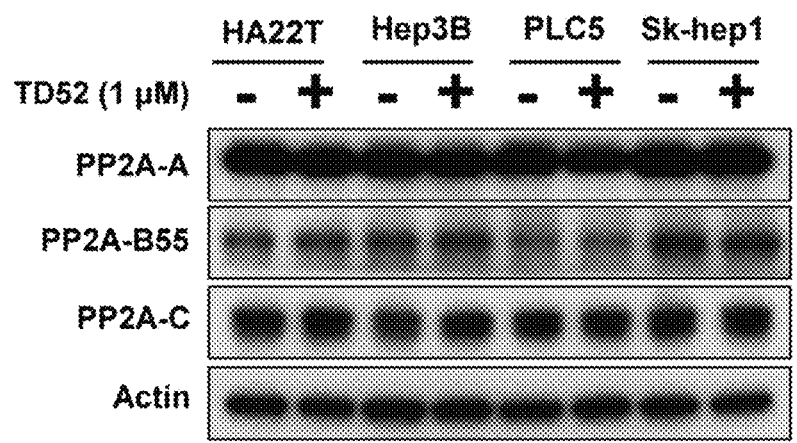

2.2.2 Enhancement of PP2A by Inhibition of CIP2A Determines the Pro-Apoptotic Effect of the Erlotinib Derivatives of the Present Invention The present invention next investigated the molecular mechanism associated with TD-52, with particular focus on the cancerous inhibitor of protein phosphatase 2A (CIP2A)-protein phosphatase 2A (PP2A)-p-Akt signaling pathway. As shown in FIGS. 2A and 2B, TD-52 downregulated the protein expression of CIP2A and p-Akt in a dose- and time-dependent manner. Furthermore, PP2A activity was enhanced after HCC cells treated with 1 µLTD-52 for 24 hr (FIG. 2C), while the expression level of PP2A-related subunits, PP2A-A, PP2A-B5 and PP2A-C subunits, were not affected. From these results, PP2A activity was enhanced by TD-52 treatment through inhibition of expression of CIP2A that subsequently led to downregulation of p-AKT and HCC cell apoptosis (FIG. 2D).

Figure 2E:
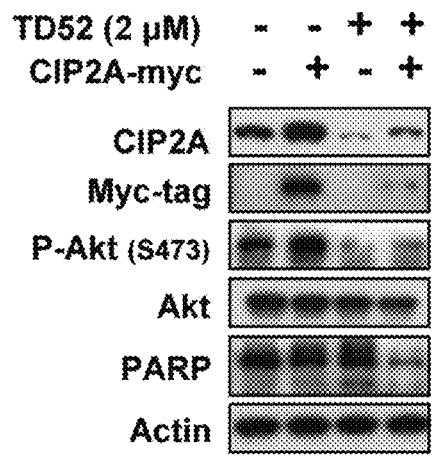
Figure 2E:
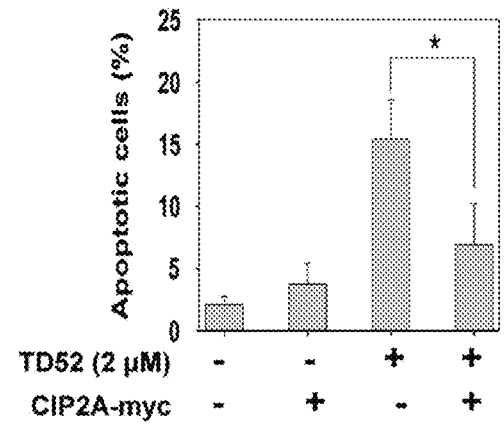
Figure 2F:
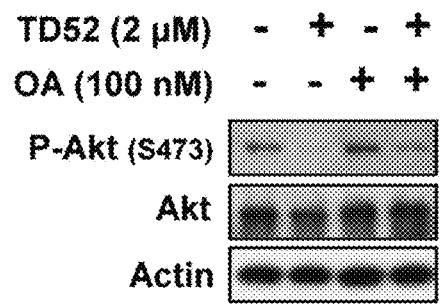
Figure 2F:
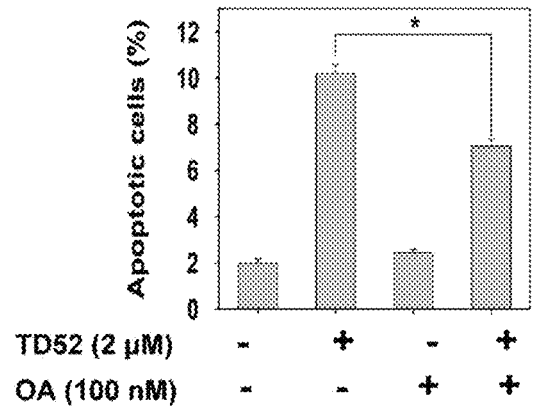
Figure 2G:
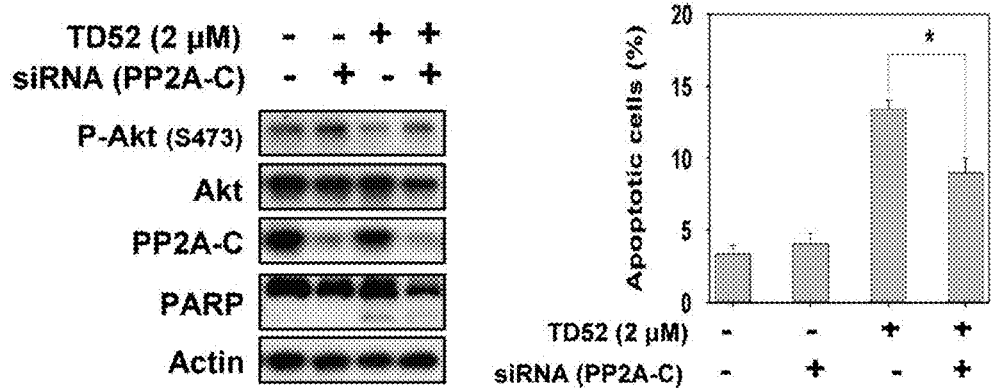
Figure 2H:
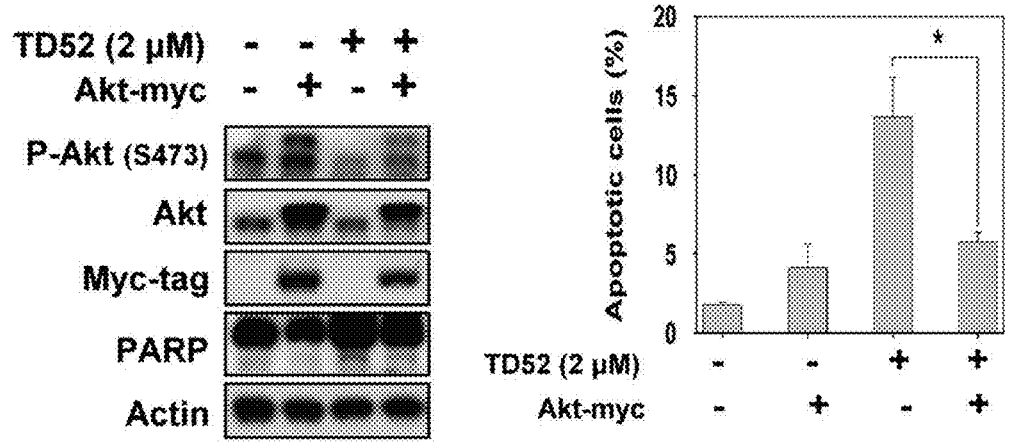

To confirm the role of the CIP2A/PP2A/p-Akt pathway in mediating induction of apoptosis by TD-52, after transfecting PCL5 cells with ectopic overexpression of myc-tagged CIP2A for 48 hr (FIG. 2E), cells were treated with TD-52 at 2 µM for 24 hr. Compared with wild-type cells, the expression level of p-AKT was upregulated in the CIP2A-overexpressing cells. Furthermore, using sub-G1 analysis, the apoptotic effect of TD-52 was significantly reduced in these CIP2A-overexpressing PLC5 cells. Next, the present invention investigated the role of PP2A in mediating the effects of TD-52 on HCC cells by two strategies, knockdown of PP2A by silencing RNA (siRNA), and co-treatment with a PP2A inhibitor, okadaic acid (OA) (FIGS. 2F and 2G). When PLC5 cells were treated with OA at 100 nM, the expression level of p-Akt was enhanced and TD-52-induced HCC tumor cell apoptosis was reduced (FIG. 2F). Similarly, when PP2A was knocked down by siRNA of PP2A, expression of p-Akt was increased and the antitumor effects of TD-52 were reversed. The present invention further generated Akt-overexpressing PLC5 cells by transient transfection and found that TD-52-induced apoptosis of HCC cells was significantly reduced (FIG. 2H). The results validated the critical role of the CIP2A/PP2A/p-Akt signaling pathway in mediating the effect of TD-52 in HCC cells.

Figure 3A:
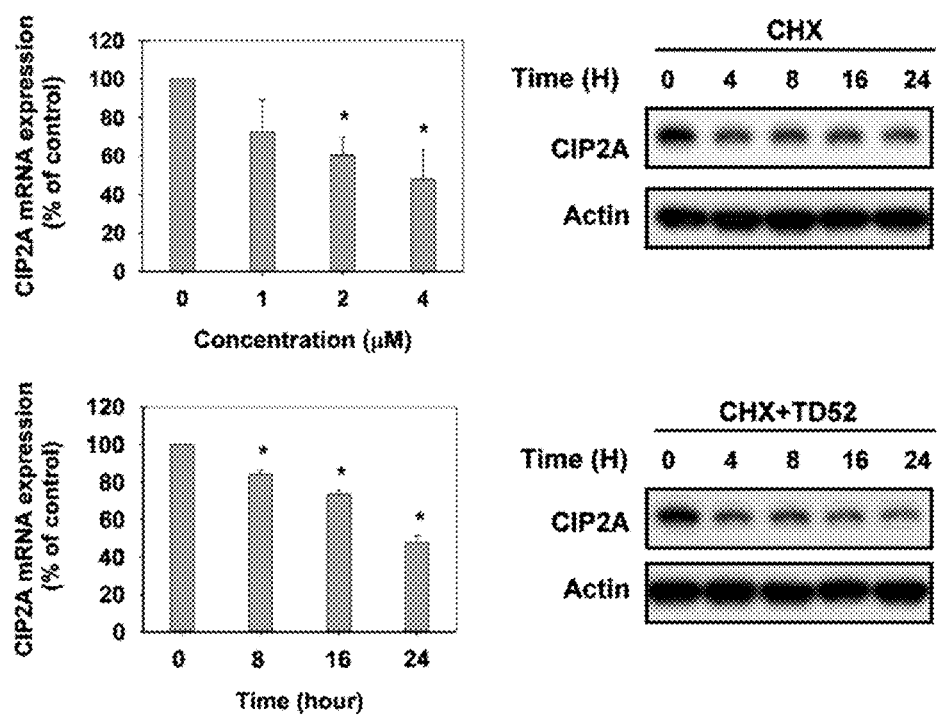
FIGS. 3A to 3D show that TD-52 downregulates transcription of CIP2A via interfering Elk-1 function.
Figure 3B:
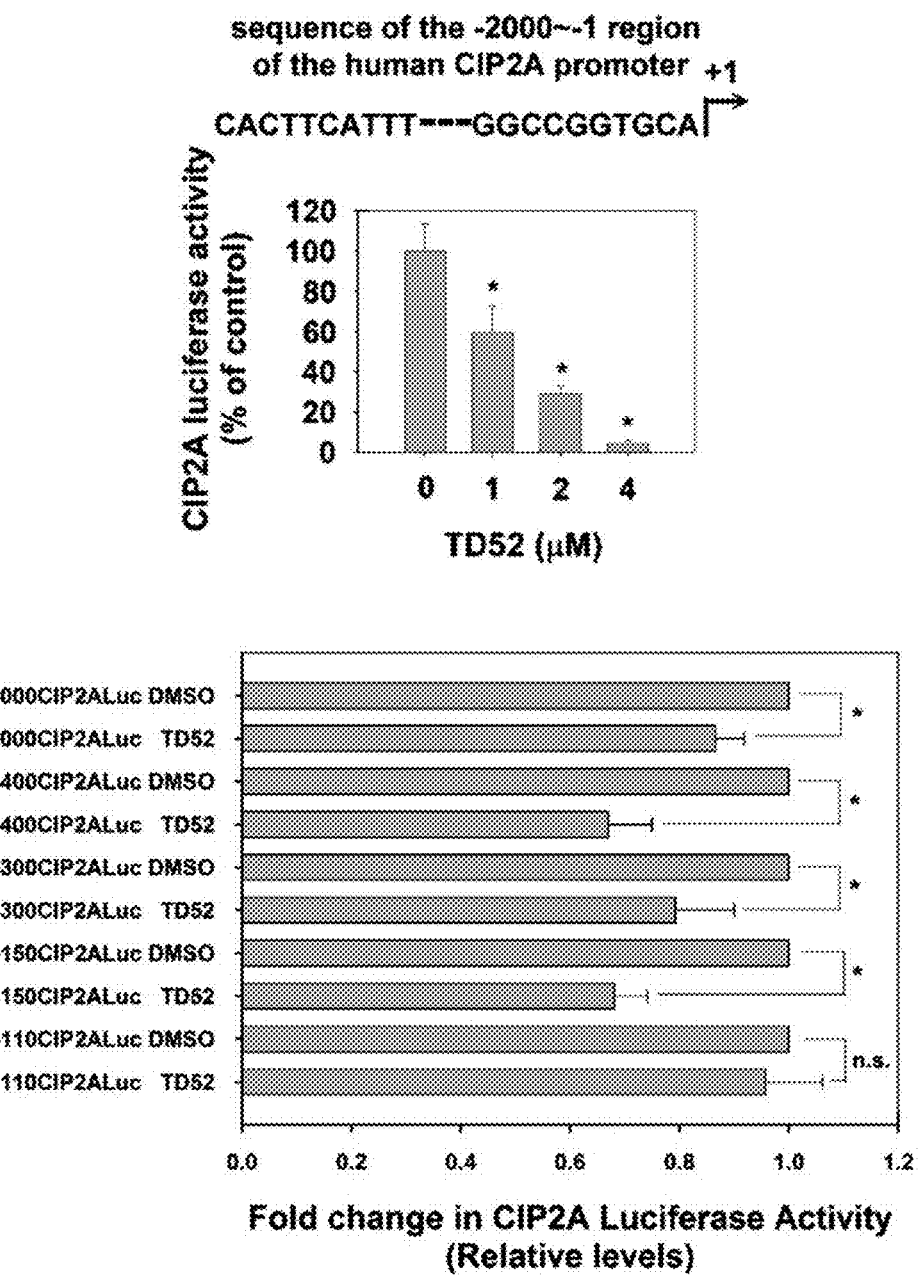
Figure 3C:
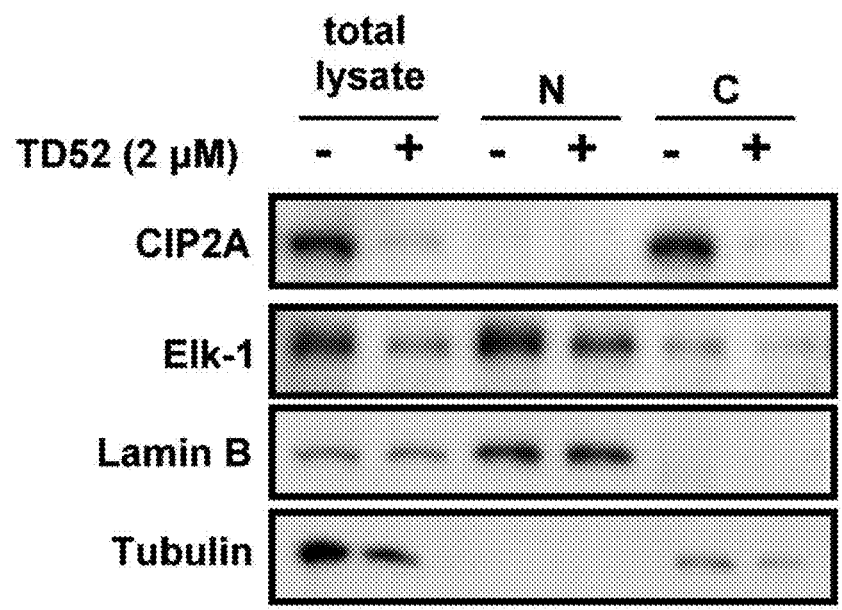
Figure 3D:
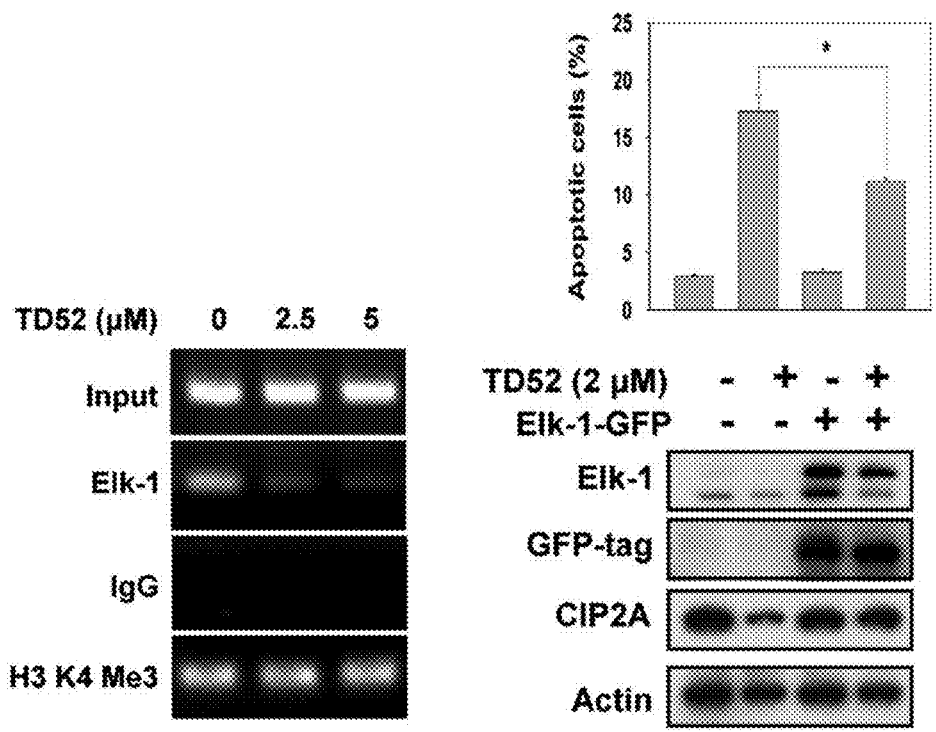

2.2.3 the Erlotinib Derivatives of the Present Invention Induce Cell Apoptosis Via CIP2A-PP2A-p-Akt Signaling Pathway To further understand how TD-52 affects the CIP2A-PP2A-p-Akt signaling pathway, the present invention examined whether elimination (degradation) of CIP2A was affected by TD-52 when translation was blocked by the protein synthesis inhibitor cycloheximide. As shown in FIG. 3A, the time needed for CIP2A protein degradation was not significantly affected by TD-52, but the mRNA expression detected by RT-PCR was suppressed by TD-52 treatment. As the result suggested that TD-52 inhibited transcription of CIP2A, the present invention examined whether the CIP2A promoter determined the mechanism of action. When the promoter of the CIP2A gene was linked to luciferase reporters, TD-52 suppressed the luciferase activity in a dose-dependent manner (FIG. 3B, upper panel). In order to further identify which elements of the CIP2A gene promoter region were critical for the effects of TD-52, serial PCR deletion clones were constructed in pGL4 luciferase vectors. As shown in FIG. 3B, TD-52 treatment did not affect luciferase activity in cells with the −110/−1 construct. This finding suggests that the region between −110 and −150 contains the binding sites for CIP2A expression in PLC5 cells. Prior reports suggested that Elk-1 could bind to this region. Elk-1 regulated the expression levels of CIP2A in cervical and endometrial cancers together with another transcriptional factor, Ets1. Therefore, the present invention tested the role of Elk-1 in mediating the regulation of the CIP2A-PP2A-p-Akt signaling pathway in HCC cells. In treatment-PLC5 cells, expression of Elk-1 and CIP2A could be detected by western blot; while the expression of Elk-1 was particularly dominant in the nuclear lysate, the expression of CIP2A was mostly identified in the cytoplasmic lysate. After TD-52 treatment, however, the expression of both CIP2A and Elk-1 in PLC5 cells was significantly inhibited (FIG. 3C). To further illustrate the interplay between Elk-1 and CIP2A, the present invention used chromatin immunoprecipitation (ChIP) analysis and quantitative PCR to assess the direct association of Elk1 with the CIP2A promoter gene (FIG. 3D). In untreated cells, Elk-1 expression was detected in a cross-linked protein-DNA complex, which supported the direct binding of Elk-1 to the promoter regions of the CIP2A gene. Furthermore, when cells were exposed to TD-52, the expression of Elk-1 was reduced in a dose-dependent manner. These results indicate that TD-52 downregulates CIP2A by interfering with the binding between Elk-1 and the CIP2A promoter subsequently leading to decreased transcription of CIP2A. As CIP2A was inhibited, PP2A was activated, leading to dephosphorylation of Akt and cancer cell apoptosis. Moreover, ectopic overexpression of Elk-1 reduced TD-52-induced downregulation of CIP2A and cancer cell apoptosis (FIG. 3D, right panel).

Figure 4A:
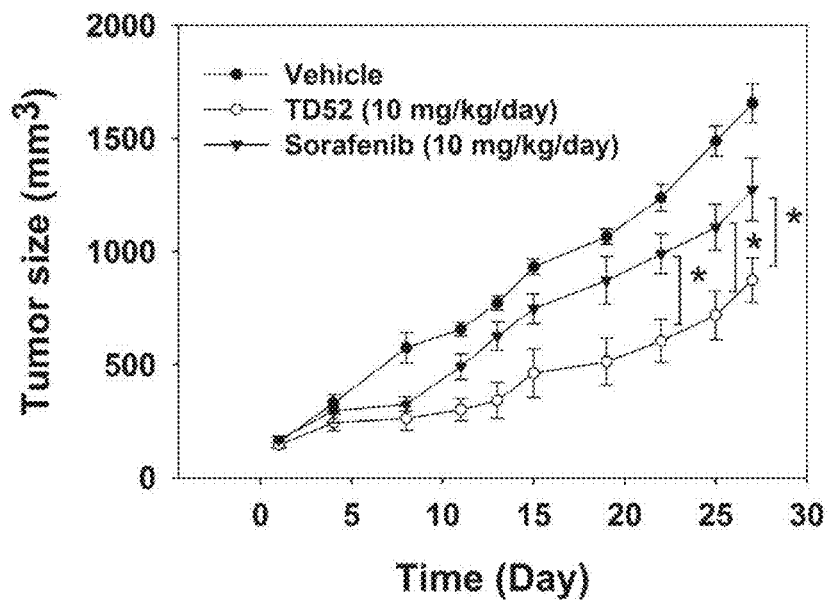
FIGS. 4A to 4D validates that the CIP2A-PP2A-p-Akt signaling pathway in clinical HCC samples and in vivo PLC5 nude mice model.
Figure 4B:
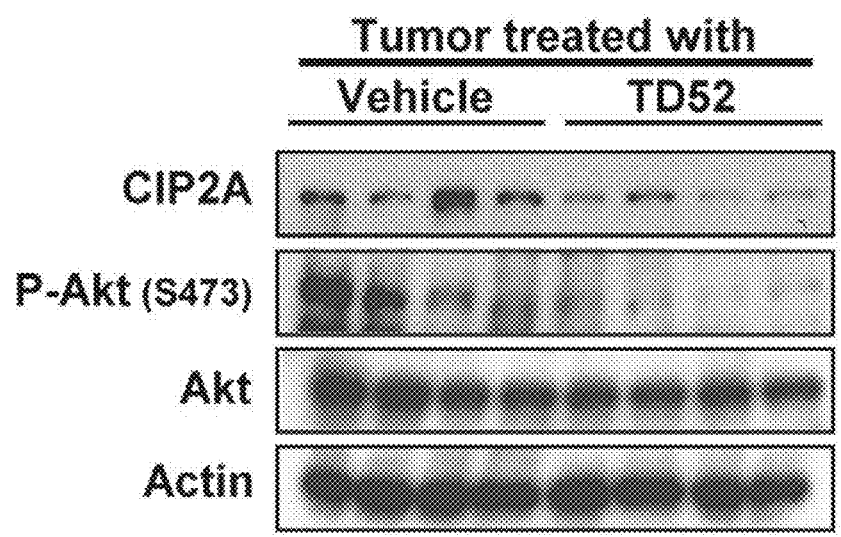
Figure 4C:
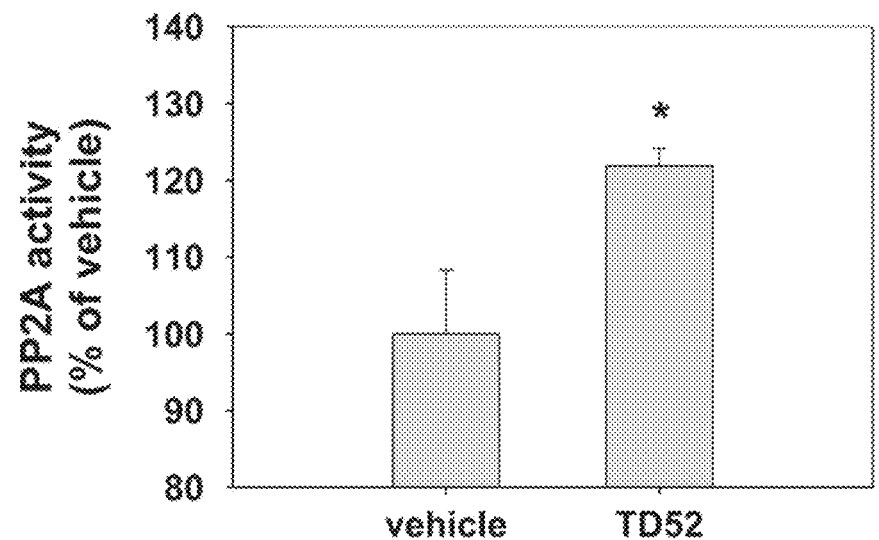
Figure 4D:
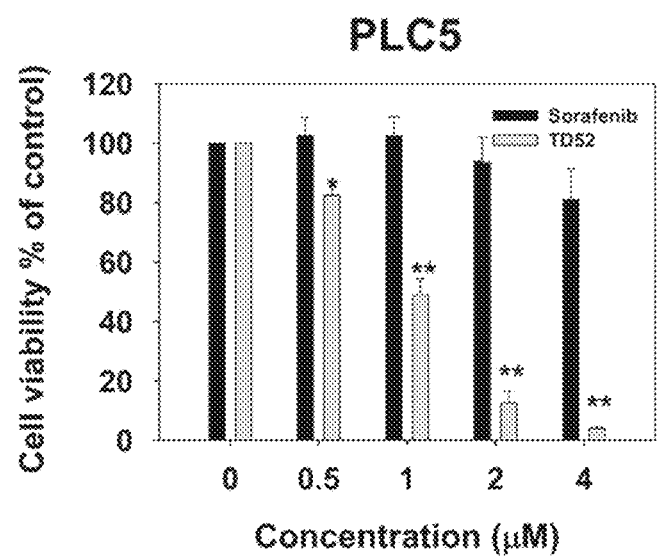
Figure 4E:
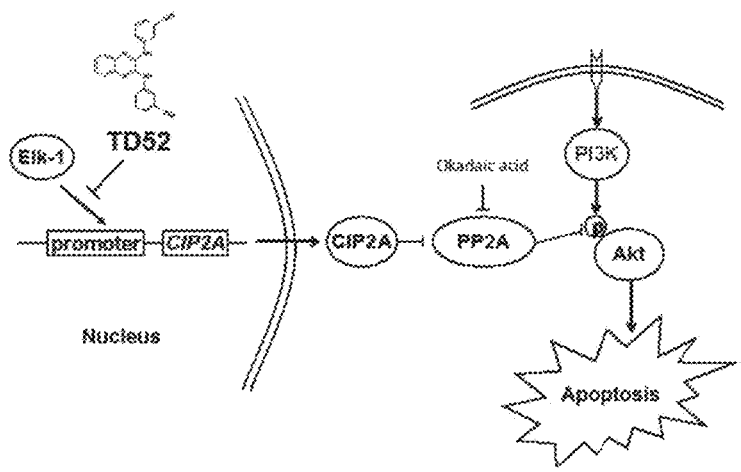
FIG. 4E is schema of the signaling pathways that explains pro-apoptotic effects of TD-52 in HCC cells.

2.2.4 In Vivo Antitumor Effects of the Erlotinib Derivatives of the Present Invention on a PLC5 Xenograft Tumor Model The present invention used a PLC5 xenograft mouse model to assess the effects of TD-52 in vivo. The present choose sorafenib as one of the comparative treatment arms. Tumor-bearing mice were administered sorafenib (10 mg/kg), TD-52 (10 mg/kg) or DMSO (vehicle, as control). After 4 weeks of treatment, the tumor sizes of the mice receiving sorafenib and TD-52 were smaller than those of the control arm. Furthermore, in a comparison with sorafenib, TD-52 treatment demonstrated more potent inhibition of in vivo tumor growth and in vitro cell viability ($P<0.05$; FIGS. 4A and 4D). The present invention further examined the xenografted tumors taken from mice receiving TD-52 and vehicle to confirm the molecular events in the tumor tissue. As shown in FIGS. 4B and 4C, TD-52 enhanced PP2A activity and downregulated the expression levels of CIP2A and p-Akt in in vivo tumor samples, mirroring the molecular events found in vitro. In summary, TD-52 was shown to interfere with binding between Elk-1 and the promoter of the CIP2A gene subsequently leading to downregulation of transcription of CIP2A and increased PP2A activity. When PP2A activity was enhanced by TD-52, Akt was dephosphorylated, promoting HCC cell apoptosis.

2.2.5 Detection of Liver Tumor Tissue from Patients with HCC

Figure 4F:
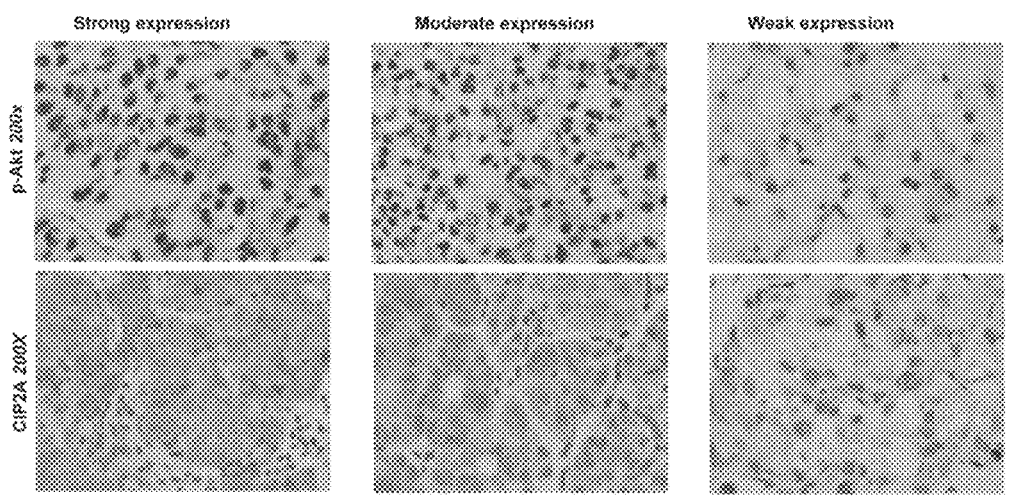
FIG. 4F is immunohistochemical image of p-Akt nuclear expression and CIP2A cytoplasmic expression in clinical HCC samples.

To validate the clinical relevance of p-Akt and CIP2A, the present invention analyzed tumor samples from 147 patients with HCCs and their clinical characteristics. In FIG. 4F, CIP2A is highly expressed in 55.5% of the tumor samples examined. Moreover, immunohistochemical staining for p-Akt showed that the intensity of nuclear expression of p-Akt correlated significantly with cytoplasmic staining for CIP2A.

2.2.6 Oncoprotein SET is Overexpressed in Tumor Tissues

Figure 5A:
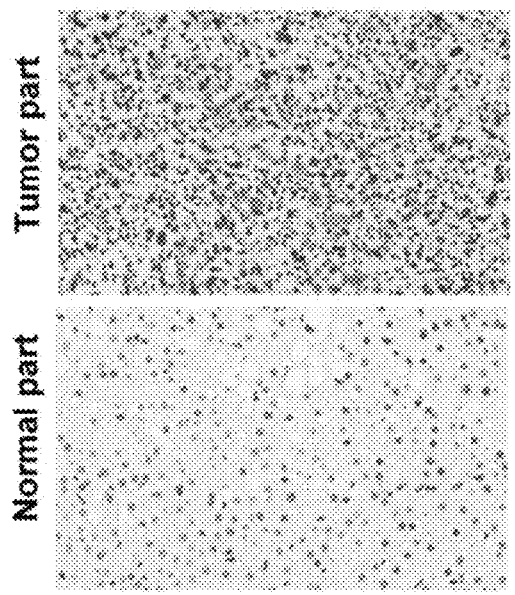
FIGS. 5A to 5F show SET overexpression in tumor tissue of patients with HCC.
Figure 5B:
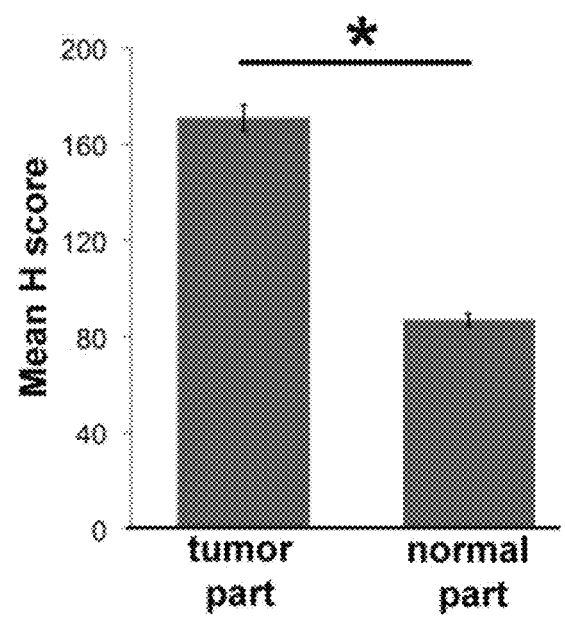
Figure 5C:
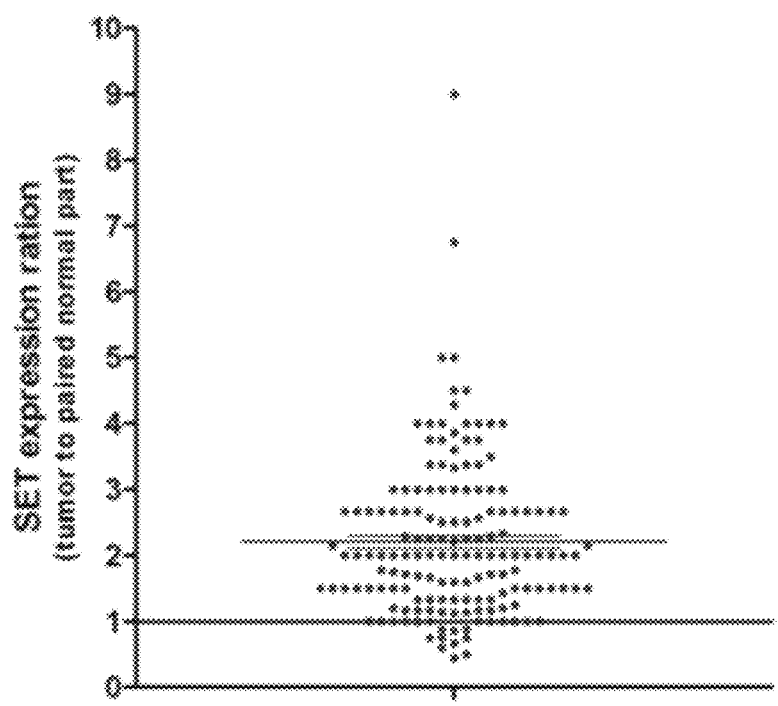
Figure 5D:
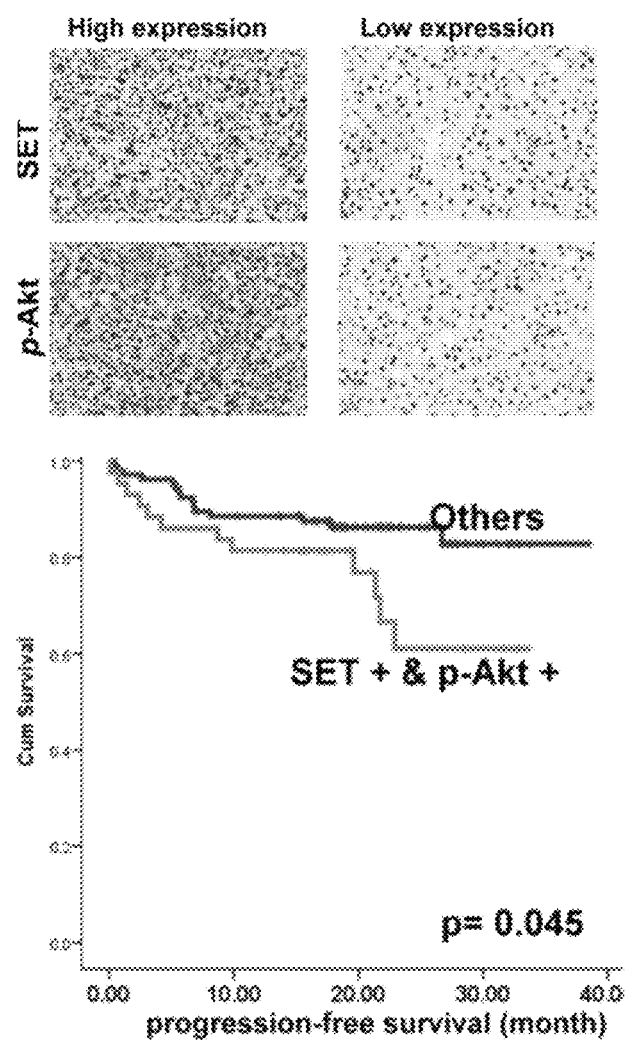
Figure 5E:
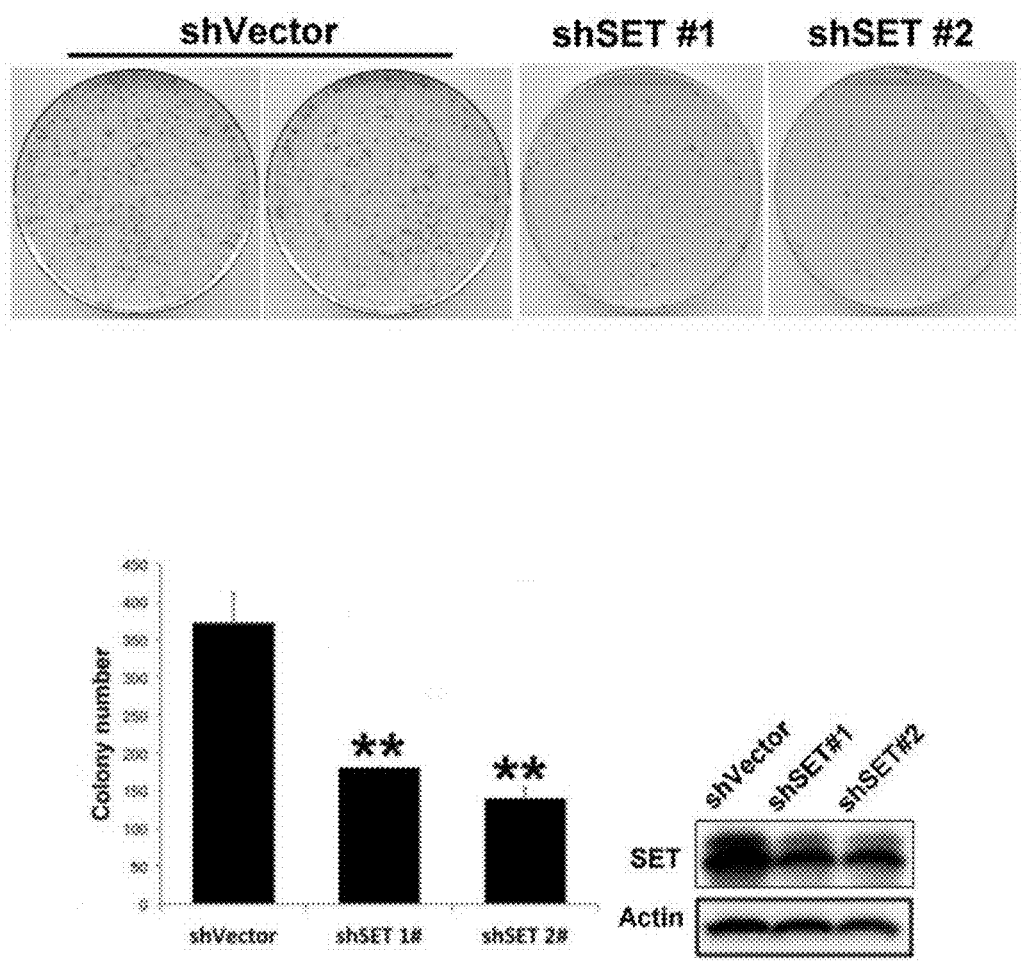
Figure 5F:
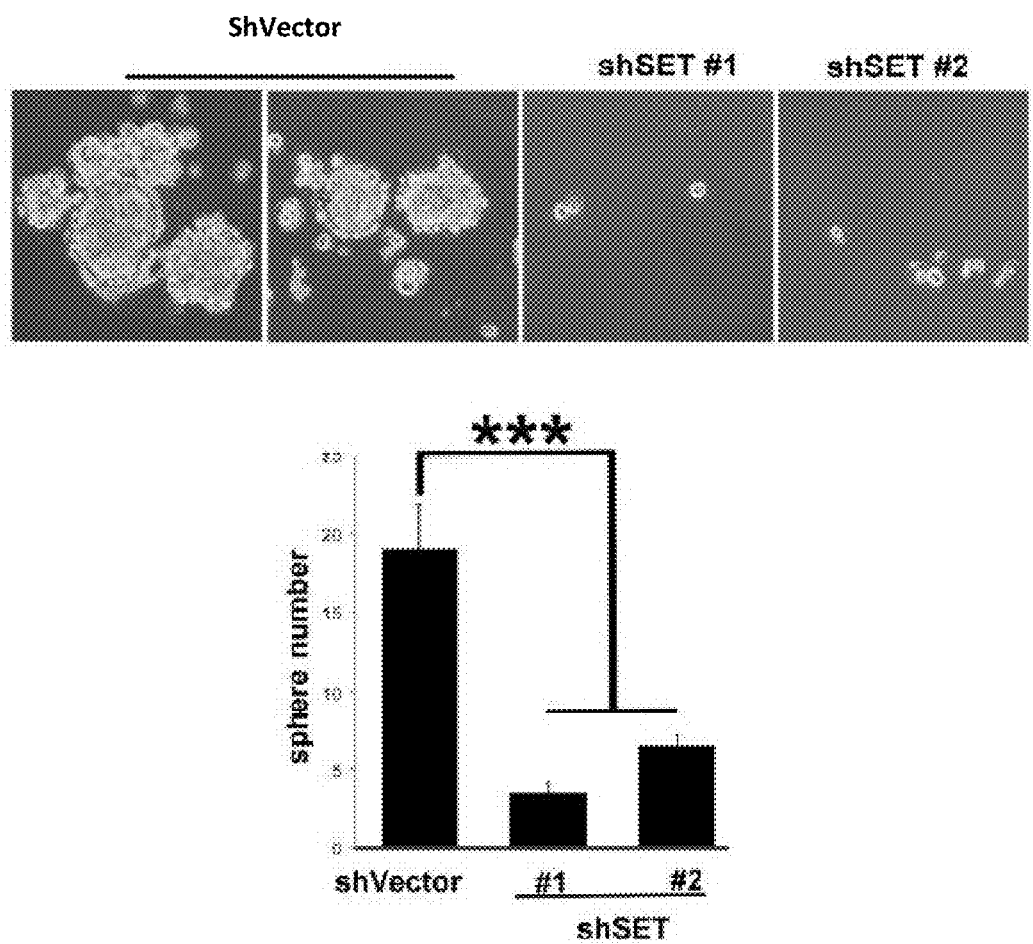

The present invention further confirms that SET is overexpressed in HCC tumor tissues and co-expression of SET and p-Akt predicts higher post-resection recurrence risks in HCC patients. We first confirmed the aberrant expressions of oncoprotein SET in a set comprising 147 HCC patients with paired samples collected from the tumor tissue and adjacent normal tissue (FIGS. 5A to 5C). The expression of SET in the tumor tissue was significantly higher than that observed in normal tissue. The average H scores of SET expressions in the 294 HCC tumor samples (a pair of samples for every patients) were 170.8 in the tumor tissue, and 86.7 in the non-tumor tissue (p=86.8) (FIG. 5B). The specificity of SET expression in tumors was further demonstrated when comparing the expression level of SET in tumors with its paired normal tissue from the same patient. As shown in FIG. 5C, almost every patients in our cohort had significantly higher SET expression in the tumor tissue with an average ratio of tumor to non-tumor SET expression of 2.2. Notably, high levels of SET expression were significantly associated with poor clinical characteristics, including advanced clinical stage and poor differentiation. Since SET is a potent inhibitor of the tumor suppressor phosphatase PP2A, the present invention next investigated whether the aberrant expression of SET is associated with the dysfunction of PP2A in HCC. Alternatively, high levels of SET expression were significantly associated with activation of Akt signaling, one of the important oncogenic signaling pathways regulated by PP2A (FIG. 5D). Of note, co-expression of high SET and p-Akt predicted higher risks of recurrence of HCC after surgery (FIG. 5D, lower panel). To further investigate the oncogenic potential of SET in HCC, the present invention assessed the effects of SET silencing on cell growth using specific shRNA. As shown in FIG. 5E, the growth rate of the PLC5 cells transfected with the shRNA against SET was significantly reduced as compared to cells transfected with negative control shRNA. In concordance, SET silencing lead to significantly reduced ability of hepatosphere formation of Hep3B cells (FIG. 5F). Taken together, these results indicated that aberrant expression of SET is a common event in promoting hepatocarcinogenesis. Also, the present invention validated that SET plays a critical oncogenic role in lung cancer by detecting NSCLC A549 cell lines and tissues from patients with NSCLC, and the binding of SET and PP2Ac (catalytic domain) led to enhance PP2A activity (data no show).

2.2.7 PP2A Promotes Downregulation of Akt and Apoptosis of HCC Cells

Figure 6A:
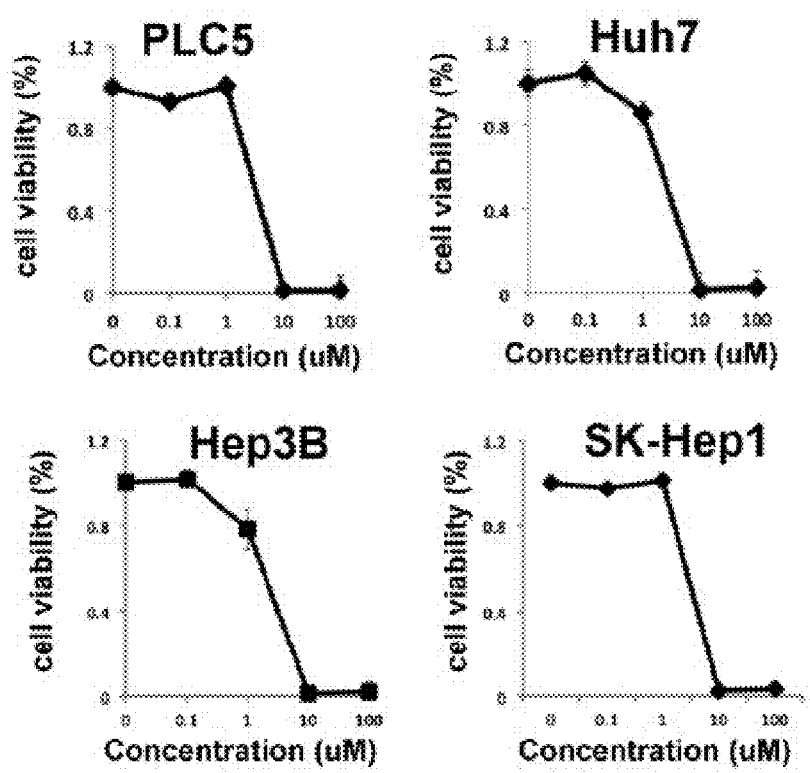
FIGS. 6A to 6F show the erlotinib derivatives (EMQA) of the present invention can be a SET antagonist to induce apoptosis of HCCs cells.
Figure 6B:
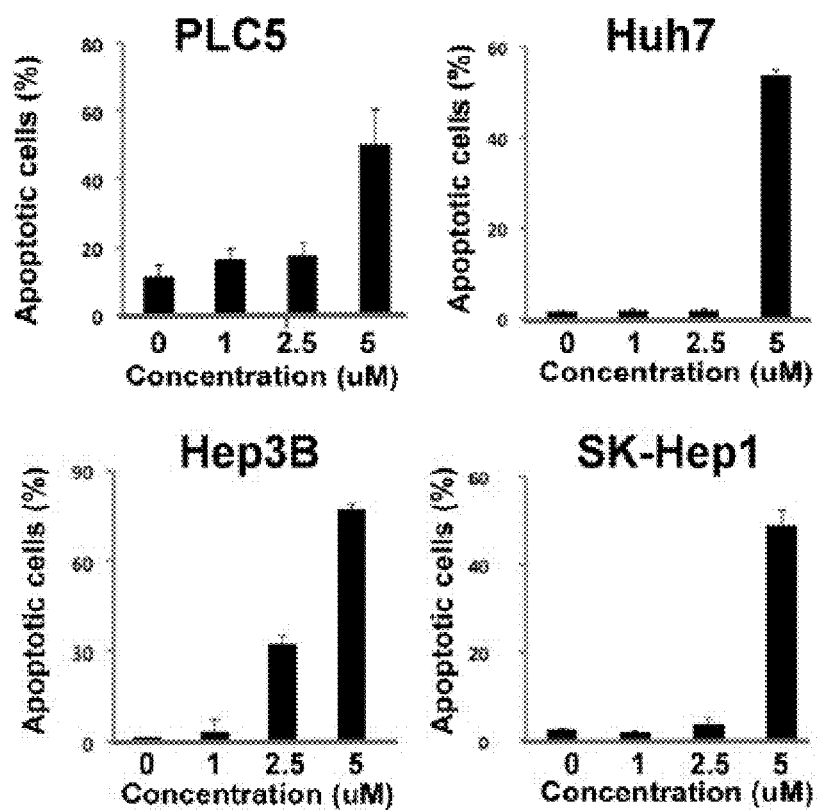
Figure 6C:
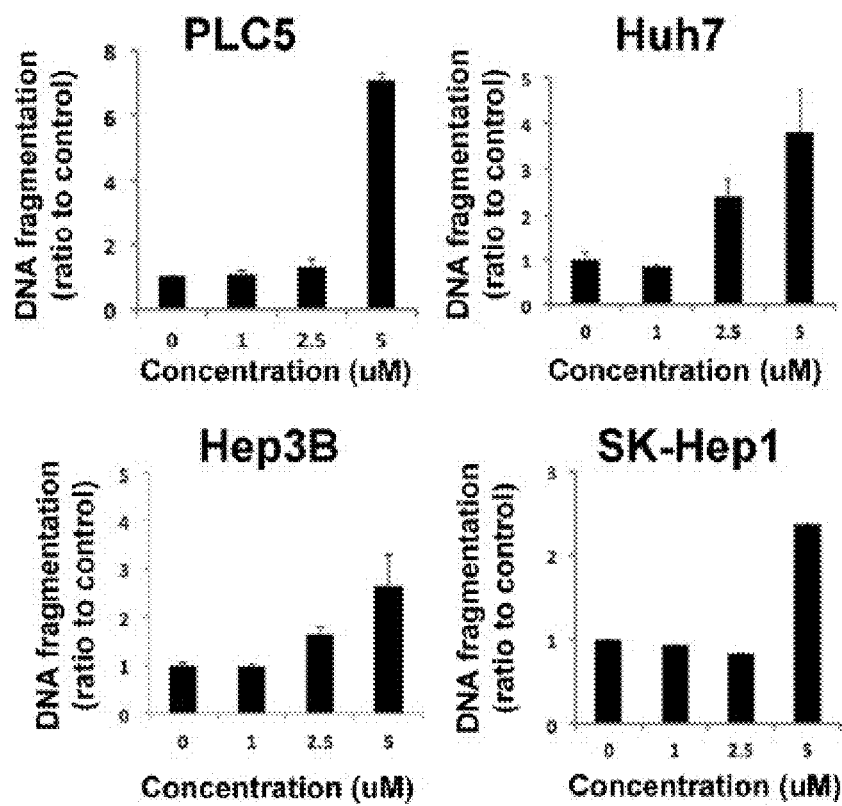
Figure 6D:
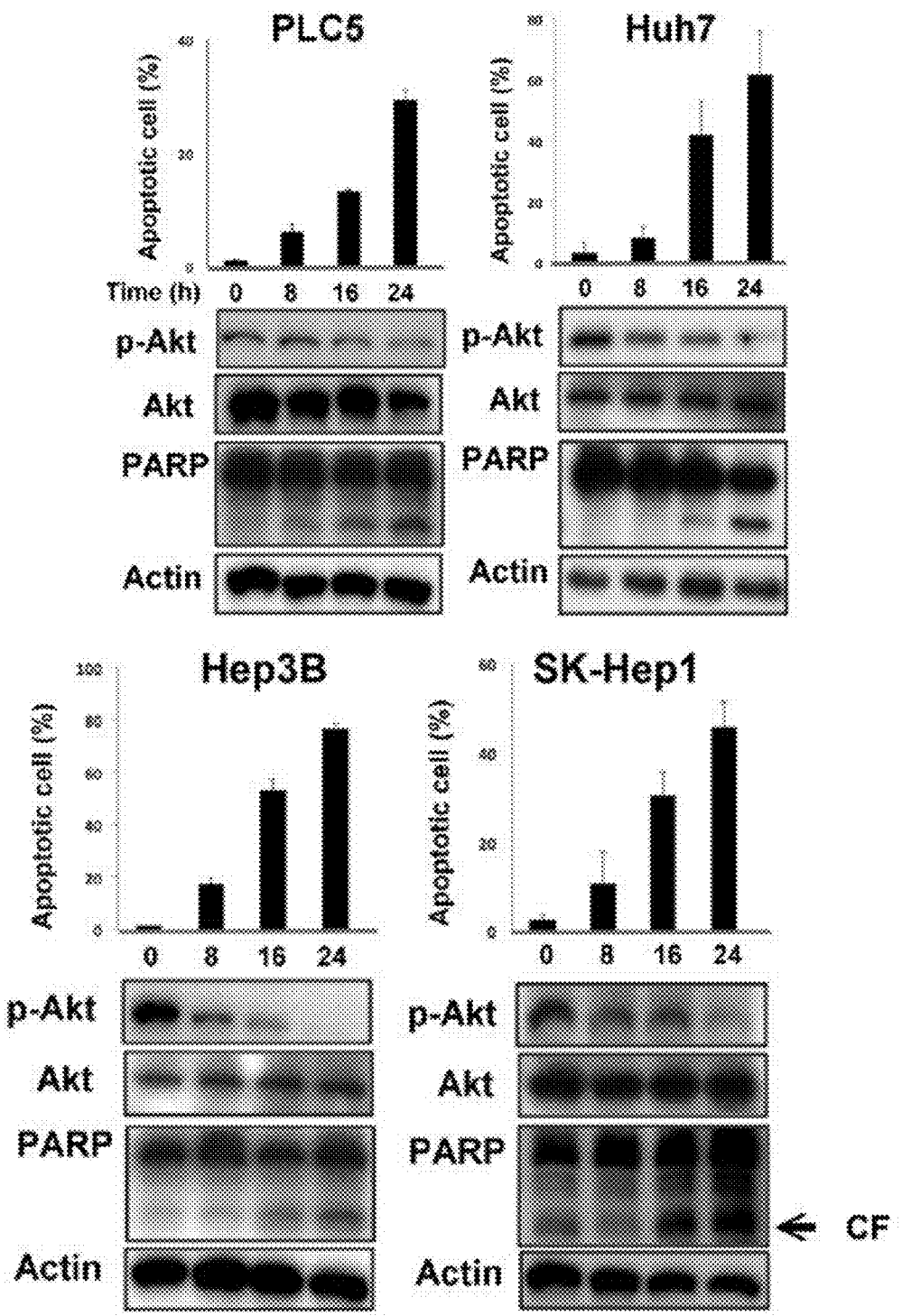
Figure 6E:
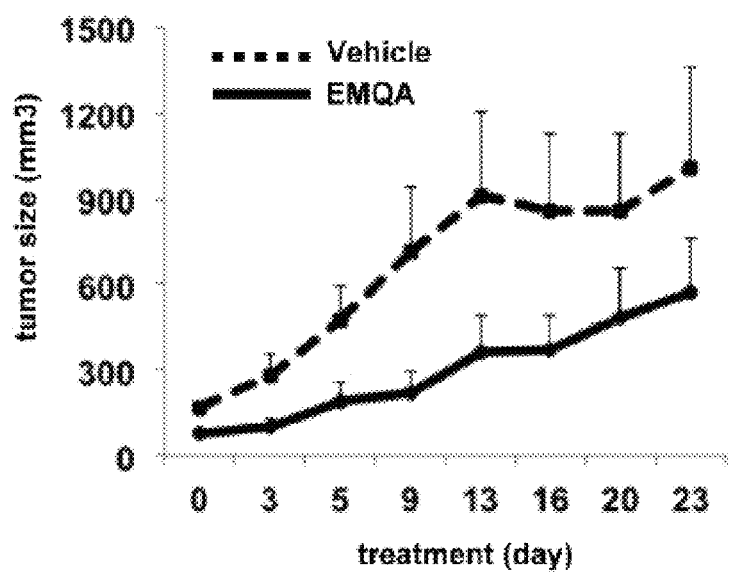
Figure 6F:
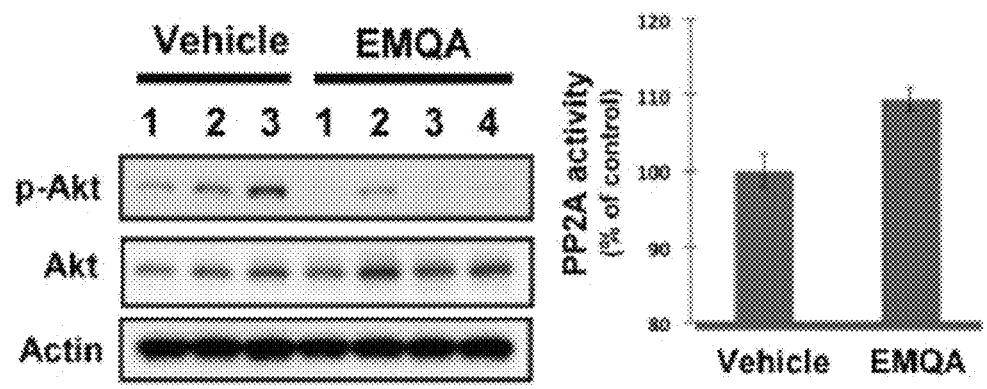

The present invention next investigated whether targeting SET-PP2A may constitute a potential anti-HCC strategy. First, the present invention used MTT assay to evaluate cell viability of HCC cells after exposure to the erlotinib derivatives of the present invention (EMQA) at the indicated doses for 48 hours. As shown in FIG. 6A, EMQA caused significant reduction in cell viability in all the HCC cell lines tested, including PLC5, HuH7, Hep3B and Sk-Hep1. To further examine the pro-apoptotic effects induced by the treatment, all four HCC cell lines were exposed to EMQA at the indicated concentration for 24 hours and analyzed by flow cytometry, cell death ELISA and western blot, and DMSO-treated as vehicle. The percentages of sub-G1 cells detected by flow cytometry increased in correspondence to both higher doses and longer duration of EMQA treatments (FIG. 6B and FIG. 6D, upper panel). The extent of DNA fragmentation shown by cell death ELISA was also significantly increased with higher doses of EMQA treatments (FIG. 6C). Notably, EMQA-induced-apoptosis of HCC cells corresponded to downregulation of p-Akt signaling in both a time- and does-dependent manners (FIG. 6D). Furthermore, the present invention used a PLC5 xenografted mouse model to assess the in vivo anti-HCC effects of EMQA. Compared with mice receiving vehicle, tumor-bearing mice treated with EMQA 10 mg/kg/day had significantly reduced tumor growth (FIG. 6E). To confirm the molecular events happened in the tumor tissue, the xenografted tumor from mice receiving EMQA and vehicle are analyzed by western blot and PP2A activity assay. In line with the data observed in vitro, p-Akt expression was much lower and the PP2A activity was significantly higher in the tumor lysate taken from mice receiving EMQA treatment than the vehicle (FIG. 6F).

Figure 7A:
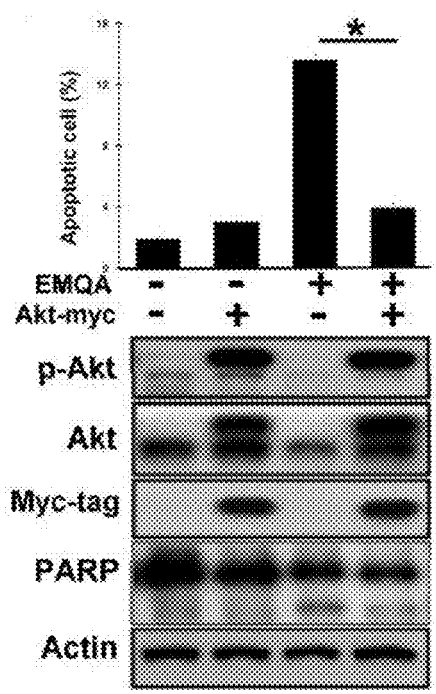
FIGS. 7A to 7F show enhancement of PP2A-mediated p-Akt downregulation by targeting SET determined the anti-tumor effects of EMQA.
Figure 7B:
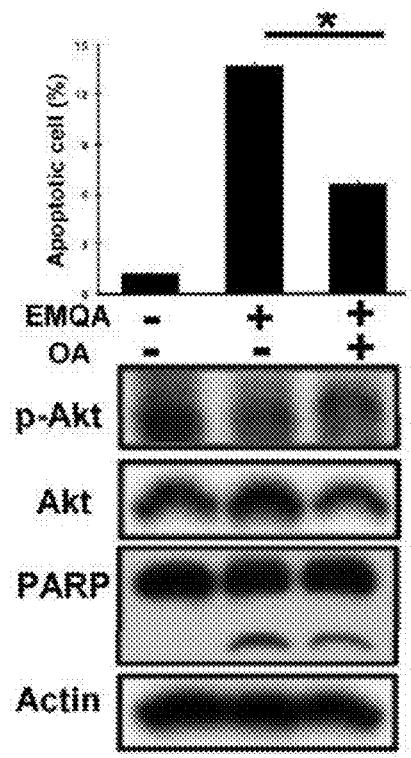
Figure 7C:
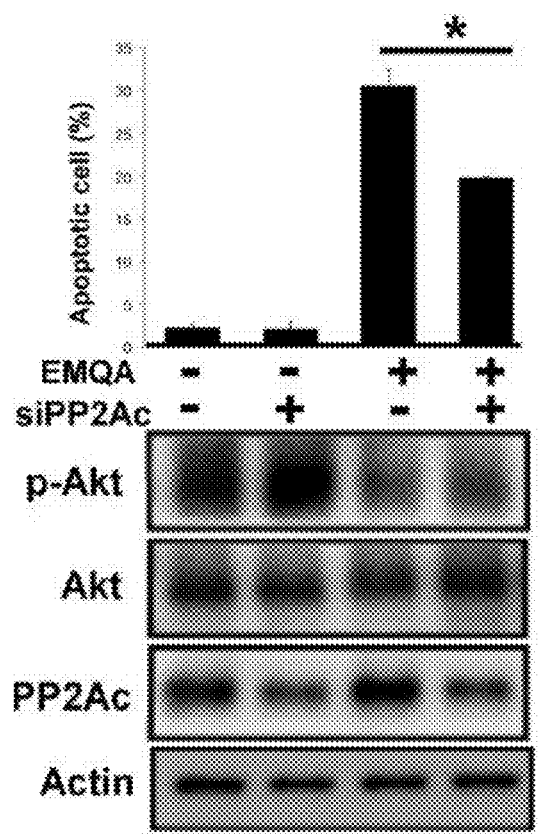
Figure 7D:
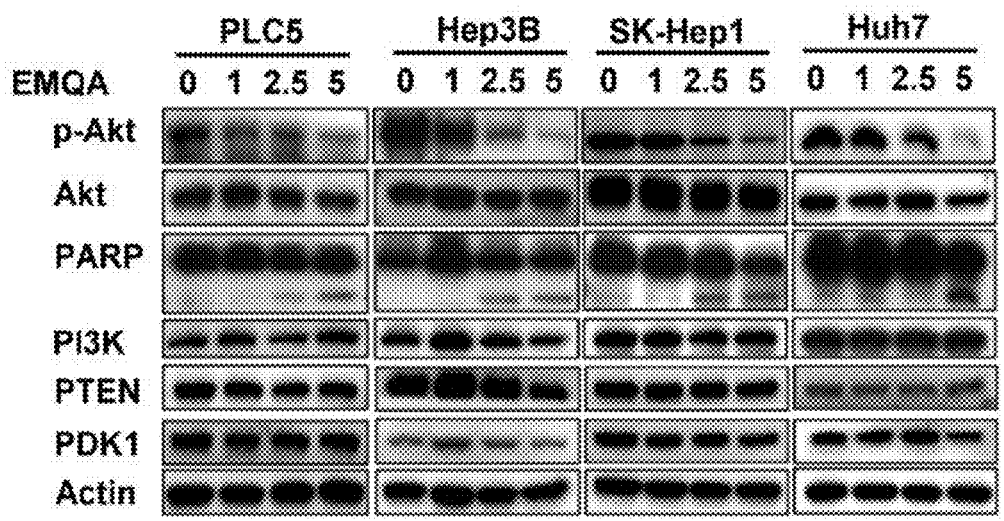

2.2.8 Inhibition of the SET/PP2A/p-Akt Signaling Determines the Pro-Apoptotic Effects of the Erlotinib Derivatives of the Present Invention The present invention next investigated whether Akt was vital in mediating the anti-HCC effects of EMQA. PLC5 cells with ectopic expression of myc-tagged Akt were generated by transient transfection and treated them with 5 μM EMQA for 24 hr. As shown in FIG. 7A, compared to wide-type cells, the percentage of sub-G1 cells and the cleaved forms of PARP after EMQA treatment were significantly reduced in the Akt overexpressing PLC5 cells, which indicated that Akt determines the pro-apoptotic effects of EMQA. Next, the present invention sought to validate the role of PP2A involved in EMQA-mediated Akt downregulation using three different strategies. First, a PP2A inhibitor, okadaic acid (OA) are used to suppress the PP2A activity. As shown in FIG. 7B, downregulation of p-Akt expression and pro-apoptotic effects induced by EMQA treatment were significantly reversed by co-treatment with 5 μM EMQA and 100 nM OA. Next, the present invention used siRNA to knock down PP2Ac more specifically. Compared to wide-type PLC5 cells, the expression of p-Akt was enhanced when PP2Ac was knocked down by siRNA (FIG. 7C). Moreover, the proportion of MQA-induced apoptotic cells was significantly reduced in these PP2Ac-knockdown-PCL5 cells. In addition to PP2A, other rotein kinases, including PI3K, PTEN and PDK1 have been reported to be involved in regulating the activation of Akt signaling. Therefore, the present invention checked the expression of these proteins in the EMQA-treated HCC cell lysates. As shown in FIG. 7D, EMQA treatment significantly inhibited the expressions of p-Akt, but the expression of PI3K, PTEN and PDK1 was not affected. These data indicated that PP2A plays the major role in mediating EMQA-induced Akt downregulation.

Figure 7E:
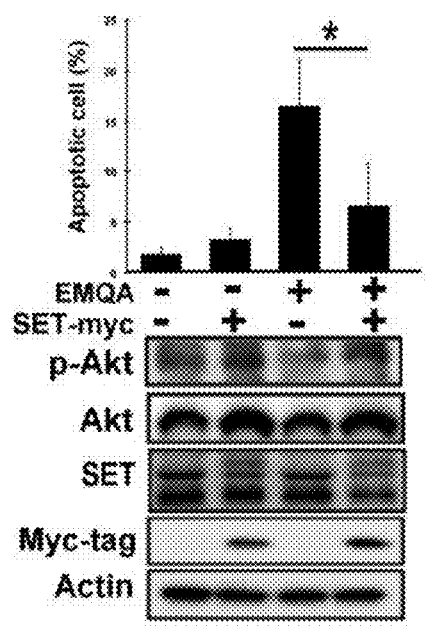
Figure 7F:
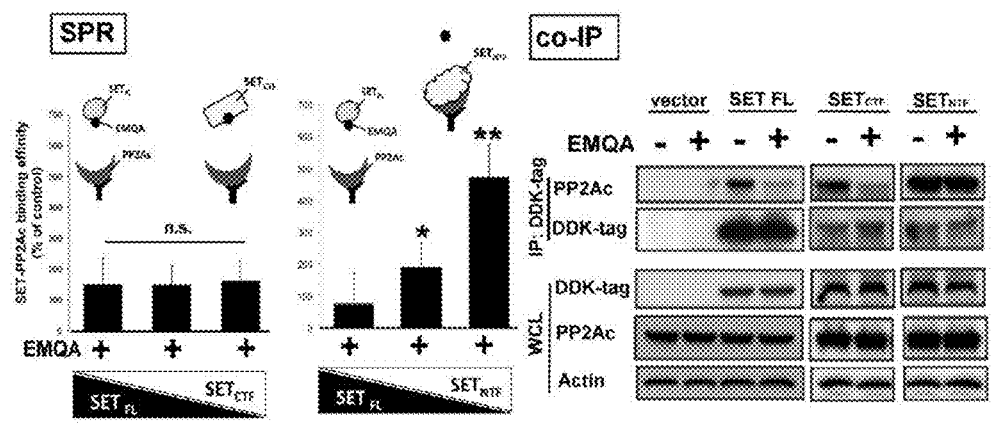

EMQA reactivates PP2A by disrupting the binding of SET-PP2Ac. To validate the role of SET, the present invention generated Hep3B cells with ectopic expression of myc-tagged SET by transient transfection. In these SET-overexpressing cells, EMQA treatment-induced downregulation of p-Akt and the apoptotic effects were also diminished (FIG. 7E). To elucidate the target site of EMQA, the present invention further generated two truncated SET proteins, the N-terminal fragment ($SET_{NTF}$, a.a. 1-227) and C-terminal fragment ($SET_{CTF}$, a.a. 76-277), and tested them in the ex vivo SPR system (FIG. 7F, left panel) and cell-based system (FIG. 7F, right panel). With a fixed amount of PP2Ac coated on the CM chip, the present invention tested the effects of a fixed-dose of EMQA on interfering different proportions of full-length and truncated forms of SET proteins in SPR system. As shown in FIG. 7F, the effects of EMQA were not affected by increasing proportion of $SET_{NTF}$. In contrast, the binding affinities of SET protein complex containing $SET_{NTF}$ and full-length SET to PP2Ac were increased with higher proportions of $SET_{NTF}$. To validate the findings of this ex vivo system, the present invention generated cells with ectopic overexpression of these two truncated forms of Flag-tagged SET proteins by transient transfections. Corresponding to the results of SPR, EMQA diminished the binding of full-length SET and $SET_{CTF}$, but not $SET_{NTF}$, to PP2Ac (FIG. 7F, right panel). Taken together, the present invention validated the same result in lung cancer A549 cell line (data no show), the results suggested that EMQA targets the C-terminal of SET protein specifically.

Figure 8A:
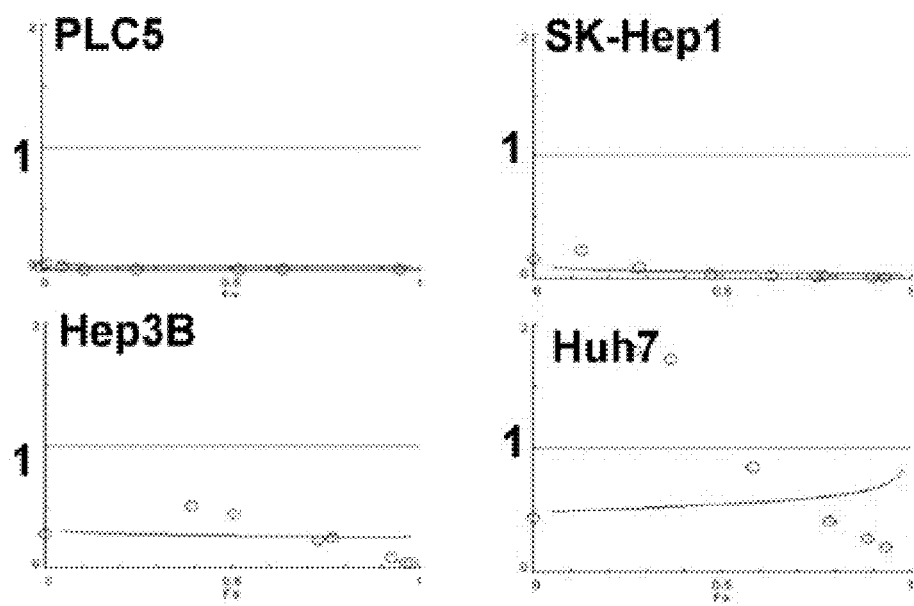
FIGS. 8A to 8E show that combination of sorafenib and EMQA showed synergism in vitro and in vivo anti-HCC effects.
Figure 8B:
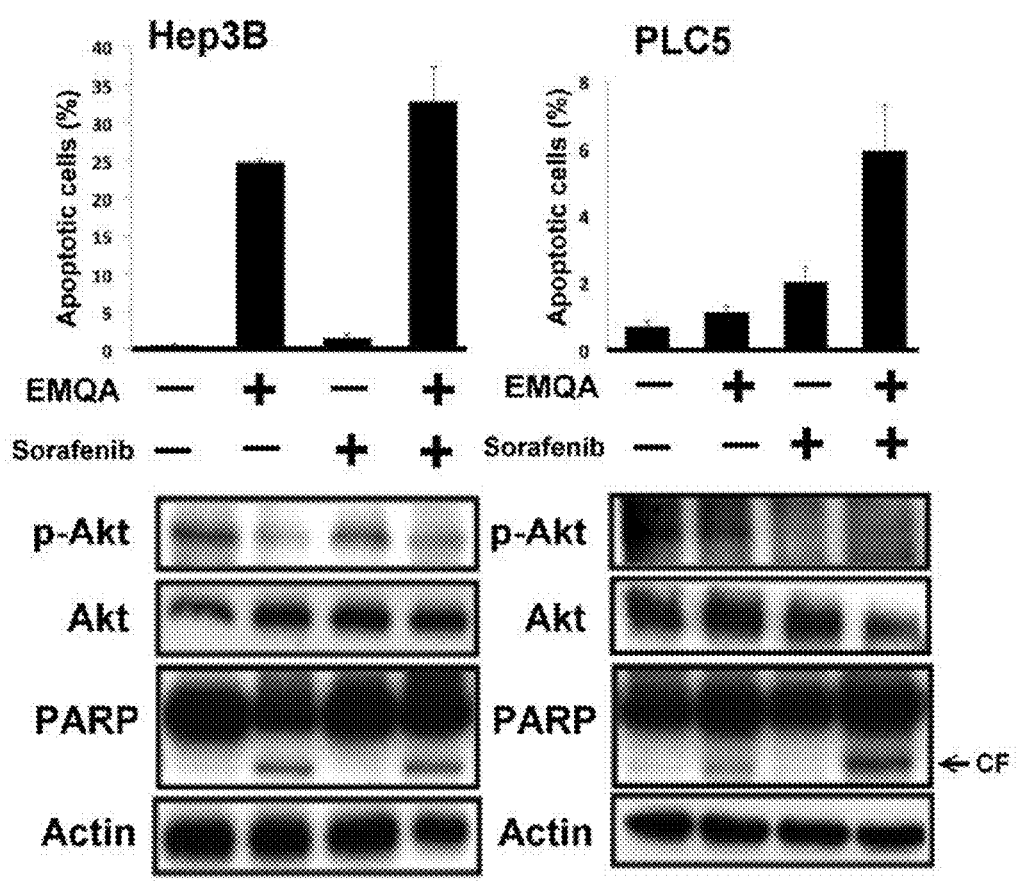
Figure 8C:
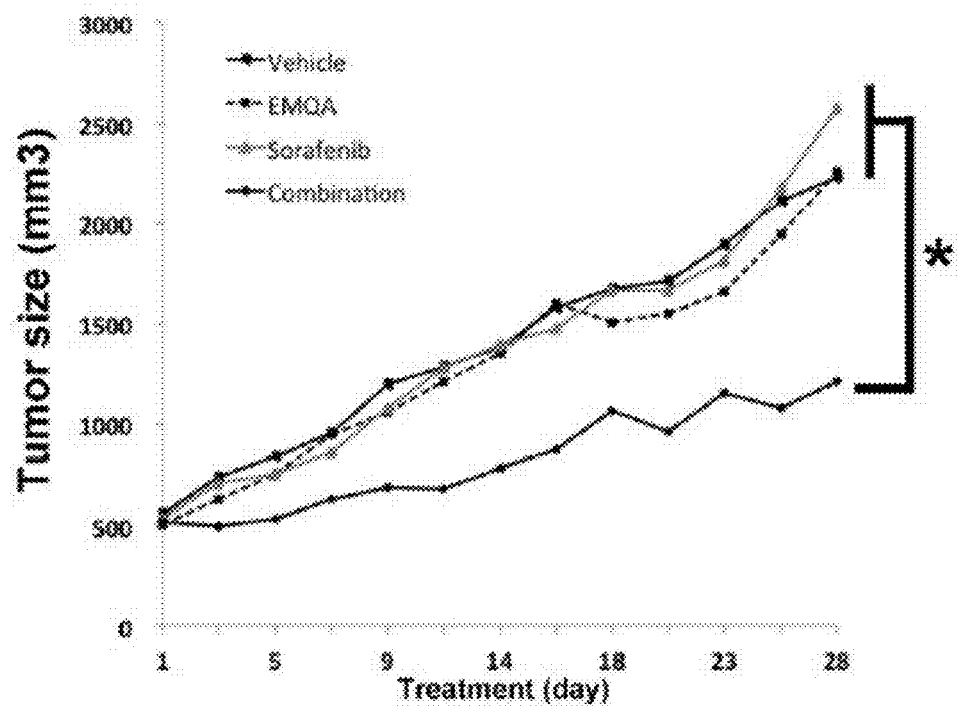
Figure 8D:
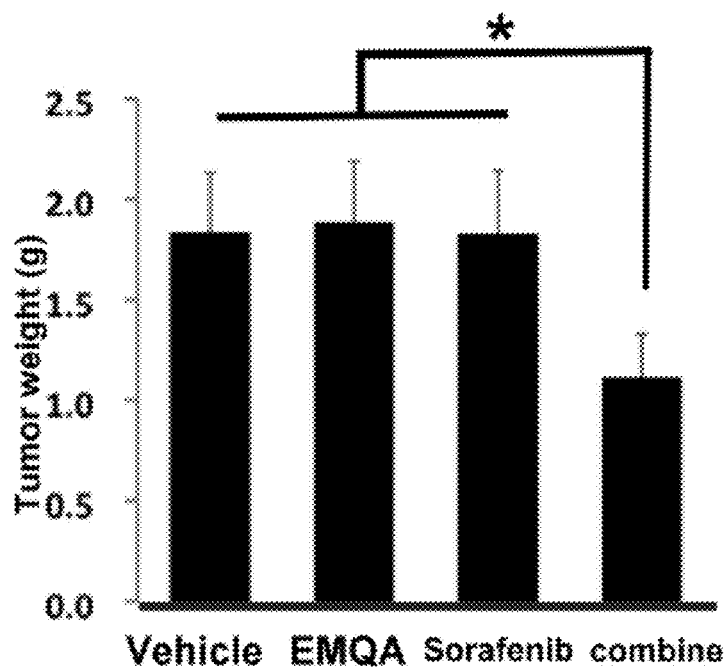
Figure 8E:
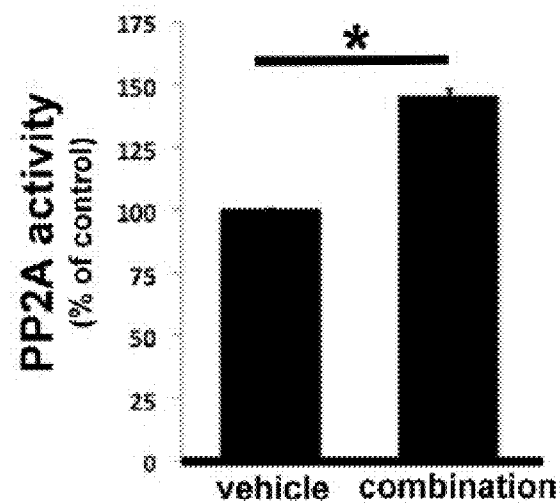
Figure 8E:
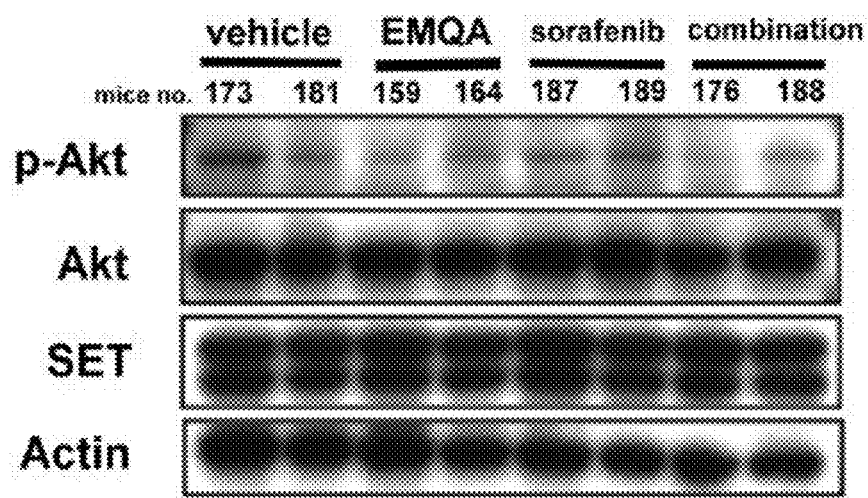
Figure 9A:
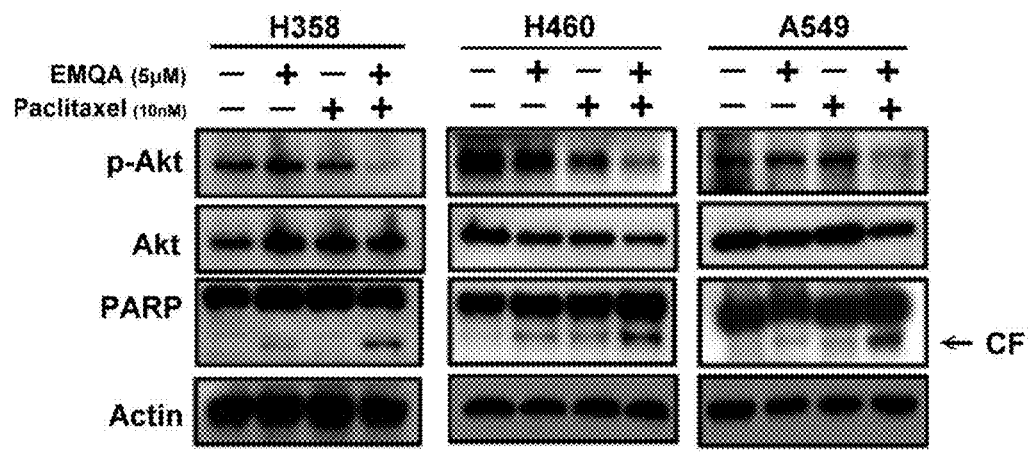
FIGS. 9A to 9D show that downregulation of p-Akt determines the synergism of EMQA and paclitaxel combination treatment.
Figure 9B:
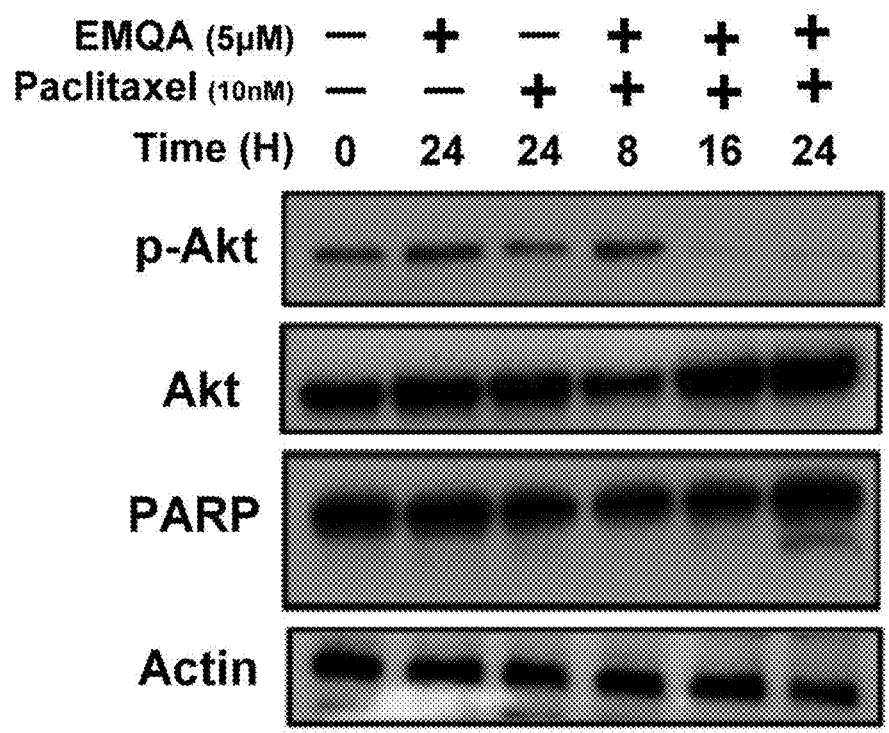
Figure 9C:
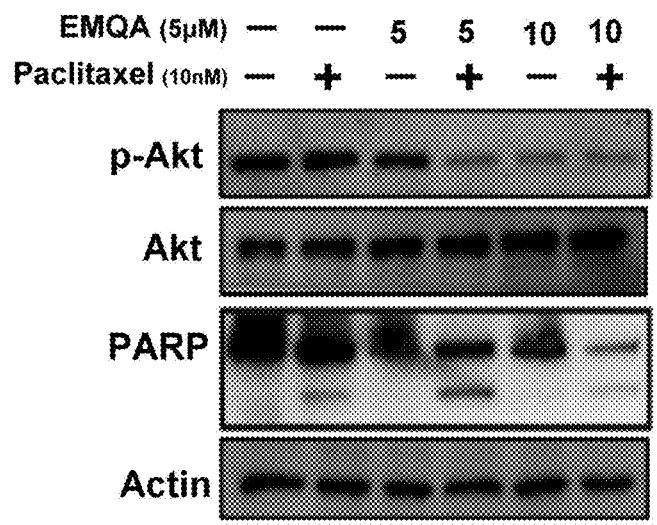
Figure 9D:
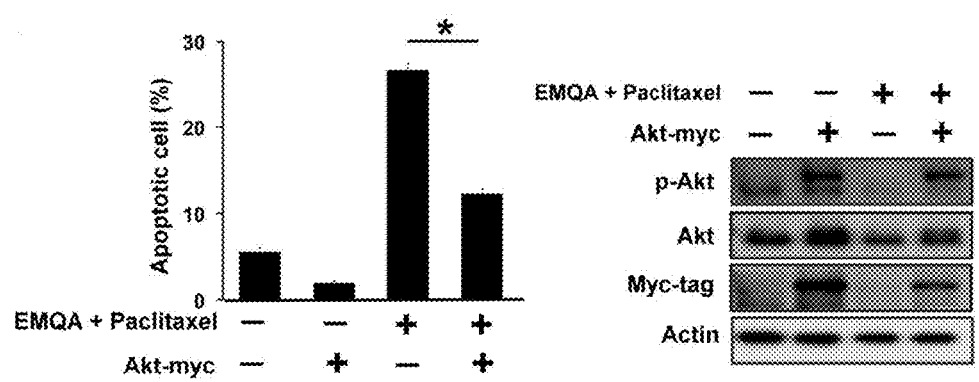

2.2.9 PP2A Functions Enhanced by the Erlotinib Derivatives of the Present Invention Improves the Sensitivities of HCC Cells to Sorafenib In Vitro and In Vivo So far, sorafenib is the only approved targeted therapy for patients with HCC. Owning to the limited progression-free survival and high level of treatment-associated toxicities, it is necessary to improve the drug sensitivity of sorafenib in HCC patients. To test whether reactivating PP2A could improve the effect of sorafenib, the present invention first used MTT assay to test the effects of combining EMQA and sorafenib. In the four different HCC cell lines, the anti-tumor effects were significantly improved when combining EMQA and sorafenib were used in combination at a ratio of 1:5. The combination indexes of all the HCC cell lines were determined by the results of MTT, which suggests synergism (FIG. 8A). The pro-apoptotic effects of this combination treatment were further characterized by sub-G1 assay and western blotting. Comparing treatment with sorafenib alone, the percentage of sub-G1 cells detected by flow cytometry and the cleaved forms of PARP were significantly increased when EMQA was added to sorafenib in Hep3B and PLC5 cells (FIG. 8B). Currently sorafenib is only indicated for patients with advanced HCC, whose tumors are often huge and not eligible for other local treatments. In order to mimic this clinical scenario, the present invention generated mice with larger PLC5 xenografted tumors and tested the effects of sorafenib and EMQA combination treatment. As shown in FIG. 8C, the tumor growth rate was significantly suppressed in the combination arm in comparison to mice receiving either EMQA or sorafenib alone. The average tumor weights of the tumor taken at the end of treatment were also significantly lower in the combination arm (FIG. 8D). Furthermore, this combination treatment also enhanced PP2A activity (FIG. 8E, upper panel) and suppressed p-Akt expressions in tumors 2.2.10 Co-Treatment with the Erlotinib Derivatives of the Present Invention and Paclitaxel Downregulate the Expression of p-Akt and Promotes Apoptotic Death of NSCLC The present invention analyzed the cell lysate treated with paclitaxel and/or EMQA by western blot. As shown in FIG. 9A, the expression of p-Akt was significantly decreased in all the lung cancer cell lines treated with EMQA and paclitaxel. Furthermore, co-treatment-induced downregulation of p-Akt was shown in a dose- and time-dependent manner (FIGS. 9B and 9C). Importantly, the activation of PARP signaling corresponded to downregulation of p-Akt. To further validate the role of Akt, the present invention generated A549 cells with ectopic expression of myc-tagged Akt by transient transfection and treated them with 1 μL EMQA and 10 nM paclitaxel. As shown in FIG. 9D, the efficacies of co-treatment were significantly reduced in the Akt-overexpressed cells. Therefore, the inhibition of Akt signaling determines the synergistic effects of EMQA and paclitaxel in NSCLC cells.

Figure 10A:
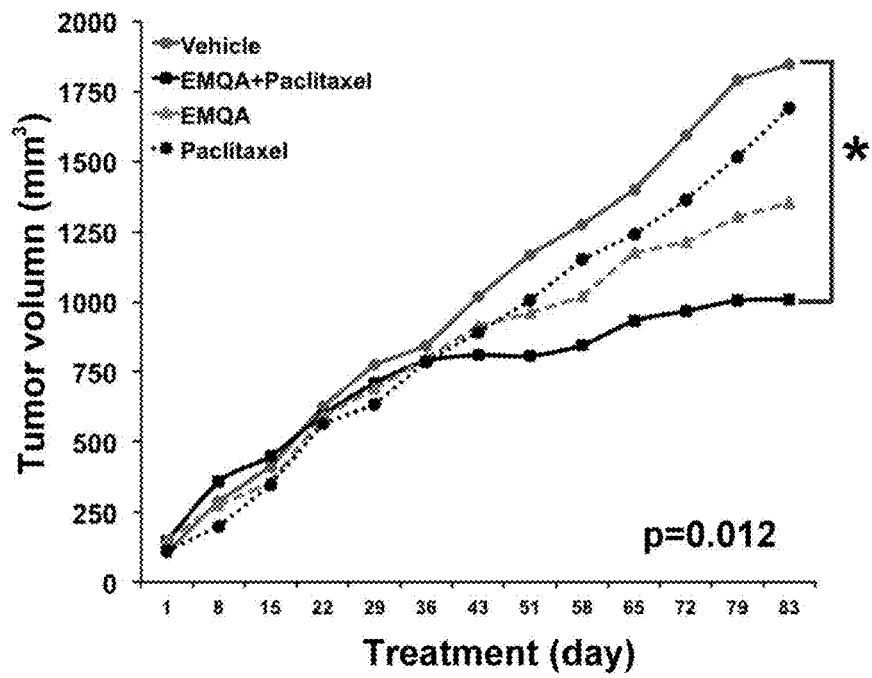
FIGS. 10A to 10E show the in-vivo anti-tumor effects of paclitaxel and EMQA combination treatment.
Figure 10B:
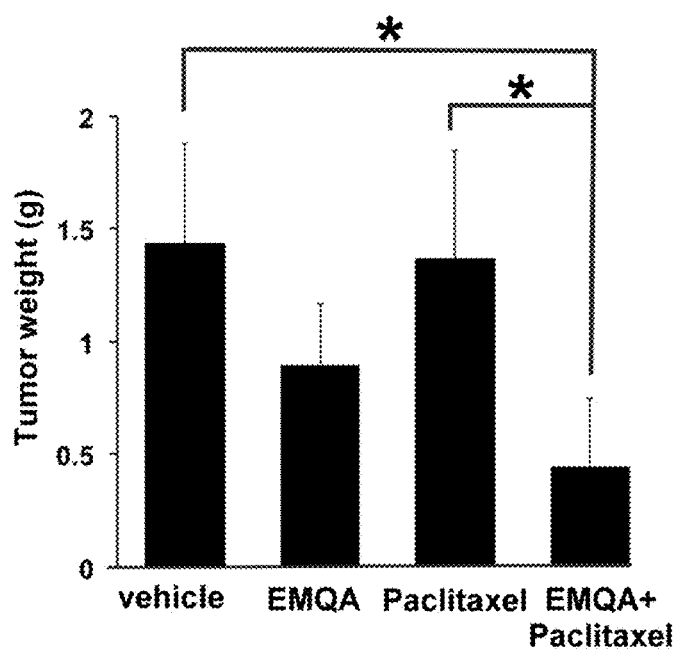
Figure 10C:
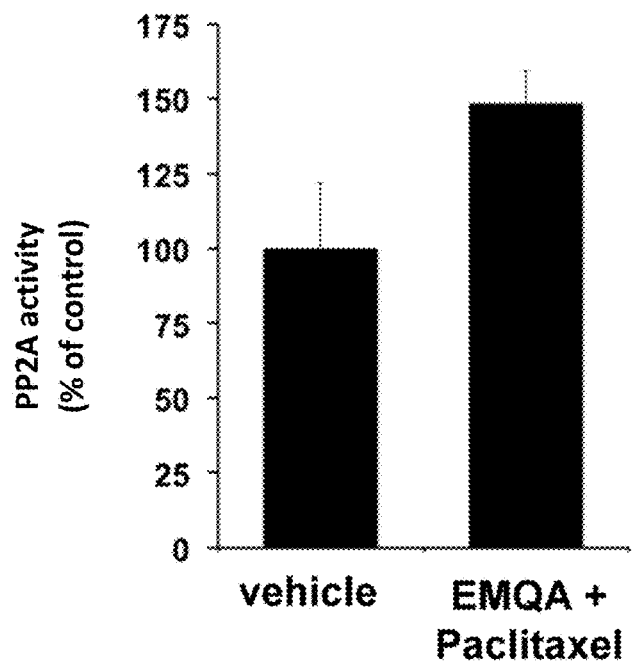
Figure 10D:
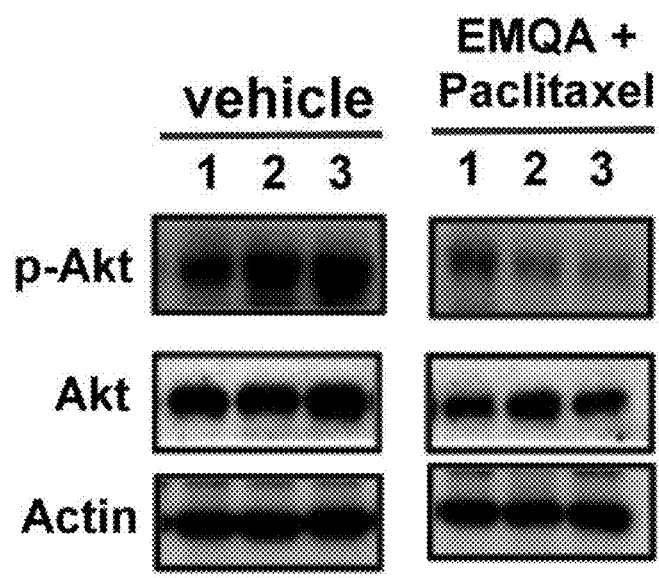
Figure 10E:
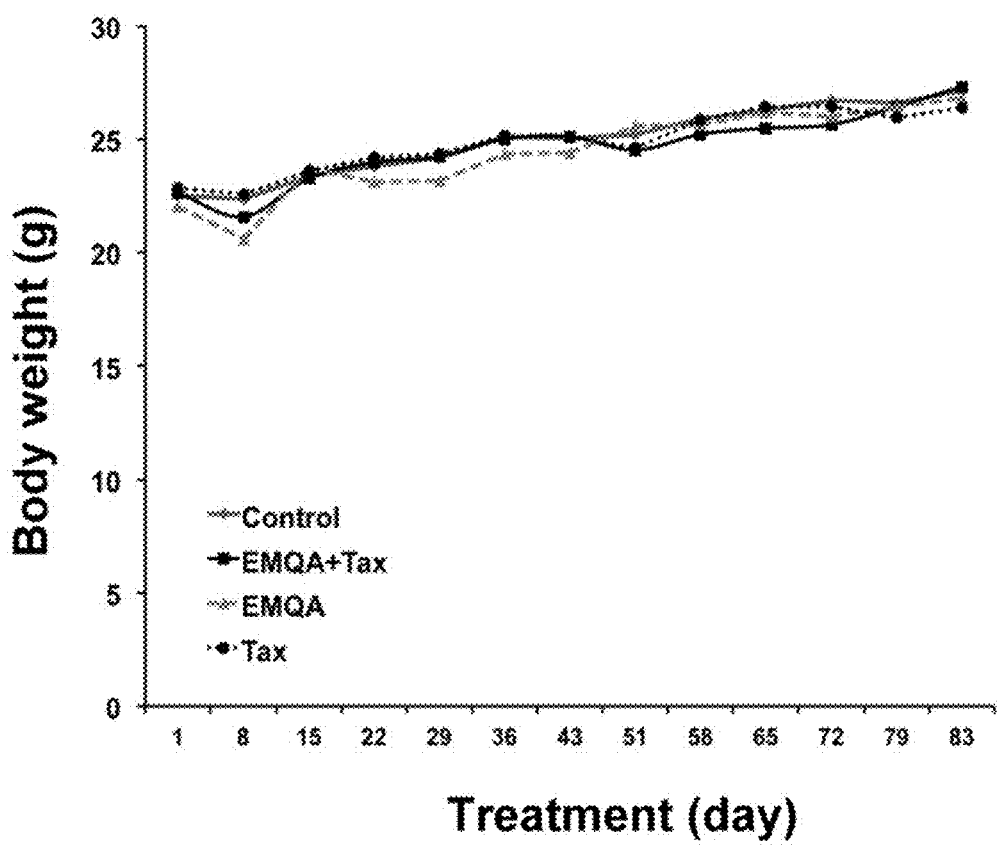

2.2.11 In Vivo Synergistic Anti-Cancer Effects of the Erlotinib Derivatives of the Present Invention and Paclitaxel To test the in vivo anti-tumor effects of combining EMQA and paclitaxel, the present invention generated an A549 xenografted mouse model and treated mice with vehicle, paclitaxel and/or EMQA. Compared to mice receiving EMQA or paclitaxel alone, the tumor growth rate of mice receiving paclitaxel and EMQA was significantly reduced (FIG. 10A). The average tumor weight of mice receiving combination treatment measured at the end of study of was much lower than mice in other treatment arms (FIG. 10B). Notably, there was no obvious difference in the body weights of mice exposed to different treatments (FIG. 10E). The present invention also analyzed the tumor lysate by western blot and PP2A activity assay. In concordance with previous results, the PP2A activity in tumors taken from mice receiving combination therapy were significantly higher than those receiving vehicle (FIG. 10C), and their expressions of p-Akt were also downregulated; the present invention analyzed the tumor lysate by western blot of the expression of p-Akt and Akt in A549 xenografted tumor lysate (FIG. 10D).

Accordingly, the erlotinib derivatives of the present invention demonstrate their new novel therapeutic mechanism in tumor cells, that is, enhancement of PP2A-dependent p-Akt downregulation by inhibition of CIP2A. These results suggest that the erlotinib derivatives of the present invention increasing the activity of PP2A may be a cancer therapy. Also, the present invention validates that SET overexpression is associated with patients with advanced cancer and poor prognosis, therefore, the present invention suggest that SET-PP2A binding can be a novel strategy for cancer therapy, and the combination of the erlotinib derivatives of the present invention and sorafenib or paclitaxel can enhance the therapy effect of sorafenib and inhibit tumor growth. The present invention provides an alternative cancer therapy, which is very helpful to the patients resistant to traditional medicine therapy.

TABLE 5

The erlotinib derivatives of the present invention effectively promote cancer cell death

| compound | NCI-1703 cell viability(%) 1 (uM) | 10 (uM) | IC50 | NCI-H226 cell viability(%) 1 (uM) | 10 (uM) | A549 cell viability(%) 1 (uM) | 10 (uM) | H358 cell viability(%) 1 (uM) | 10 (uM) | H2170 cell viability (%) 1 (uM) | 10 (uM) |
|---|---|---|---|---|---|---|---|---|---|---|---|
| TD52 | 84.7 ± 2.5 | 10.1 ± 0.1 | 3.8 | 79.5 ± 6.9 | 5.3 ± 0.1 | 71.5 ± 6.0 | 9.7 ± 0.9 | 99.8 ± 3.8 | 11.2 ± 0.7 | 100.46 ± 3.21 | 7.84 ± 9.49 |
| TD53 | 68.4 ± 1.4 | 46.7 ± 0.2 | 7.4 | 86.2 ± 5.7 | 56.8 ± 2.7 | 99.4 ± 6.9 | 82.7 ± 99.9 | 119.5 ± 9.2 | 41.9 ± 3.9 | 99.71 ± 6.00 | 59.19 ± 1.25 |
| TD54 | 127.2 ± 2.0 | 96.7 ± 4.2 | | 120.0 ± 4.9 | 110.9 ± 4.9 | | | | | 100.24 ± 4.93 | 79.08 ± 7.69 |
| TD55 | 64.2 ± 5.3 | 49.9 ± 4.8 | 8.3 | 106.5 ± 17.3 | 96.4 ± 7.4 | 100.1 ± 7.2 | 36.5 ± 5.9 | 109.5 ± 14.2 | 42.1 ± 0.6 | 102.73 ± 0.73 | 94.80 ± 6.05 |
| TD56 | 49.9 ± 4.7 | 28.8 ± 2.3 | | 115.4 ± 0.8 | 19.0 ± 2.0 | | | | | 95.00 ± 0.91 | 32.46 ± 14.08 |
| TD57 | 48.1 ± 4.5 | 31.4 ± 2.6 | | 90.0 ± 1.5 | 33.6 ± 1.7 | | | | | 93.86 ± 1.12 | 67.41 ± 3.86 |
| TD58 | 126.7 ± 2.9 | 98.9 ± 1.1 | | 123.2 ± 3.6 | 74.9 ± 1.5 | | | | | 92.85 ± 2.03 | 83.02 ± 3.41 |
| TD59 | 113.6 ± 7.4 | 26.4 ± 0.7 | | 121.7 ± 2.6 | 32.5 ± 2.5 | 164.6 ± 0.1 | 24.1 ± 3.9 | 117.3 ± 12.1 | 19.0 ± 1.5 | 88.41 ± 2.01 | 8.96 ± 1.43 |
| TD60 | 51.9 ± 2.9 | 26.1 ± 0.8 | | 92.5 ± 1.7 | 15.9 ± 1.0 | 91.3 ± 4.0 | 21.8 ± 1.4 | 55.3 ± 1.9 | 18.1 ± 1.3 | 72.32 ± 0.89 | 0.41 ± 0.65 |
| TD61 | 31.1 ± 1.6 | 8.5 ± 0.3 | 0.3 | 52.5 ± 3.4 | 20.9 ± 2.8 | 39.1 ± 5.8 | 18.6 ± 1.2 | 39.9 ± 1.2 | 20.6 ± 1.5 | 96.17 ± 2.24 | 32.37 ± 13.01 |
| TD62 | 111.6 ± 3.6 | 65.2 ± 0.6 | | 86.0 ± 2.0 | 90.1 ± 8.2 | 165.6 ± 23.1 | 120.1 ± 29 | 121.3 ± 2.2 | 97.4 ± 8.1 | 92.55 ± 1.41 | 85.34 ± 4.56 |
| TD63 | 54.5 ± 5.5 | 28.8 ± 7.9 | | 99.9 ± 4.3 | 19.6 ± 0.4 | 79.2 ± 7.8 | 21.9 ± 2.2 | 66.8 ± 8.5 | 16.2 ± 1.3 | 78.45 ± 1.28 | 9.13 ± 0.63 |
| TD64 | 85.1 ± 1.3 | 81.5 ± 10.4 | | 95.6 ± 4.9 | 89.3 ± 3.6 | 107.3 ± 10.8 | 92.3 ± 8.1 | 69.1 ± 9.0 | 57.0 ± 11.9 | 109.11 ± 1.85 | 99.92 ± 3.86 |
| TD65 | 53.2 ± 2.3 | 26.3 ± 1.0 | | 46.2 ± 2.5 | 14.1 ± 1.3 | 66.4 ± 6.9 | 27.7 ± 2.0 | 27.1 ± 1.2 | 18.3 ± 3.0 | 77.88 ± 3.48 | 0.26 ± 0.10 |
| TD66 | 84.5 ± 2.3 | 10.1 ± 0.2 | | 71.2 ± 1.2 | 4.7 ± 0.1 | 55.5 ± 5.1 | 11.1 ± 0.6 | 96.6 ± 0.9 | 14.9 ± 3.0 | 111.50 ± 0.48 | 3.70 ± 1.37 |
| TD67 | 22.3 ± 4.2 | 11.2 ± 0.0 | | 88.3 ± 2.4 | 7.3 ± 0.7 | 94.7 ± 5.9 | 20.9 ± 2.3 | 115.9 ± 23.4 | 26.4 ± 2.5 | 113.64 ± 2.52 | 33.63 ± 0.16 |
| TD68 | 48.6 ± 2.0 | 33.3 ± 7.1 | | 40.2 ± 0.3 | 14.8 ± 0.3 | 57.3 ± 19.1 | 32.9 ± 4.0 | 22.4 ± 1.8 | 16.7 ± 0.8 | 69.39 ± 0.67 | 0.17 ± 0.16 |
| TD69 | 52.2 ± 4.5 | 15.5 ± 0.4 | 1 | 69.0 ± 1.0 | 28.0 ± 1.5 | 71.4 ± 6.3 | 9.9 ± 0.7 | 102.9 ± 5.2 | 12.7 ± 0.4 | 116.44 ± 6.86 | 89.28 ± 2.49 |
| TD70 | 73.2 ± 5.1 | 59.7 ± 7.4 | >10 | 106.1 ± 5.7 | 123.4 ± 13.1 | 103.3 ± 22.8 | 91.9 ± 21.8 | 131.7 ± 4.3 | 116.6 ± 6.4 | 92.42 ± 3.67 | 86.44 ± 5.11 |
| TD71 | 85.1 ± 5.6 | 47.0 ± 8.6 | 8.6 | 118.3 ± 14.6 | 112.5 ± 8.5 | 97.6 ± 8.2 | 96.9 ± 9.3 | 123.3 ± 6.1 | 114.0 ± .1 | 110.87 ± 9.77 | 104.21 ± 3.99 |

| Compound | H520 cell viability (%) 1 (uM) | 10 (uM) | SW900 cell viability (%) 1 (uM) | 10 (uM) | BA (%) | minimal concentration to disrupt SET-PP2Ac binding (nM) | minimal concentration for PP2A activation (nM) |
|---|---|---|---|---|---|---|---|
| TD52 | 95.77 ± 1.26 | 13.96 ± 0.14 | 107.22 ± 13.13 | 77.91 ± 11.33 | | | |
| TD53 | 101.65 ± 0.34 | 10.57 ± 0.58 | 121.06 ± 9.01 | −8.01 ± 1.03 | | | |
| TD54 | 118.31 ± 3.00 | 101.71 ± 1.46 | 125.42 ± 27.03 | 126.15 ± 10.56 | | | |
| TD55 | 89.92 ± 1.02 | 59.20 ± 15.85 | 100.49 ± 6.69 | 88.29 ± 1.29 | 87 | | 100-200 |
| TD56 | 98.40 ± 6.37 | 4.76 ± 0.24 | 117.78 ± 5.41 | 1.46 ± 3.60 | | | |
| TD57 | 98.29 ± 8.33 | 83.14 ± 2.22 | 101.58 ± 1.03 | 97.75 ± 34.24 | | | |
| TD58 | 96.23 ± 1.22 | 95.63 ± 4.66 | 111.41 ± 1.54 | 91.75 ± 9.78 | | | |
| TD59 | 88.29 ± 1.50 | 0.41 ± 0.32 | 109.77 ± 1.80 | −2.91 ± 4.12 | | | |
| TD60 | 21.80 ± 1.52 | 0.36 ± 0.18 | 19.30 ± 6.18 | −1.27 ± 6.44 | | | 100-200 |
| TD61 | 54.05 ± 6.39 | 1.71 ± 0.60 | 107.77 ± 9.78 | −4.00 ± 2.57 | | <100 | |
| TD62 | 103.35 ± 1.70 | 100.47 ± 2.46 | 128.34 ± 1.80 | 127.79 ± 6.18 | | | |
| TD63 | 28.54 ± 0.58 | 0.45 ± 0.14 | 54.79 ± 3.35 | 3.28 ± 4.63 | | <100 | 50-100 |
| TD64 | 112.59 ± 7.51 | 91.41 ± 5.43 | 87.67 ± 3.31 | 57.86 ± 12.36 | | | |
| TD65 | 18.49 ± 1.23 | 0.47 ± 0.06 | 0.73 ± 1.32 | −1.61 ± 3.75 | 22 | <100 | 100-200 |
| TD66 | 103.95 ± 8.53 | 51.71 ± 20.46 | 112.64 ± 4.64 | 77.37 ± 20.53 | | | |
| TD67 | 92.11 ± 4.86 | 1.10 ± 0.28 | 71.44 ± 12.58 | 9.16 ± 1.77 | 5.1 | | |

TABLE 5-continued

The erlotinib derivatives of the present invention effectively promote cancer cell death

| Compound 1 (uM) | NCI-1703 cell viability(%) | | | NCI-H226 cell viability (%) | | A549 cell viability(%) | | H358 cell viability(%) | | H2170 cell viability(%) | |
|---|---|---|---|---|---|---|---|---|---|---|---|
| | 10 (uM) | IC50 | 1 (uM) | 10 (uM) | 1 (uM) | 10 (uM) | 1 (uM) | 10 (uM) | 1 (uM) | 10 (uM) | |
| TD68 | 10.08 ± 0.85 | 0.47 ± 0.11 | | | | | | | | | |
| TD69 | 51.72 ± 2.99 | 13.13 ± 3.12 | | 3.38 ± 4.64 | 0.57 ± 0.22 | | | | 50 | | <50 |
| TD70 | 102.17 ± 1.21 | 93.55 ± 2.61 | | 108.90 ± 18.32 | 42.40 ± 1.10 | | | | | | |
| TD71 | 100.50 ± 1.82 | 92.95 ± 4.48 | | 105.93 ± 5.74 | 86.58 ± 5.30 | | | | | | |
| | | | | 112.17 ± 1.32 | 106.87 ± 21.63 | | | | | | |
| TD72 | 87.9 ± 3.9 | 92.7 ± 7.1 | | 95.7 ± 2.5 | 93.9 ± 1.6 | 101.4 ± 3.4 | 108.5 ± 5.6 | 120.7 ± 21.3 | 123.1 ± 5.5 | 115.40 ± 0.54 | 107.57 ± 1.15 |
| TD73 | 112.5 ± 2.9 | 60.9 ± 2.5 | | 90.4 ± 1.8 | 76.6 ± 1.5 | 66.0 ± 43.1 | 70.8 ± 11.2 | 122.1 ± 4.6 | 105.8 ± 9.1 | 92.13 ± 4.47 | 79.46 ± 3.93 |
| TD74 | 82.9 ± 4.4 | 64.6 ± 2.5 | | 93.0 ± 3.8 | 84.2 ± 1.9 | 92.3 ± 8.7 | 69.6 ± 25.0 | 133.6 ± 2.4 | 111.1 ± 6.6 | 84.02 ± 0.67 | 84.02 ± 0.67 |
| TD75 | 125.4 ± 1.1 | 48.3 ± 1.8 | | 101.9 ± 4.2 | 86.8 ± 2.8 | 93.2 ± 8.7 | 90.2 ± 18.4 | 111.1 ± 3.6 | 92.0 ± 11.1 | 113.46 ± 2.27 | 90.21 ± 2.39 |
| TD76 | 101.9 ± 8.4 | 63.5 ± 3.6 | | 134.3 ± 1.2 | 49.9 ± 7.4 | 96.5 ± 19.7 | 74.7 ± 20.3 | 109.4 ± 13.4 | 83.2 ± 0.4 | 94.39 ± 1.84 | 78.26 ± 1.47 |
| TD77 | 108.1 ± 3.6 | 90.5 ± 2.3 | | 126.0 ± 13.0 | 119.7 ± 6.6 | 86.4 ± 3.2 | 81.1 ± 6.0 | 105.2 ± 6.8 | 95.0 ± 6.4 | 96.01 ± 4.18 | 100.58 ± 0.54 |
| TD78 | 70.6 ± 8.2 | 73.2 ± 14.1 | | 117.6 ± 2.2 | 110.6 ± 12.9 | 77.6 ± 5.8 | 94.7 ± 11.3 | 98.7 ± 4.6 | 90.8 ± 7.4 | 110.84 ± 1.69 | 93.09 ± 0.66 |
| TD79 | 123.7 ± 0.9 | 64.8 ± 4.5 | | 130.6 ± 14.3 | 125.3 ± 10.5 | 96.5 ± 4.4 | 71.6 ± 10.1 | 113.8 ± 2.4 | 87.7 ± 1.8 | 98.50 ± 1.56 | 101.56 ± 5.66 |
| TD80 | 106.3 ± 5.2 | 52.3 ± 2.4 | | 103.1 ± 10.7 | 87.8 ± 9.3 | 109.6 ± 6.0 | 83.4 ± 16.4 | 118.9 ± 3.7 | 89.4 ± 11.9 | 91.56 ± 5.42 | 87.56 ± 0.78 |
| TD81 | 82.7 ± 5.0 | 85.8 ± 0.1 | | 100.3 ± 4.1 | 92.0 ± 3.8 | 95.6 ± 15.9 | 69.4 ± 3.4 | 115.7 ± 5.9 | 75.5 ± 3.9 | 100.24 ± 6.20 | 82.69 ± 2.44 |
| TD82 | 74.0 ± 7.0 | 97.8 ± 1.6 | | 102.5 ± 7.8 | 105.3 ± 18.3 | 113.0 ± 4.3 | 71.3 ± 4.4 | 112.8 ± 2.2 | 73.6 ± 1.6 | 90.60 ± 3.88 | 85.66 ± 0.75 |
| TD83 | 25.1 ± 2.2 | 24.9 ± 5.0 | 0.1 | 32.9 ± 0.2 | 6.8 ± 0.2 | 58.3 ± 3.7 | 12.3 ± 0.6 | 13.6 ± 0.8 | 13.6 ± 0.8 | | |
| TD84 | 28.6 ± 2.7 | 20.8 ± 3.3 | 0.02 | 24.9 ± 1.2 | 9.5 ± 0.1 | 22.0 ± 16.0 | 19.2 ± 7.6 | 11.5 ± 1.0 | 11.5 ± 1.0 | | |
| TD85 | 31.7 ± 2.2 | 13.9 ± 03 | | 21.5 ± 2.8 | 11.6 ± 2.0 | | | 20.4 ± 8.1 | 11.2 ± 1.9 | | |
| TD86 | 33.9 ± 0.6 | 13.0 ± 0.3 | | 23.5 ± 2.0 | 10.5 ± 1.2 | | | 34.7 ± 2.0 | 9.1 ± 1.2 | | |
| TD87 | 110.04 ± 1.20 | 103.58 ± 0.78 | | 20.1 ± 1.3 | 10.6 ± 1.0 | | | 18.8 ± 7.8 | 8.7 ± 0.7 | | |
| TD88 | 49.4 ± 3.6 | 12.7 ± 0.8 | | 21.1 ± 4.0 | 11.2 ± 2.3 | | | 44.7 ± 3.7 | 9.1 ± 1.2 | | |
| TD89 | 34.9 ± 3.8 | 27.3 ± 10.1 | 0.4 | 46.0 ± 2.1 | 7.4 ± 0.2 | 62.9 ± 6.8 | 12.4 ± 0.3 | 25.5 ± 2.9 | 11.6 ± 0.4 | | |
| TD90 | 31.2 ± 6.0 | 21.0 ± 3.8 | 0.1 | 32.7 ± 0.1 | 7.1 ± 0.4 | 59.6 ± 7.1 | 10.7 ± 0.2 | 12.6 ± 0.7 | 12.1 ± 3.6 | | |
| TD91 | 48.1 ± 3.7 | 21.2 ± 2.4 | 0.9 | 45.6 ± 2.4 | 8.5 ± 0.4 | 85.5 ± 6.0 | 13.6 ± 0.5 | 58.0 ± 1.4 | 13.1 ± 2.5 | | |
| TD92 | 27.7 ± 7.8 | 20.6 ± 0.5 | 0.1 | 10.3 ± 0.4 | 7.8 ± 0.2 | 15.3 ± 1.9 | 13.5 ± 2.1 | 14.9 ± 0.7 | 14.4 ± 4.2 | | |

| Compound 1 (uM) | H520 cell viability (%) | | SW900 cell viability (%) | | BA (%) | minimal concentration to disrupt SET-PP2Ac binding (nM) | minimal concentration for PP2A activation (nM) |
|---|---|---|---|---|---|---|---|
| | 10 (uM) | | 1 (uM) | 10 (uM) | | | |
| TD72 | 105.38 ± 0.83 | 102.66 ± 0.89 | 111.71 ± 7.28 | 115.30 ± 2.21 | | >200 | >200 |
| TD73 | 106.85 ± 2.40 | 79.72 ± 39.07 | 106.56 ± 6.62 | 99.06 ± 20.75 | | >200 | >200 |
| TD74 | 93.57 ± 2.50 | 84.57 ± 5.22 | 105.15 ± 3.75 | 79.55 ± 15.23 | | >200 | >200 |
| TD75 | 103.56 ± 0.55 | 75.25 ± 5.50 | 104.84 ± 6.40 | 73.15 ± 3.09 | | >200 | >200 |
| TD76 | 107.85 ± 0.74 | 73.10 ± 2.56 | 107.10 ± 18.96 | 63.88 ± 6.02 | | | |
| TD77 | 110.04 ± 1.20 | 103.58 ± 0.78 | 113.72 ± 4.68 | 94.79 ± 1.12 | | | |
| TD78 | 108.50 ± 0.14 | 108.14 ± 2.23 | 101.58 ± 6.69 | 84.07 ± 1.12 | | 100-200 | >200 |
| TD79 | 96.63 ± 5.57 | 99.01 ± 6.01 | 98.90 ± 3.79 | 88.17 ± 19.85 | | | |
| TD80 | 104.50 ± 1.30 | 92.22 ± 4.42 | 99.84 ± 11.82 | 88.01 ± 13.38 | | >200 | >200 |
| TD81 | 103.39 ± 0.14 | 72.38 ± 11.34 | 86.91 ± 7.36 | 60.25 ± 11.15 | | >200 | >200 |
| TD82 | 98.76 ± 2.64 | 101.58 ± 8.73 | 100.47 ± 10.48 | 103.79 ± 19.18 | | >200 | >200 |
| TD83 | | | | | | | |
| TD84 | | | | | | | |
| TD85 | | | | | | | |
| TD86 | | | | | | | |

TABLE 5-continued

The erlotinib derivatives of the present invention effectively promote cancer cell death

| Compound | NCI-1703 cell viability(%) | | | NCI-H226 cell viability (%) | | A549 cell viability (%) | | H358 cell viability(%) | | H2170 cell viability (%) | |
|---|---|---|---|---|---|---|---|---|---|---|---|
| | 1 (uM) | 10 (uM) | IC50 | 1 (uM) | 10 (uM) | 1 (uM) | 10 (uM) | 1 (uM) | 10 (uM) | 1 (uM) | 10 (uM) |
| TD87 | | | | | | | | | | | |
| TD88 | | | | | | | | | | | |
| TD89 | | | | | | | | | | | |
| TD90 | | | | | | | | | | | |
| TD91 | | | | | | | | | | | |
| TD92 | | | | | | | | | | | |
| TD93 | 24.9 ± 0.4 | 26.0 ± 12.7 | 0.2 | 27.1 ± 2.5 | 8.4 ± 0.3 | 19.3 ± 1.1 | 11.1 ± 1.2 | 13.5 ± 0.8 | 12.3 ± 0.5 | | |
| TD94 | 29.9 ± 6.8 | 19.5 ± 1.1 | 0.1 | 32.1 ± 2.7 | 8.0 ± 0.1 | 49.0 ± 6.5 | 10.8 ± 0.9 | 13.0 ± 0.2 | 15.7 ± 5.9 | | |
| TD95 | 28.3 ± 0.6 | 17.9 ± 0.3 | 1.2 | 43.3 ± 0.7 | 8.2 ± 0.4 | 29.9 ± 5.4 | 11.8 ± 0.5 | 13.7 ± 1.2 | 11.7 ± 0.3 | | |
| TD601 | 46.3 ± 2.4 | 12.5 ± 0.3 | | 73.4 ± 5.2 | 8.4 ± 3.8 | 113.7 ± 10.7 | 116.0 ± 13.3 | 126.8 ± 5.7 | 124.2 ± 7.1 | 98.16 ± 1.93 | 6.46 ± 1.78 |
| TD602 | 42.0 ± 1.1 | 9.8 ± 0.0 | | 98.1 ± 5.9 | 8.1 ± 0.4 | 47.4 ± 2.4 | 10.0 ± 0.8 | 58.3 ± 9.2 | 12.0 ± 0.5 | 112.07 ± 3.97 | 7.14 ± 4.42 |
| TD603 | 16.2 ± 0.6 | 8.5 ± 0.2 | | 11.3 ± 0.4 | 6.7 ± 0.5 | 14.2 ± 0.6 | 9.8 ± 0.7 | 16.5 ± 0.6 | 12.4 ± 0.6 | 52.09 ± 21.88 | 9.95 ± 0.27 |
| TD604 | 15.2 ± 0.5 | 12.5 ± 0.3 | 0.6 | 40.3 ± 1.7 | 5.3 ± 0.3 | 116.6 ± 7.2 | 132.0 ± 5.1 | 114.7 ± 9.0 | 116.3 ± 8.5 | 74.71 ± 6.38 | 2.06 ± 0.66 |
| TD605 | 20.8 ± 0.4 | 13.8 ± 0.2 | 0.5 | 53.1 ± 1.9 | 5.5 ± 0.2 | 83.7 ± 7.0 | 113.2 ± 18.3 | 100.7 ± 13.6 | 113.3 ± 12.0 | 107.80 ± 3.88 | 5.53 ± 0.81 |
| TD606 | 27.5 ± 3.0 | 10.3 ± 0.4 | 1.1 | 88.8 ± 5.4 | 4.7 ± 0.0 | 53.3 ± 11.5 | 9.3 ± 1.4 | 106.0 ± 7.5 | 14.1 ± 0.5 | 99.65 ± 2.43 | 0.76 ± 0.16 |
| TD607 | 49.7 ± 2.7 | 13.4 ± 1.6 | 1.3 | 105.8 ± 2.6 | 36.7 ± 2.2 | 100.5 ± 5.9 | 9.5 ± 0.6 | 116.1 ± 15.5 | 12.1 ± 0.3 | 103.88 ± 14.19 | 1.34 ± 0.93 |
| TD608 | 52.8 ± 4.5 | 12.7 ± 0.9 | | 103.5 ± 2.5 | 40.6 ± 2.4 | 71.5 ± 35 | 10.3 ± 3.5 | 109.9 ± 44.0 | 31.7 ± 33.3 | 112.60 ± 8.63 | 4.71 ± 0.24 |
| TD609 | 61.0 ± 1.7 | 83.1 ± 2.5 | | 66.8 ± 13.8 | 75.8 ± 8.9 | 105.7 ± 17.0 | 105.4 ± 15.9 | 102.6 ± 5.1 | 107.3 ± 5.7 | 99.46 ± 1.32 | 100.46 ± 2.73 |
| TD610 | 74.8 ± 3.5 | 46.8 ± 2.5 | | 63.1 ± 9.9 | 74.1 ± 5.8 | 96.8 ± 16.8 | 94.3 ± 10. | 102.9 ± 1.7 | 106.5 ± 3.8 | 96.15 ± 1.40 | 82.13 ± 6.62 |
| TD611 | 77.7 ± 3.4 | 10.3 ± 0.3 | | 71.3 ± 5.8 | 71.8 ± 6.6 | 113.6 ± 15.7 | 123.2 ± 8.8 | 108.8 ± 5.3 | 111.0 ± 3.9 | 100.51 ± 1.32 | 49.18 ± 41.74 |
| TD612 | 82.7 ± 2.4 | 13.4 ± 0.7 | | 69.4 ± 6.8 | 38.0 ± 1.4 | 90.6 ± 18.2 | 10.3 ± 1.2 | 97.3 ± 13.4 | 12.8 ± 0.4 | 106.93 ± 4.84 | 22.51 ± 11.80 |
| TD613 | 86.0 ± 0.5 | 24.8 ± 2.0 | | 75.5 ± 7.9 | 7.0 ± 0.3 | 105.0 ± 3.4 | 9.5 ± 0.7 | 69.9 ± 60.7 | 12.0 ± 0.5 | 108.50 ± 1.99 | 11.62 ± 1.38 |
| TD614 | 116.3 ± 15.1 | 9.8 ± 1.0 | | 79.4 ± 11.6 | 44.4 ± 7.9 | 113.6 ± 1.6 | 12.4 ± 0.7 | 115.6 ± 7.0 | 12.8 ± 0.1 | 115.88 ± 5.96 | 31.88 ± 41.63 |
| TD615 | 40.4 ± 0.7 | 30.3 ± 1.0 | | 47.2 ± 0.6 | 16.9 ± 0.2 | 50.4 ± 2.4 | 20.9 ± 2.7 | 31.2 ± 3.5 | 24.4 ± 2.6 | | |
| TD616 | 116.2 ± 3.9 | 35.3 ± 4.6 | | 117.0 ± 6.3 | 22.1 ± 4.6 | 118.2 ± 2.2 | 24.7 ± 5.0 | 94.6 ± 10.5 | 27.9 ± 2.8 | | |
| TD617 | 127.4 ± 0.5 | 121.6 ± 6.0 | | 116.9 ± 8.6 | 112.0 ± 11.9 | 122.8 ± 5.5 | 133.4 ± 13.3 | 113.5 ± 5.6 | 110.6 ± 7.3 | | |

| Compound | H520 cell viability (%) | | SW900 cell viability(%) | | BA (%) | minimal concentration to disrupt SET-PP2Ac binding (nM) | minimal concentration for PP2A activation (nM) |
|---|---|---|---|---|---|---|---|
| | 1 (uM) | 10 (uM) | 1 (uM) | 10 (uM) | | | |
| TD93 | | | | | | | |
| TD94 | | | | | | | |
| TD95 | | | | | | | |
| TD601 | 96.72 ± 1.57 | 86.28 ± 7.70 | 103.31 ± 2.01 | 114.98 ± 15.39 | 87 | 50-100 | <50 |
| TD602 | 103.52 ± 2.31 | 0.89 ± 0.41 | 119.56 ± 5.80 | 2.05 ± 2.45 | 57 | 100-200 | 100-200 |
| TD603 | 14.03 ± 1.57 | 0.97 ± 0.45 | 68.77 ± 13.38 | 3.94 ± 2.45 | | >200 | >200 |
| TD604 | 30.51 ± 13.94 | 0.99 ± 0.02 | 86.12 ± 22.75 | 0.00 ± 1.34 | | >200 | >200 |
| TD605 | 89.11 ± 6.09 | 0.78 ± 0.39 | 87.07 ± 27.21 | 2.21 ± 1.34 | | >200 | >200 |
| TD606 | 103.72 ± 12.53 | 0.84 ± 0.31 | 99.15 ± 0.40 | 0.00 ± 1.34 | | | >100 |
| TD607 | 63.40 ± 53.69 | −0.06 ± 0.00 | 85.86 ± 10.40 | 0.61 ± 5.00 | | | >200 |
| TD608 | 96.95 ± 19.84 | 1.77 ± 1.70 | 114.00 ± 2.60 | 39.77 ± 51.18 | | | >100 |
| TD609 | 108.66 ± 0.59 | 111.95 ± 4.77 | 101.70 ± 3.20 | 105.66 ± 5.20 | | | >100 |
| TD610 | 109.73 ± 3.66 | 103.24 ± 4.23 | 105.37 ± 8.80 | 85.58 ± 6.00 | | | |

TABLE 5-continued

The erlotinib derivatives of the present invention effectively promote cancer cell death

|  | H520 cell viability (%) |  | NCI-1703 cell viability(%) |  |  | NCI-H226 cell viability(%) |  | A549 cell viability(%) |  | H358 cell viability(%) |  | H2170 cell viability(%) |  |
|---|---|---|---|---|---|---|---|---|---|---|---|---|---|
| Compound | 1 (uM) | 10 (uM) | 1 (uM) | 10 (uM) | IC50 | 1 (uM) | 10 (uM) | 1 (uM) | 10 (uM) | 1 (uM) | 10 (uM) | 1 (uM) | 10 (uM) |
| TD611 | 109.24 ± 1.61 | 40.91 ± 38.61 |  |  |  |  |  | 119.79 ± 6.80 | 10.23 ± 10.20 |  |  |  | >100 |
| TD612 | 107.19 ± 2.62 | 12.91 ± 1.20 |  |  |  |  |  | 104.95 ± 3.40 | 64.66 ± 4.00 |  |  |  | <100 |
| TD613 | 99.45 ± 0.50 | 18.78 ± 0.22 |  |  |  |  |  | 115.83 ± 7.20 | 80.91 ± 3.80 |  |  |  |  |
| TD614 | 106.57 ± 2.92 | 0.32 ± 0.31 |  |  |  |  |  | 111.03 ± 2.00 | 0.61 ± 1.80 |  |  |  | >200 |
| TD615 |  |  |  |  |  |  |  |  |  |  |  |  |  |
| TD616 |  |  |  |  |  |  |  |  | 11.2 |  | >200 |  |  |
| TD617 |  |  |  |  |  |  |  |  |  |  |  |  |  |
| TD618 | 48.3 ± 4.8 | 31.9 ± 5.0 |  |  |  | 49.6 ± 9.4 | 16.7 ± 1.1 | 53.2 ± 6.3 | 26.9 ± 7.0 | 36.6 ± 1.6 | 20.4 ± 3.5 |  |  |
| TD619 | 118.8 ± 11.2 | 33.6 ± 5.4 |  |  |  | 109.8 ± 18.2 | 19.5 ± 0.7 | 105.2 ± 19.5 | 20.9 ± 1.7 | 87.5 ± 3.6 | 22.1 ± 0.6 |  |  |
| TD620 | 26.2 ± 0.6 | 21.0 ± 1.7 |  |  | 0.3 | 132.2 ± 5.0 | 17.9 ± 0.6 | 48.7 ± 8.4 | 7.8 ± 0.4 | 24.2 ± 1.4 | 12.6 ± 0.7 |  |  |
| TD621 | 42.0 ± 2.7 | 33.6 ± 0.3 |  |  | 7.4 | 117.0 ± 6.6 | 71.5 ± 3.7 | 56.1 ± 6.3 | 80.0 ± 9.8 | 39.4 ± 3.4 | 43.3 ± 3.8 |  |  |
| TD622 | 101.7 ± 6.5 | 48.7 ± 2.7 |  |  |  | 103.4 ± 6.6 | 105.2 ± 6.4 | 113.5 ± 3.8 | 54.1 ± 6.0 | 63.0 ± 3.6 | 62.0 ± .1 |  |  |
| TD623 |  |  |  |  |  |  |  |  |  |  |  |  |  |
| TD624 | 90.8 ± 4.8 |  |  |  |  | 15.7 ± 0.8 |  | 14.3 ± 3.6 |  | 11.9 ± 1.0 |  |  |  |
| TD625 | 223.5 ± 7.0 |  |  |  |  | 115.4 ± 7.2 |  | 73.7 ± 3.0 |  | 92.6 ± 7.4 |  |  |  |
| TD626 | 111.2 ± 1.3 |  |  |  |  | 39.0 ± 2.2 |  | 40.4 ± 0.8 |  | 24.3 ± 3.6 |  |  |  |
| TD627 |  |  |  |  |  |  |  |  |  |  |  |  |  |
| TD628 | 146.8 ± 4.5 |  |  |  |  | 151.9 ± 1.7 |  | 121.6 ± 7.1 |  | 140.0 ± 7.3 |  |  |  |
| TD629 | 132.8 ± 1.0 |  |  |  |  | 140.2 ± 1.6 |  | 118.4 ± 1.2 |  | 113.4 ± 3.6 |  |  |  |
| TD630 | 40.9 ± 0.7 |  |  |  |  | 48.4 ± 1.1 |  | 50.3 ± 2.1 |  | 24.3 ± 1.0 |  |  |  |
| TD631 | 42.5 ± 2.8 |  |  |  |  | 35.8 ± 6.9 |  | 58.9 ± 3.1 |  | 40.4 ± 1.9 |  |  |  |

| Compound | SW900 cell viability (%) | | BA (%) | minimal concentration to disrupt SET-PP2Ac binding (nM) | minimal concentration for PP2A activation (nM) |
|---|---|---|---|---|---|
|  | 1 (uM) | 10 (uM) |  |  |  |
| TD618 |  |  | 62 | >200 | >200 |
| TD619 |  |  |  |  |  |
| TD620 |  |  |  |  |  |
| TD621 |  |  |  |  |  |
| TD622 |  |  |  |  |  |
| TD623 |  |  |  |  |  |
| TD624 |  |  |  |  |  |
| TD625 |  |  |  |  |  |
| TD626 |  |  |  |  |  |
| TD627 |  |  |  |  |  |
| TD628 |  |  |  |  |  |
| TD629 |  |  |  |  |  |
| TD630 |  |  |  |  |  |
| TD631 |  |  |  |  |  |

What is claimed is:

1. An aryl amine substituted quinoxaline which is represented by Formula I(a) or Formula I(b)

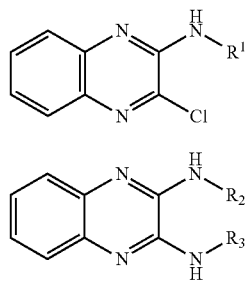

wherein $R_1$, $R_2$ and $R_3$ are same or different members selected from the group consisting of:

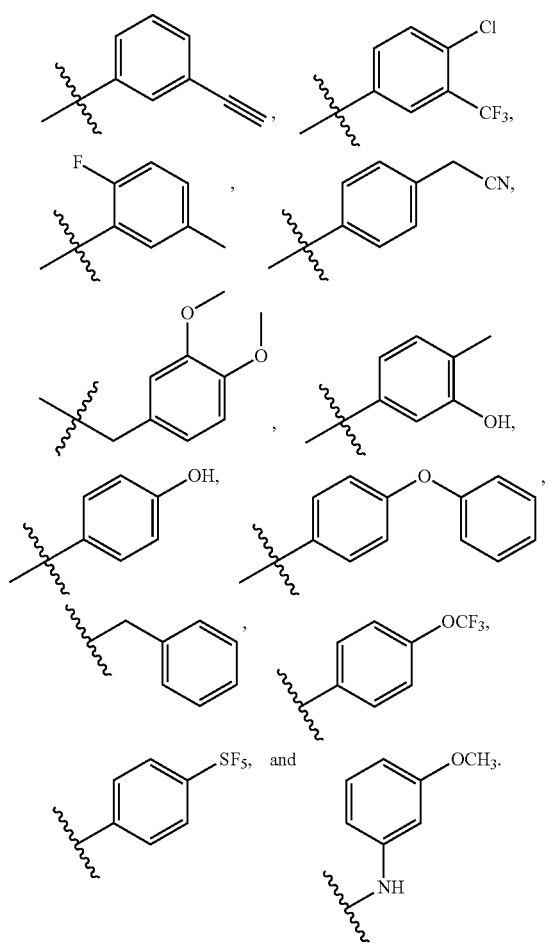

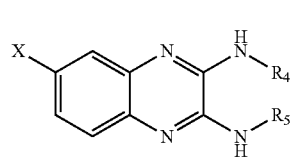

2. An aryl amine substituted quinoxaline which is represented by Formula I(c)

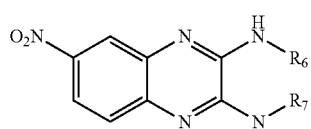

wherein $R_4$ and $R_5$ are same or different members selected from the group consisting of:

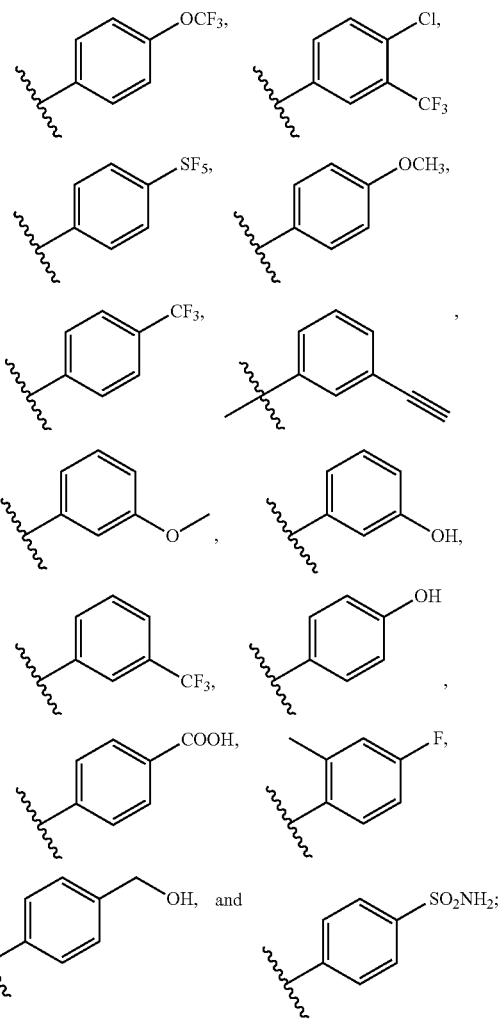

and wherein X is a halogen, haloalkyl, methoxy, nitro, amino, amido, carboxyl or benzophenonyl group.

3. An aryl amine substituted quinoxaline which is represented by Formula I(d)

I(d)

wherein $R_6$ and $R_7$ are same or different members selected from the group consisting of:

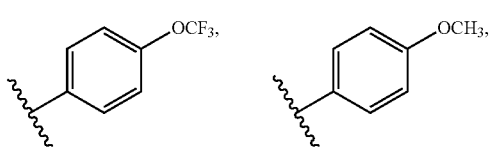

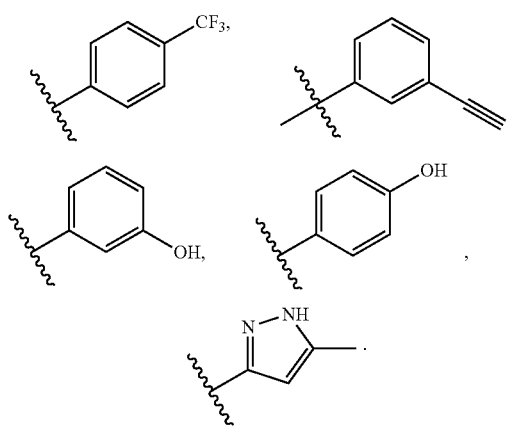

4. A compound which is represented by Formula II

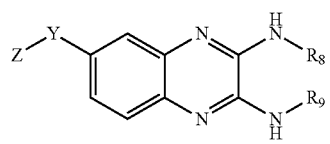
II wherein $R_8$ and $R_9$ are same or different members selected from the group consisting of:

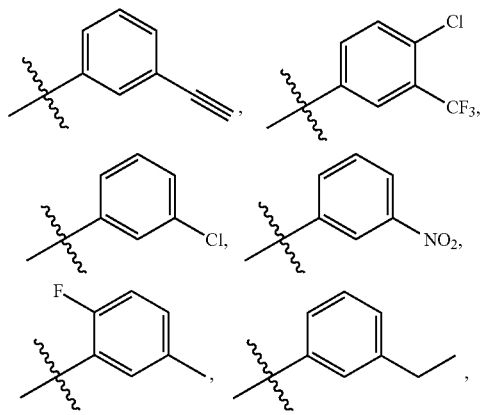

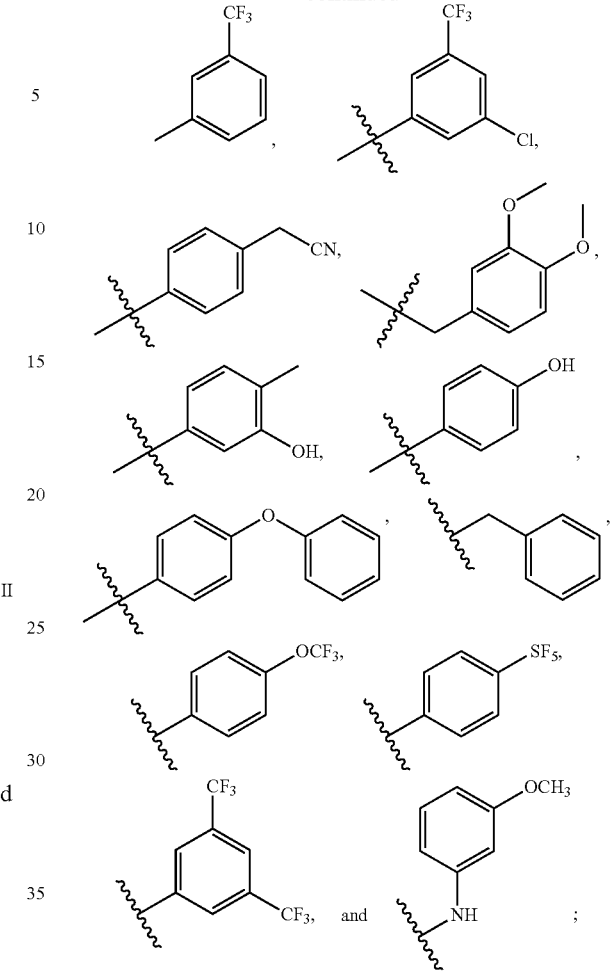

and wherein Y is CO or $(CH_2)_n$, n=1-3; Z=COOR$^{10}$, or a phenyl substituted with a functional group, leis aryl or alkyl.

5. A pharmaceutical composition comprising a compound as defined in any of claims 1 to 4 and a pharmacologically acceptable carrier.

6. The pharmaceutical composition of claim 5, further comprising an anti-cancer drug.

7. The pharmaceutical composition of claim 6, wherein the anti-cancer drug is sorafenib or paclitaxel.

* * * * *